United States Patent
Corson et al.

(10) Patent No.: US 12,161,642 B2
(45) Date of Patent: Dec. 10, 2024

(54) FERROCHELATASE INHIBITORS AND METHODS OF USE

(71) Applicants: INDIANA UNIVERSITY RESEARCH AND TECHNOLOGY CORPORATION, Indianapolis, IN (US); Gachon University of Industry-Academic Cooperation, Gyeonggi-do (KR)

(72) Inventors: Timothy W. Corson, Fishers, IN (US); Kamakshi Sishtla, Indianapolis, IN (US); Seung-Yong Seo, Gyeonggi-do (KR); Bit Lee, Gyeonggi-do (KR)

(73) Assignees: INDIANA UNIVERSITY RESEARCH AND TECHNOLOGY CORPORATION, Indianapolis, IN (US); Gachon University of Industry—Academic Cooperation, Gyeonggi-do (KR)

( * ) Notice: Subject to any disclaimer, the term of this patent is extended or adjusted under 35 U.S.C. 154(b) by 927 days.

(21) Appl. No.: 17/051,018

(22) PCT Filed: Apr. 30, 2019

(86) PCT No.: PCT/US2019/029909
§ 371 (c)(1),
(2) Date: Oct. 27, 2020

(87) PCT Pub. No.: WO2019/213076
PCT Pub. Date: Nov. 7, 2019

(65) Prior Publication Data
US 2021/0121465 A1   Apr. 29, 2021

Related U.S. Application Data

(60) Provisional application No. 62/664,601, filed on Apr. 30, 2018.

(51) Int. Cl.
| | |
|---|---|
| A61K 31/519 | (2006.01) |
| A61K 31/122 | (2006.01) |
| A61K 31/155 | (2006.01) |
| A61K 31/343 | (2006.01) |
| A61K 31/37 | (2006.01) |
| A61K 31/4025 | (2006.01) |
| A61K 31/409 | (2006.01) |
| A61K 31/4196 | (2006.01) |
| A61K 31/4706 | (2006.01) |
| A61K 31/4709 | (2006.01) |
| A61K 31/49 | (2006.01) |
| A61K 38/17 | (2006.01) |
| A61K 39/395 | (2006.01) |
| A61K 41/00 | (2020.01) |
| A61K 45/06 | (2006.01) |
| A61P 27/02 | (2006.01) |
| C07D 249/14 | (2006.01) |
| C07D 487/04 | (2006.01) |
| C07K 16/22 | (2006.01) |
| C12N 15/113 | (2010.01) |
| A61K 39/00 | (2006.01) |

(52) U.S. Cl.
CPC ......... *A61K 31/519* (2013.01); *A61K 31/122* (2013.01); *A61K 31/155* (2013.01); *A61K 31/343* (2013.01); *A61K 31/37* (2013.01); *A61K 31/4025* (2013.01); *A61K 31/409* (2013.01); *A61K 31/4196* (2013.01); *A61K 31/4706* (2013.01); *A61K 31/4709* (2013.01); *A61K 31/49* (2013.01); *A61K 38/17* (2013.01); *A61K 38/179* (2013.01); *A61K 39/3955* (2013.01); *A61K 41/0057* (2013.01); *A61K 45/06* (2013.01); *A61P 27/02* (2018.01); *C07D 249/14* (2013.01); *C07D 487/04* (2013.01); *C07K 16/22* (2013.01); *C12N 15/1137* (2013.01); *A61K 2039/505* (2013.01); *C12N 2310/11* (2013.01); *C12N 2320/31* (2013.01)

(58) Field of Classification Search
CPC .... A61K 31/519; A61K 31/122; A61K 38/17; A61P 27/02; C07D 249/14
See application file for complete search history.

(56) References Cited

U.S. PATENT DOCUMENTS

| | | |
|---|---|---|
| 8,759,357 B2 | 6/2014 | Shipps, Jr. et al. |
| 2016/0022742 A1 | 1/2016 | Zender et al. |
| 2016/0222388 A1 | 8/2016 | Corson et al. |

(Continued)

FOREIGN PATENT DOCUMENTS

| | | |
|---|---|---|
| CN | 106749271 A | 5/2017 |
| DE | 4305279 A1 | 8/1994 |
| WO | 2010056630 A1 | 5/2010 |

(Continued)

OTHER PUBLICATIONS

RN 1216714-38-3, Publication Date: Apr. 5, 2010 (Year: 2010).*

(Continued)

*Primary Examiner* — Peter J Reddig
*Assistant Examiner* — Cheng Lu
(74) *Attorney, Agent, or Firm* — Barnes & Thornburg LLP

(57) ABSTRACT

The invention relates to a method of treatment of a patient with a ferrochelatase inhibitor, or a pharmaceutically acceptable salt thereof, or a derivative thereof. Also, the invention relates to a method of treatment of a patient with a ferrochelatase inhibitor that is a triazolopyrimidinone, or a derivative thereof, or a pharmaceutically acceptable salt thereof.

8 Claims, 9 Drawing Sheets

(56) References Cited

U.S. PATENT DOCUMENTS

2017/0145016 A1  5/2017  Heo et al.

FOREIGN PATENT DOCUMENTS

| WO | WO-2010056631 A1 * | 5/2010 | ........... C07D 487/04 |
|----|---------------------|--------|--------------------------|
| WO | 2011043994 A1 | 4/2011 | |
| WO | 2018071282 A1 | 4/2018 | |
| WO | 2018089967 A1 | 5/2018 | |

OTHER PUBLICATIONS

Extended European Search Report and Written Opinion of completed by the ISA/US on Dec. 23, 2021 and issued in connection with PCT/US2019/029909.

Boechat, Nubia et al, "New Triflouromethyl Triazolopyrimidines as Anti-Plasmodium Falciparum Agents"; Molecules 2012, 17, pp. 8285-8302; doi: 10.3390/Molecules 17078285.

PCT International Search Report and Written Opinion completed by the ISA/US on Jun. 12, 2019 and issued in connection with PCT/US2019/029909.

PUBCHEM-CID: 719053 Create Date: Jul. 8, 2005 (Jul. 8, 2005) pp. 1-9; p. 2, structure.

European Office Action dated Jun. 25, 2024, issued in connection with EP Appln. No. 19796293.9, 5 pages.

* cited by examiner

DMSO

5a 100 μM

5c 100 µM

5d 100 µM

5h 10 µM

FERROCHELATASE INHIBITORS AND METHODS OF USE

CROSS-REFERENCE TO RELATED APPLICATIONS

This is a national stage entry of International Patent Application No. PCT/US2019/029909, filed Apr. 30, 2019, which claims the benefit of and priority to U.S. Provisional Patent Application No. 62/664,601 filed Apr. 30, 2018, the disclosures of which are incorporated herein by references in their entireties

STATEMENT OF GOVERNMENT SUPPORT

This invention was made with government support under TR001106 and EY025641 awarded by the National Institutes of Health. The government has certain rights in the invention.

FIELD OF THE DISCLOSURE

The invention relates to a method of treatment of a patient with a ferrochelatase inhibitor, or a derivative thereof, or a pharmaceutically acceptable salt thereof. Also, the invention relates to a method of treatment of a patient with a ferrochelatase inhibitor that is a triazolopyrimidinone, or a derivative thereof, or a pharmaceutically acceptable salt thereof.

BACKGROUND AND SUMMARY OF THE DISCLOSURE

The present disclosure relates generally to ferrochelatase inhibitors and methods of using the inhibitors in antiangiogenetic therapies and for other therapies. In particular, triazolopyrimidinones, or derivatives thereof, or pharmaceutically acceptable salts thereof, can function as ferrochelatase inhibitors to treat angiogenesis-mediated diseases and disorders (e.g., cancer), and neovascular diseases, such as neovascular eye diseases. Triazolopyrimidinones, or derivatives thereof, or pharmaceutically acceptable salts thereof, can also be used to treat malaria.

The heme synthesis enzyme ferrochelatase (FECH; EC 4.99.1.1) has garnered considerable interest since it was first purified in 1981. Found in the mitochondrion, it is responsible for the final step of heme biosynthesis, insertion of a ferrous ion into the center of the porphyrin ring of protoporphyrin IX (PPIX). Partial loss-of-function mutations in the FECH gene cause erythropoietic protoporphyria, a blood disorder characterized by phototoxic buildup of PPIX. Thus, there have been efforts to find small molecule activators of ferrochelatase to potentially treat conditions of reduced FECH activity.

But in recent years, inhibition of FECH has also emerged as a potential therapeutic avenue for multiple indications. Two FECH inhibitors are widely used in preclinical studies. N-methylprotoporphyrin (NMPP) is a transition-state analog and fairly potent FECH inhibitor. The long-approved antifungal drug griseofulvin, interestingly, forms NMPP in vivo by alkylating the heme group of cytochrome P450, and thus, can be used as a novel FECH inhibitor in cells and intact organisms. FECH is also a common off-target protein molecule of kinase inhibitor cancer drugs, but of course, these agents have other major biological targets. The need for useful, specific FECH inhibitors has been highlighted by a growing body of work implicating this protein in disease.

For example, FECH has been identified as a mediator of ocular neovascularization. Neovascularization is a key pathological determinant of a number of major, blinding eye diseases including, but not limited to, retinopathy of prematurity, wet age-related macular degeneration (AMD), and proliferative diabetic retinopathy. FECH is upregulated in both human and murine eyes undergoing choroidal neovascularization (as seen in wet AMD). Moreover, knockdown or mutation of FECH blocks angiogenesis in vitro and in vivo. In vitro, both NMPP and griseofulvin selectively block endothelial cell growth without causing cell death, and in vivo, oral or intravitreal (into the eye) griseofulvin reduces choroidal neovascularization. FECH is also upregulated in mouse eyes undergoing oxygen-induced retinopathy, a model of the retinal angiogenesis seen in diseases like retinopathy of prematurity and proliferative diabetic retinopathy, and intravitreal griseofulvin is an effective therapy in this model. Depletion of the heme cofactor needed for the function of proangiogenic signaling proteins like endothelial nitric oxide synthase seems to be a key mechanism for the antiangiogenic effects of FECH inhibition. Development of FECH-targeting agents could complement or replace the anti-vascular endothelial growth factor agents currently used, for example, to treat diseases involving neovascularization, which are not effective in all patients, and are associated with side effects.

Surprisingly, FECH also plays a role in malaria. New treatments are sorely needed for this mosquito-borne parasitic disease, and host proteins are intriguing targets. Although the pathogenic *Plasmodium* species have their own FECH gene, it is dispensable; and thus, the parasites are seemingly reliant on the host erythrocyte FECH. Thus, Fech mutant mice are resistant to *Plasmodium* infection, and the erythrocytes of erythropoietic protoporphyria patients poorly support *Plasmodium* growth. Moreover, NMPP blocks parasite growth in vitro, with griseofulvin having a similar effect. The blood of griseofulvin-treated patients also shows reduced *Plasmodium* growth. Therefore, new ways of blocking FECH could have utility in treating malaria.

Finally, FECH inhibition may find utility in cancer treatment. One mode of photodynamic therapy (PDT) and photodynamic diagnosis (PDD) can benefit from FECH inhibition. Dosing patients with the first compound in the heme biosynthesis pathway, 5-aminolevulinic acid, leads to buildup of the phototoxic PPIX, especially in certain cancer types with already-low FECH activity, such as glioblastoma. Given that FECH converts PPIX into heme, blockade of FECH can potentiate this process, enhancing the PDT/PDD effect. This has been shown in multiple systems. Glioma, breast carcinoma, and urothelial carcinoma cells with FECH knockdown showed enhanced 5-aminolevulinic acid-mediated PDT, and colon cancer cells showed increased PPIX. Griseofulvin enhanced ALA-PDT in osteosarcoma and an oral squamous cell carcinoma cell line. In urothelial carcinoma cells and an animal model, using the iron chelator deferoxamine to indirectly block FECH function (by removing one of its substrates) led to enhanced PDT. Similar effects were seen in prostate cancer models, histiocytic lymphoma, and gastric cancer. And in mouse cutaneous tumors, blockade of FECH with (toxic) $Pb^{2+}$ (which interferes with normal, $Fe^{2+}$ metalation of PPIX) enhanced PPIX buildup and phototoxicity.

Given all these appealing potential utilities of FECH inhibitors, and the limitations of other inhibitors and indirect methods of FECH inhibition, there is a need for additional small molecule FECH inhibitors.

The present disclosure is generally related to FECH inhibitors and uses of the same for treating various diseases and disorders. Particularly, using a high throughput screen for FECH inhibition, the present disclosure identified a series of triazolopyrimidinone hits. Novel derivatives of these hit compounds were then synthesized. Some of these perform as well as NMPP in FECH inhibition assays, and have drug-like properties.

Accordingly, in one aspect, the present disclosure is directed to a compound of the formula

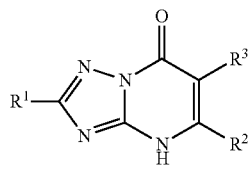

wherein
  $R^1$ is $C_6$-$C_{10}$ aryl or $C_1$-$C_6$ alkylN$R^4R^5$, wherein each hydrogen atom in $C_6$-$C_{10}$ aryl is independently optionally substituted with $C_1$-$C_6$ alkyl;
  each of $R^2$ and $R^3$ is independently selected from the group consisting of H, $C_1$-$C_6$ alkyl, or $C_1$-$C_6$ alkylN$R^6R^7$, provided that at least one of $R^2$ and $R^3$ is not H, and when $R^1$ is $C_1$-$C_6$ alkylN$R^4R^5$, then $R^2$ is $C_3$-$C_6$ alkyl, and $R^3$ is H, wherein each hydrogen atom in $C_1$-$C_6$ alkyl is independently optionally substituted with fluoro, chloro, bromo, or iodo; or $R^2$ and $R^3$, when taken together with the carbon atoms to which they are attached, form a 5-7 membered carbocyclic ring;
  $R^4$ is H;
  $R^5$ is biphenyl, 4-tert-butylphenyl, 3-chloro-4-fluoro-phenyl, 3-fluoro-4-fluoro-phenyl, 4-(O—$C_1$-$C_6$ alkoxy) phenyl, 4-(OCF$_3$)phenyl, 2-methylphenyl, 3-methylphenyl, or 4-methylphenyl, with the proviso that when $R^2$ and $R^3$, when taken together with the carbon atoms to which they are attached, form a 5-7 membered carbocyclic ring, then $R^5$ is 4-methylphenyl; and
  each of $R^6$ or $R^7$ is independently selected from the group consisting of H, $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl, wherein each hydrogen atom in $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl is independently optionally substituted with fluoro, chloro, bromo, iodo, $C_1$-$C_6$ alkyl, —O$C_1$-$C_6$ alkyl, —OCF$_3$, —CF$_3$ or $C_6$-$C_{10}$ aryl;
or a pharmaceutically acceptable salt thereof.

In another embodiment, the present disclosure is directed to a ferrochelatase inhibitor of compound 2

Compound 2

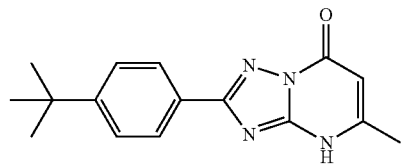

In another embodiment, the present disclosure is directed to a ferrochelatase inhibitor of compound 3

Compound 3

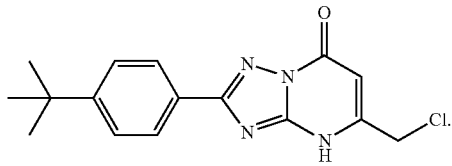

In another embodiment, the present disclosure is directed to a ferrochelatase inhibitor of compound 4a Compound 4a

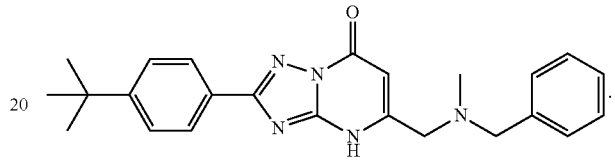

In yet another embodiment, the present disclosure is directed to a ferrochelatase inhibitor of compound 4b Compound 4b

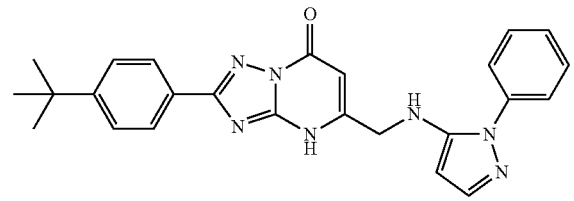

In another embodiment, the present disclosure is directed to a ferrochelatase inhibitor of compound 4c Compound 4c

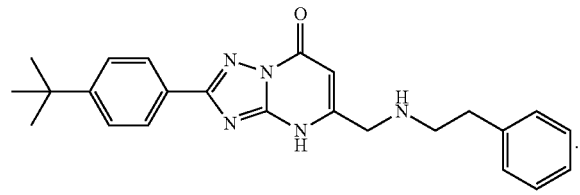

In another embodiment, the present disclosure is directed to a ferrochelatase inhibitor of compound 4d Compound 4d In yet another embodiment, the present disclosure is directed to a ferrochelatase inhibitor of compound 4e Compound 4e

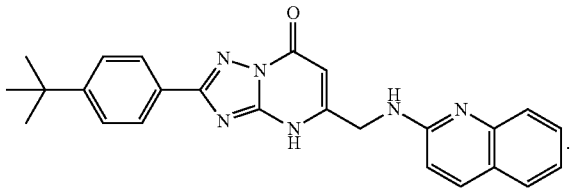

In another embodiment, the present disclosure is directed to a ferrochelatase inhibitor of compound 4f Compound 4f

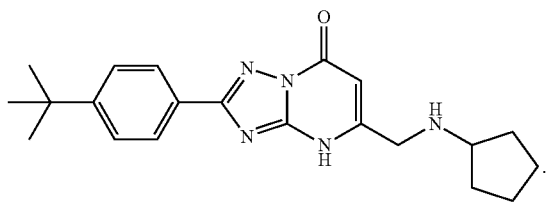

In yet another embodiment, the present disclosure is directed to a ferrochelatase inhibitor of compound 4g Compound 4g

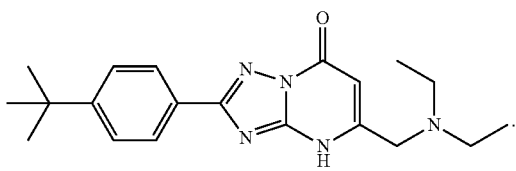

In another embodiment, a method for treating a patient with an angiogenesis-mediated disease is provided. In some embodiments, the method comprises administering to the patient a triazolopyrimidinone, or a derivative thereof, or a pharmaceutically acceptable salt thereof. In some embodiments, the method comprises administering to the patient a compound of the formula

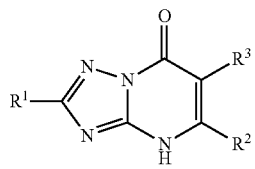

wherein
  $R^1$ is $C_1$-$C_6$ alkyl, $C_2$-$C_6$ alkenyl, $C_2$-$C_6$ alkynyl, or $C_6$-$C_{10}$ aryl, or $C_1$-$C_6$ alkyNR$^4$R$^5$, wherein each hydrogen atom in $C_1$-$C_6$ alkyl, $C_2$-$C_6$ alkenyl, $C_2$-$C_6$ alkynyl, or $C_6$-$C_{10}$ aryl, is independently optionally substituted with fluoro, chloro, bromo, iodo, $C_1$-$C_6$ alkyl, —OC$_1$-$C_6$ alkyl, or $C_6$-$C_{10}$ aryl;
  each of $R^2$ and $R^3$ is independently selected from the group consisting of H, $C_1$-$C_6$ alkyl, $C_2$-$C_6$ alkenyl, $C_2$-$C_6$ alkynyl, $C_6$-$C_{10}$ aryl, $C_1$-$C_6$ alkyl-$C_6$-$C_{10}$ aryl, and $C_1$-$C_6$ alkyNR$^6$R$^7$, provided that at least one of $R^2$ and $R^3$ is not H, wherein each hydrogen atom in $C_1$-$C_6$ alkyl, $C_2$-$C_6$ alkenyl, $C_2$-$C_6$ alkynyl, $C_6$-$C_{10}$ aryl, or $C_1$-$C_6$ alkyl-$C_6$-$C_{10}$ aryl, is independently optionally substituted with fluoro, chloro, bromo, iodo, —CO$_2$R$^8$, $C_1$-$C_6$ alkyl, —OC$_1$-$C_6$ alkyl, or $C_6$-$C_{10}$ aryl; or $R^2$ and $R^3$, when taken together with the carbon atoms to which they are attached, form a 5-7 membered carbocyclic ring;
  each of $R^4$, $R^5$, $R^6$, or $R^7$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, and $C_1$-$C_6$ alkyl-$C_6$-$C_{10}$ aryl, wherein each hydrogen atom in $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, or $C_1$-$C_6$ alkyl-$C_6$-$C_{10}$ aryl is independently optionally substituted with fluoro, chloro, bromo, iodo, —CO$_2$R$^8$, $C_1$-$C_6$ alkyl, —OC$_1$-$C_6$ alkyl, —OCF$_3$, —CF$_3$ or $C_6$-$C_{10}$ aryl; and
  $R^8$ is H or $C_1$-$C_6$ alkyl;
  or a pharmaceutically acceptable salt thereof.

In another embodiment, a method for treating a patient with malaria is provided. The method comprises administering to the patient a triazolopyrimidinone, or a derivative thereof, or a pharmaceutically acceptable salt thereof. In some embodiments, the triazolopyrimidinone, or the derivative thereof, or the pharmaceutically acceptable salt thereof, comprises a compound of the formula

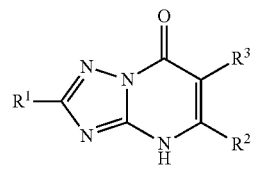

wherein
  $R^1$ is $C_6$-$C_{10}$ aryl or $C_1$-$C_6$ alkyNR$^4$R$^5$, wherein each hydrogen atom in $C_6$-$C_{10}$ aryl is independently optionally substituted with $C_1$-$C_6$ alkyl;
  each of $R^2$ and $R^3$ is independently selected from the group consisting of H, $C_1$-$C_6$ alkyl, or $C_1$-$C_6$ alkyNR$^6$R$^7$, provided that at least one of $R^2$ and $R^3$ is not H, and when $R^1$ is $C_1$-$C_6$ alkyNR$^4$R$^5$, then $R^2$ is $C_3$-$C_6$ alkyl, and $R^3$ is H, wherein each hydrogen atom in $C_1$-$C_6$ alkyl is independently optionally substituted with fluoro, chloro, bromo, or iodo; or $R^2$ and $R^3$, when taken together with the carbon atoms to which they are attached, form a 5-7 membered carbocyclic ring;
  each of $R^4$ is H;
  $R^5$ is biphenyl, 4-tert-butylphenyl, 3-chloro-4-fluoro-phenyl, 3-fluoro-4-fluoro-phenyl, 4-(O—$C_1$-$C_6$ alkoxy) phenyl, 4-(OCF$_3$)phenyl, 2-methylphenyl, 3-methylphenyl, or 4-methylphenyl, with the proviso that when $R^2$ and $R^3$, when taken together with the carbon atoms to which they are attached, form a 5-7 membered carbocyclic ring, then $R^5$ is 4-methylphenyl; and
  each of $R^6$ or $R^7$ is independently selected from the group consisting of H, $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl, wherein each hydrogen atom in $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl is independently optionally substituted with fluoro, chloro, bromo, iodo, $C_1$-$C_6$ alkyl, —$OC_1$-$C_6$ alkyl, —$OCF_3$, —$CF_3$ or $C_6$-$C_{10}$ aryl; or a pharmaceutically acceptable salt thereof. In other embodiments, wherein the disease is malaria, the method further comprises administering one or more of chloroquine (Aralen), quinine sulfate (Qualaquin), artemisinin, hydroxychloroquine (Plaquenil), mefloquine, a combination of atovaquone and proguanil (Malarone), and combinations thereof.

The various embodiments described in the numbered clauses below are applicable to any of the embodiments described in this "SUMMARY" section and the sections of the patent application titled "DETAILED DESCRIPTION OF ILLUSTRATIVE EMBODIMENTS" or "EXAMPLES" or in the "CLAIMS" appended to this application.

1. A compound of the formula

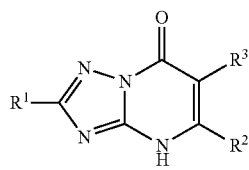

wherein
$R^1$ is $C_6$-$C_{10}$ aryl or $C_1$-$C_6$ alkylNR$^4$R$^5$, wherein each hydrogen atom in $C_6$-$C_{10}$ aryl is independently optionally substituted with $C_1$-$C_6$ alkyl;
each of $R^2$ and $R^3$ is independently selected from the group consisting of H, $C_1$-$C_6$ alkyl, or $C_1$-$C_6$ alkylNR$^6$R$^7$, provided that at least one of $R^2$ and $R^3$ is not H, and when $R^1$ is $C_1$-$C_6$ alkylNR$^4$R$^5$, then $R^2$ is $C_3$-$C_6$ alkyl, and $R^3$ is H, wherein each hydrogen atom in $C_1$-$C_6$ alkyl is independently optionally substituted with fluoro, chloro, bromo, or iodo; or $R^2$ and $R^3$, when taken together with the carbon atoms to which they are attached, form a 5-7 membered carbocyclic ring;
$R^4$ is H;
$R^5$ is biphenyl, 4-tert-butylphenyl, 3-chloro-4-fluoro-phenyl, 3-fluoro-4-fluoro-phenyl, 4-(O—$C_1$-$C_6$ alkoxy) phenyl, 4-($OCF_3$)phenyl, 2-methylphenyl, 3-methylphenyl, or 4-methylphenyl, with the proviso that when $R^2$ and $R^3$, when taken together with the carbon atoms to which they are attached, form a 5-7 membered carbocyclic ring, then $R^5$ is 4-methylphenyl; and
each of $R^6$ or $R^7$ is independently selected from the group consisting of H, $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl, wherein each hydrogen atom in $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl is independently optionally substituted with fluoro, chloro, bromo, iodo, $C_1$-$C_6$ alkyl, —$OC_1$-$C_6$ alkyl, —$OCF_3$, —$CF_3$ or $C_6$-$C_{10}$ aryl;
or a pharmaceutically acceptable salt thereof.

2. The compound of clause 1, or a pharmaceutically acceptable salt thereof, wherein $R^1$ is $C_6$-$C_{10}$ aryl, wherein each hydrogen atom in $C_6$-$C_{10}$ aryl is independently optionally substituted with $C_1$-$C_6$ alkyl.

3. The compound of clause 1 or 2, or a pharmaceutically acceptable salt thereof, wherein $R^1$ is 4-tert-butylphenyl.

4. The compound of any of the preceding clauses, or a pharmaceutically acceptable salt thereof, wherein $R^2$ is $C_1$-$C_6$ alkylNR$^6$R$^7$, and $R^3$ is H.

5. The compound of clause 1, or a pharmaceutically acceptable salt thereof, wherein $R^1$ is $C_1$-$C_6$ alkylNR$^4$R$^5$.

6. The compound of clause 1 or 5, or a pharmaceutically acceptable salt thereof, wherein $R^2$ is n-propyl or iso-propyl, and $R^3$ is H.

7. The compound of clause 1, or a pharmaceutically acceptable salt thereof, wherein $R^2$ and $R^3$, when taken together with the carbon atoms to which they are attached, form a 5-7 membered carbocyclic ring.

8. The compound of clause 1 or 7, or a pharmaceutically acceptable salt thereof, wherein $R^2$ and $R^3$, when taken together with the carbon atoms to which they are attached, form a 5-membered carbocyclic ring.

9. A ferrochelatase inhibitor selected from the group consisting of

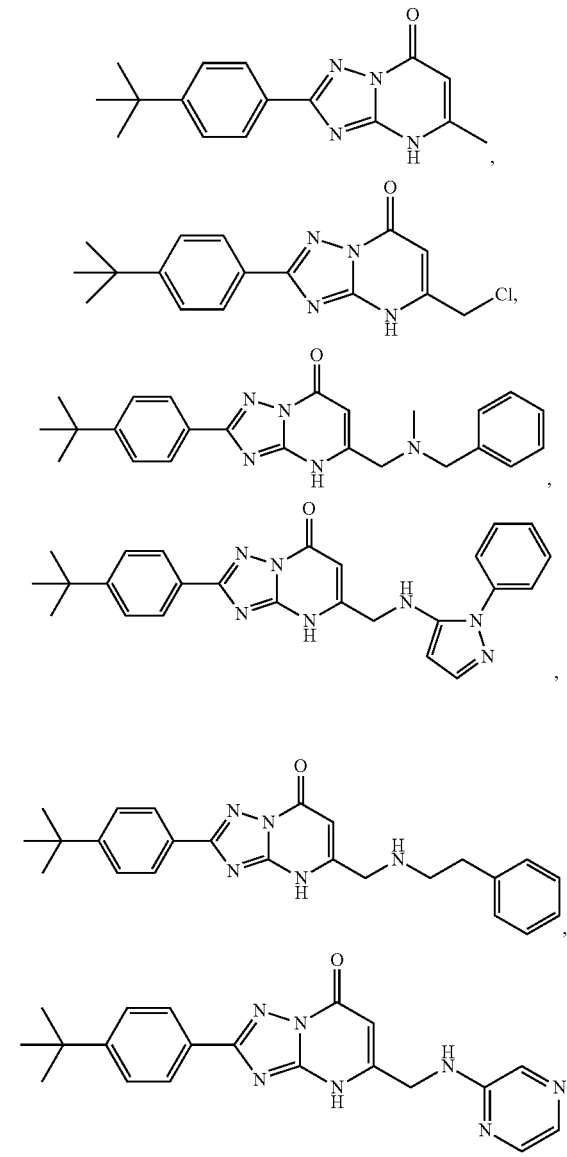

-continued

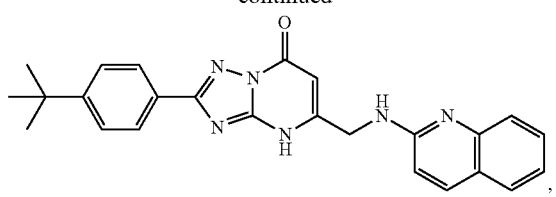

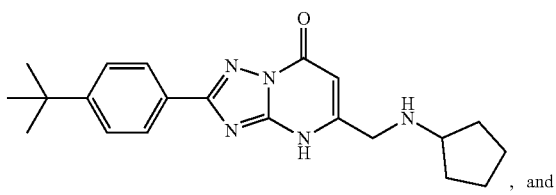

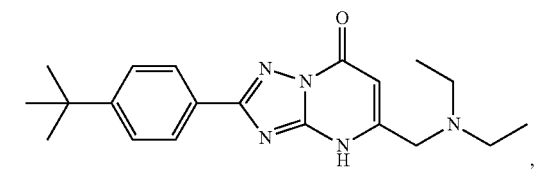

or a pharmaceutically acceptable salt thereof.

10. A ferrochelatase inhibitor selected from the group consisting of

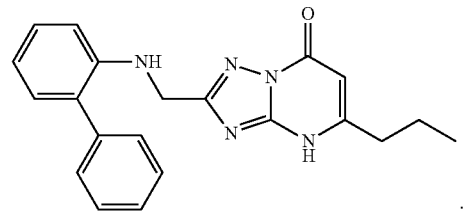

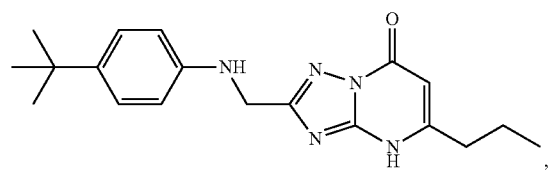

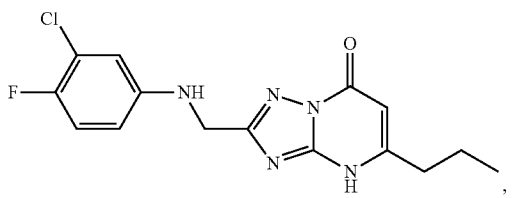

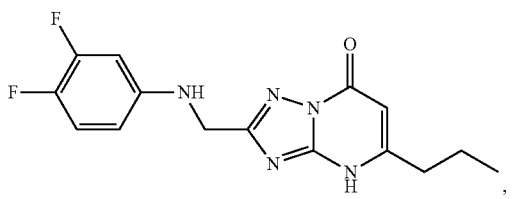

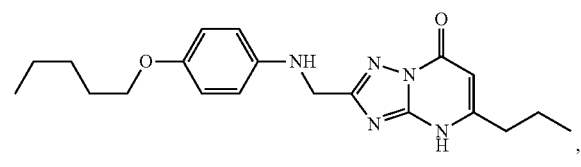

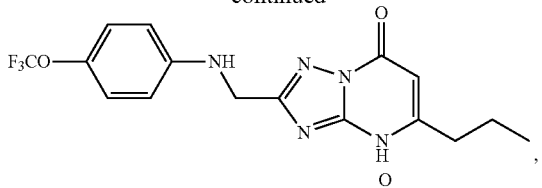

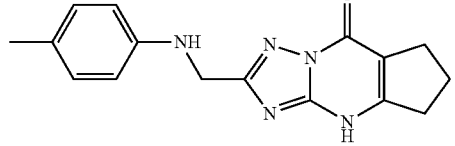

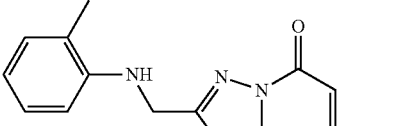

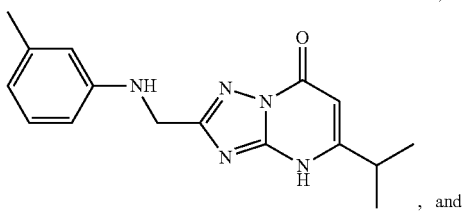

or a pharmaceutically acceptable salt thereof.

11. A method for treating a patient with an angiogenesis-mediated disease, the method comprising administering to the patient a triazolopyrimidinone, or a derivative thereof, or a pharmaceutically acceptable salt thereof.

12. The method of clause 11, wherein the triazolopyrimidinone, or the derivative thereof, or the pharmaceutically acceptable salt thereof, comprises a compound of the formula

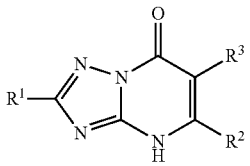

wherein $R^1$ is $C_1$-$C_6$ alkyl, $C_2$-$C_6$ alkenyl, $C_2$-$C_6$ alkynyl, or $C_6$-$C_{10}$ aryl, or $C_1$-$C_6$ alkyNR$^4$R$^5$, wherein each hydrogen atom in $C_1$-$C_6$ alkyl, $C_2$-$C_6$ alkenyl, $C_2$-$C_6$ alkynyl, or $C_6$-$C_{10}$ aryl, is independently optionally substituted with fluoro, chloro, bromo, iodo, $C_1$-$C_6$ alkyl, —O$C_1$-$C_6$ alkyl, or $C_6$-$C_{10}$ aryl;

each of $R^2$ and $R^3$ is independently selected from the group consisting of H, $C_1$-$C_6$ alkyl, $C_2$-$C_6$ alkenyl, $C_2$-$C_6$ alkynyl, $C_6$-$C_{10}$ aryl, $C_1$-$C_6$ alkyl-$C_6$-$C_{10}$ aryl, and $C_1$-$C_6$ alkyNR$^6$R$^7$, provided that at least one of R$^2$ and R$^3$ is not H, wherein each hydrogen atom in $C_1$-$C_6$ alkyl, $C_2$-$C_6$ alkenyl, $C_2$-$C_6$ alkynyl, $C_6$-$C_{10}$ aryl, or $C_1$-$C_6$ alkyl-$C_6$-$C_{10}$ aryl, is independently optionally substituted with fluoro, chloro, bromo, iodo, —CO$_2$R$^8$, $C_1$-$C_6$ alkyl, —OC$_1$-$C_6$ alkyl, or $C_6$-$C_{10}$ aryl; or R$^2$ and R$^3$, when taken together with the carbon atoms to which they are attached, form a 5-7 membered carbocyclic ring;

each of R$^4$, R$^5$, R$^6$, or R$^7$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, and $C_1$-$C_6$ alkyl-$C_6$-$C_{10}$ aryl, wherein each hydrogen atom in $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, or $C_1$-$C_6$ alkyl-$C_6$-$C_{10}$ aryl is independently optionally substituted with fluoro, chloro, bromo, iodo, —CO$_2$R$^8$, $C_1$-$C_6$ alkyl, —OC$_1$-$C_6$ alkyl, —OCF$_3$, —CF$_3$ or $C_6$-$C_{10}$ aryl; and R$^8$ is H or $C_1$-$C_6$ alkyl.

13. The method of any one of clauses 11 or 12, comprising administering to the patient the triazolopyrimidinone, or the derivative thereof, or the pharmaceutically acceptable salt thereof, to achieve an intravitreal concentration of from about 0.01 μM to about 1000 μM.

14. The method of any one of clauses 11 to 13, wherein the angiogenesis-mediated disease is selected from the group consisting of cancer, a disease involving neovascularization, retinopathy of prematurity, wet age-related macular degeneration, hypertensive retinopathy, central retinal vein occlusion, branch retinal vein occlusion, neovascular glaucoma, retinoblastoma, diabetic macular edema, and proliferative diabetic retinopathy.

15. The method of any one of clauses 11 to 14 further comprising administering one or more of N-methylprotoporphyrin (NMPP) or an analog thereof, griseofulvin or an analog thereof, antisense RNA targeting ferrochelatase RNA, an agent for RNA silencing or RNA interference (RNAi) targeting ferrochelatase RNA, an agent for CRISPR/Cas9-mediated or Zinc-finger nuclease-mediated genetic ablation of ferrochelatase (FECH) DNA, an agent for anti-VEGF therapy, and combinations thereof.

16. The method of any one of clauses 11 to 15, comprising administering to the patient the triazolopyrimidinone, or the derivative thereof, or the pharmaceutically acceptable salt thereof, to achieve an intravitreal concentration of from about 0.01 μM to about 500 μM.

17. The method of clause 14, wherein the disease is cancer and the cancer is selected from the group consisting of glioma, breast cancer, bladder cancer, colon cancer, and combinations thereof.

18. The method of clause 17 further comprising treating the patient with photodynamic therapy (PDT).

19. The method of any one of clauses 11 to 16 wherein the triazolopyrimidinone, or the derivative thereof, or the pharmaceutically acceptable salt thereof, is used to treat an ocular disease and is administered directly into the eye.

20. The method of clause 19 wherein the triazolopyrimidinone, or the derivative thereof, or the pharmaceutically acceptable salt thereof, is administered by injection.

21. The method of clause 19 wherein the triazolopyrimidinone, or the derivative thereof, or the pharmaceutically acceptable salt thereof, is administered in the form of eye drops.

22. The method of clause 19 wherein the triazolopyrimidinone, or the derivative thereof, or the pharmaceutically acceptable salt thereof, is administered in the form of an eye ointment.

23. The method of any one of clauses 11 to 18 wherein the triazolopyrimidinone, or the derivative thereof, or the pharmaceutically acceptable salt thereof, is administered by parenteral administration.

24. The method of any one of clauses 11 to 18 wherein the triazolopyrimidinone, or the derivative thereof, or the pharmaceutically acceptable salt thereof, is administered orally.

25. The method of any one of clauses 11 to 24 wherein the triazolopyrimidinone, or the derivative thereof, or the pharmaceutically acceptable salt thereof, is administered in a pharmaceutical composition and wherein the pharmaceutical composition further comprises a pharmaceutically acceptable carrier.

26. The method of any one of clauses 11 to 25 further comprising the step of administering an anti-VEGF agent to the patient.

27. The method of clause 26 wherein the anti-VEGF agent is selected from the group consisting of ranibizumab, bevacizumab, aflibercept, abicipar pegol, brolucizumab, faricimab, vorolanib, biosimilars to any of these VEGF agents, and combinations thereof.

28. The method of any one of clauses 11 to 20 wherein the triazolopyrimidinone, or the derivative thereof, or the pharmaceutically acceptable salt thereof, is administered using a single injection or multiple injections.

29. A method for treating a patient with malaria, the method comprising administering to the patient a triazolopyrimidinone, or a derivative thereof, or a pharmaceutically acceptable salt thereof.

30. The method of clause 29, wherein the triazolopyrimidinone, or the derivative thereof, or the pharmaceutically acceptable salt thereof, comprises a compound of the formula

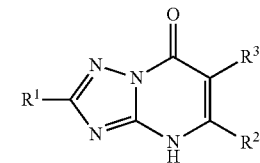

wherein
R$^1$ is $C_1$-$C_6$ alkyl, $C_2$-$C_6$ alkenyl, $C_2$-$C_6$ alkynyl, or $C_6$-$C_{10}$ aryl, or $C_1$-$C_6$ alkylNR$^4$R$^5$, wherein each hydrogen atom in $C_1$-$C_6$ alkyl, $C_2$-$C_6$ alkenyl, $C_2$-$C_6$ alkynyl, or $C_6$-$C_{10}$ aryl, is independently optionally substituted with fluoro, chloro, bromo, iodo, $C_1$-$C_6$ alkyl, —OC$_1$-$C_6$ alkyl, or $C_6$-$C_{10}$ aryl;

each of R$^2$ and R$^3$ is independently selected from the group consisting of H, $C_1$-$C_6$ alkyl, $C_2$-$C_6$ alkenyl, $C_2$-$C_6$ alkynyl, $C_6$-$C_{10}$ aryl, $C_1$-$C_6$ alkyl-$C_6$-$C_{10}$ aryl, and $C_1$-$C_6$ alkylNR$^6$R$^7$, provided that at least one of R$^2$ and R$^3$ is not H, wherein each hydrogen atom in $C_1$-$C_6$ alkyl, $C_2$-$C_6$ alkenyl, $C_2$-$C_6$ alkynyl, $C_6$-$C_{10}$ aryl, or $C_1$-$C_6$ alkyl-$C_6$-$C_{10}$ aryl, is independently optionally substituted with fluoro, chloro, bromo, iodo, —CO$_2$R$^1$, $C_1$-$C_6$ alkyl, —OC$_1$-$C_6$ alkyl, or $C_6$-$C_{10}$ aryl; or R$^2$ and R$^3$, when taken together with the carbon atoms to which they are attached, form a 5-7 membered carbocyclic ring;

each of $R^4$, $R^5$, $R^6$, or $R^7$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, and $C_1$-$C_6$ alkyl-$C_6$-$C_{10}$ aryl, wherein each hydrogen atom in $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, or $C_1$-$C_6$ alkyl-$C_6$-$C_{10}$ aryl is independently optionally substituted with fluoro, chloro, bromo, iodo, —$CO_2R^8$, $C_1$-$C_6$ alkyl, —$OC_1$-$C_6$ alkyl, —$OCF_3$, —$CF_3$ or $C_6$-$C_{10}$ aryl; and $R^8$ is H or $C_1$-$C_6$ alkyl.

31. The method of clause 29 or 30 wherein the disease is malaria and the method further comprises administering one or more of chloroquine (Aralen), quinine sulfate (Qualaquin), artemisinin, hydroxychloroquine (Plaquenil), mefloquine, a combination of atovaquone and proguanil (Malarone), and combinations thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIG. 6A shows the effects of representative screening hit compounds on HREC tube formation. FIG. 5B shows the effects of newly synthesized compounds, active against FECH, on HREC tube formation. *, p<0.05; , p<0.01; *, p<0.001 vs. DMSO control, ANOVA with Dunnett's post hoc test. Mean±SEM, n=6.

DETAILED DESCRIPTION OF ILLUSTRATIVE EMBODIMENTS

Figure 1:
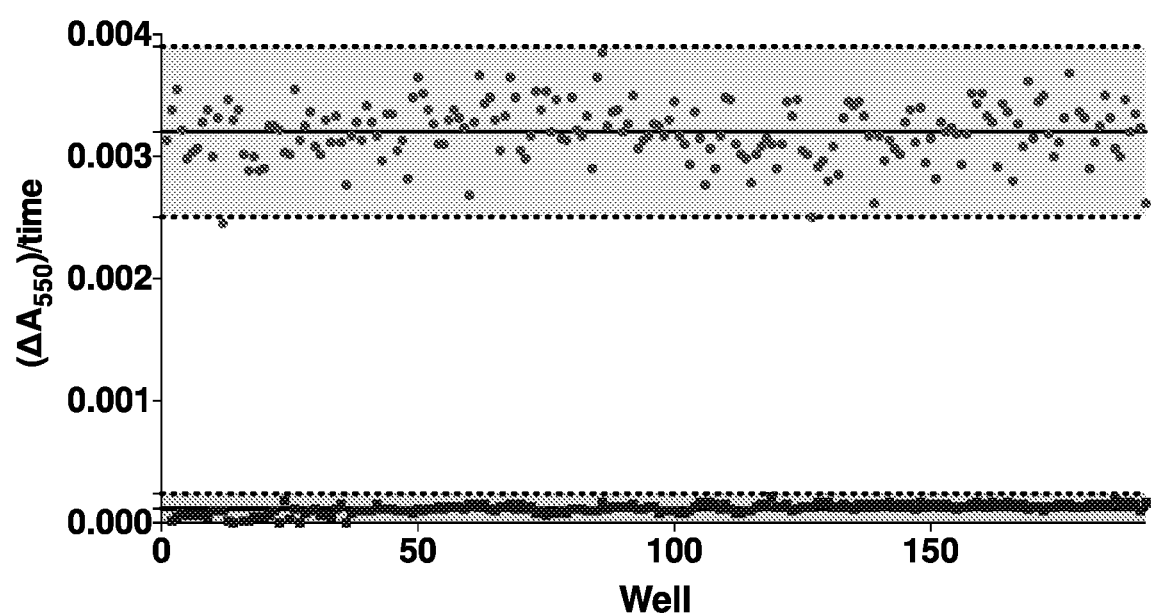
FIG. 1 depicts optimization of the FECH inhibitor screen as conducted in Example 1. Z' determination using 10 μM NMPP (squares) or vehicle (circles) indicates the signal-noise ratio for the FECH activity assay; 3 SD (dotted lines) around the mean (solid lines) for each treatment shown. Z' in this experiment was 0.73 (n=192 wells/treatment).

The present invention relates to a method of treatment of a patient with a ferrochelatase inhibitor, or a pharmaceutically acceptable salt thereof. Also, the invention relates to a method of treatment of a patient with a ferrochelatase inhibitor that is a triazolopyrimidinone, or a derivative thereof, or a pharmaceutically acceptable salt thereof.

Accordingly, in one aspect, the present disclosure is directed to a ferrochelatase inhibitor of the formula

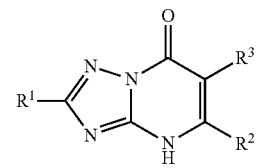

wherein $R^1$ is $C_6$-$C_{10}$ aryl or $C_1$-$C_6$ alkyNR$^4$R$^5$, wherein each hydrogen atom in $C_6$-$C_{10}$ aryl is independently optionally substituted with $C_1$-$C_6$ alkyl;

each of $R^2$ and $R^3$ is independently selected from the group consisting of H, $C_1$-$C_6$ alkyl, or $C_1$-$C_6$ alkylNR$^6$R$^7$, provided that at least one of $R^2$ and $R^3$ is not H, and when $R^1$ is $C_1$-$C_6$ alkyNR$^4$R$^5$, then $R^2$ is $C_3$-$C_6$ alkyl, and $R^3$ is H, wherein each hydrogen atom in $C_1$-$C_6$ alkyl is independently optionally substituted with fluoro, chloro, bromo, or iodo; or $R^2$ and $R^3$, when taken together with the carbon atoms to which they are attached, form a 5-7 membered carbocyclic ring;

$R^4$ is H;

$R^5$ is biphenyl, 4-tert-butylphenyl, 3-chloro-4-fluoro-phenyl, 3-fluoro-4-fluoro-phenyl, 4-(O—$C_1$-$C_6$ alkoxy)phenyl, 4-($OCF_3$)phenyl, 2-methylphenyl, 3-methylphenyl, or 4-methylphenyl, with the proviso that when $R^2$ and $R^3$, when taken together with the carbon atoms to which they are attached, form a 5-7 membered carbocyclic ring, then $R^5$ is 4-methylphenyl; and each of $R^6$ or $R^7$ is independently selected from the group consisting of H, $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl, wherein each hydrogen atom in $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl is independently optionally substituted with fluoro, chloro, bromo, iodo, $C_1$-$C_6$ alkyl, —$OC_1$-$C_6$ alkyl, —$OCF_3$, —$CF_3$ or $C_6$-$C_{10}$ aryl;

or a pharmaceutically acceptable salt thereof.

In some embodiments, $R^1$ is $C_6$-$C_{10}$ aryl, wherein each hydrogen atom in $C_6$-$C_{10}$ aryl is independently optionally substituted with $C_1$-$C_6$ alkyl. In some embodiments, $R^1$ is 4-tert-butylphenyl. In some embodiments, $R^2$ is $C_1$-$C_6$ alkyNR$^6$R$^7$, and $R^3$ is H. In some embodiments, $R^1$ is $C_1$-$C_6$ alkylNR$^4$R$^5$. In some embodiments, $R^2$ is n-propyl or iso-propyl, and $R^3$ is H. In some embodiments, $R^2$ and $R^3$, when taken together with the carbon atoms to which they are attached, form a 5-7 membered carbocyclic ring. In some embodiments, $R^2$ and $R^3$, when taken together with the carbon atoms to which they are attached, form a 5-membered carbocyclic ring.

In another embodiment, the present disclosure is directed to a ferrochelatase inhibitor of compound 2

Compound 2

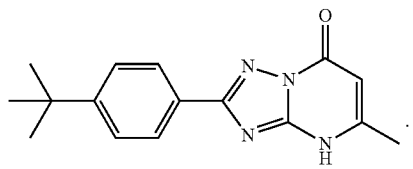

In another embodiment, the present disclosure is directed to a ferrochelatase inhibitor of compound 3

Compound 3

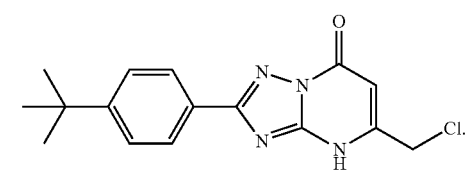

In another embodiment, the present disclosure is directed to a ferrochelatase inhibitor of compound 4a Compound 4a

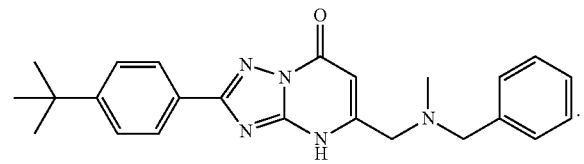

In yet another embodiment, the present disclosure is directed to a ferrochelatase inhibitor of compound 4b Compound 4b

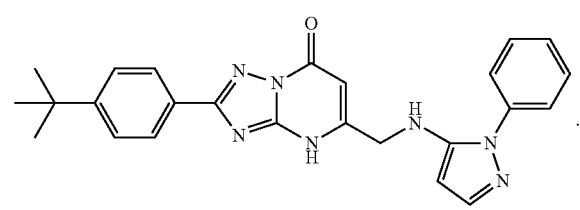

In another embodiment, the present disclosure is directed to a ferrochelatase inhibitor of compound 4c Compound 4c

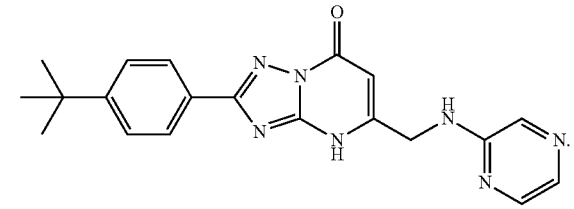

In another embodiment, the present disclosure is directed to a ferrochelatase inhibitor of compound 4d Compound 4d

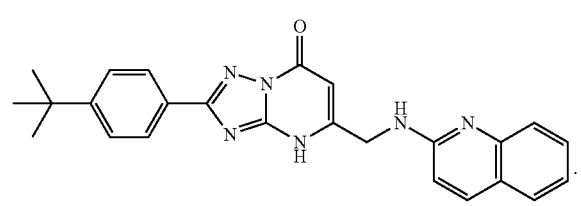

In yet another embodiment, the present disclosure is directed to a ferrochelatase inhibitor of compound 4e Compound 4e In another embodiment, the present disclosure is directed to a ferrochelatase inhibitor of compound 4f Compound 4f

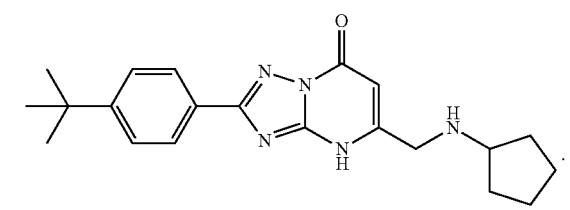

In yet another embodiment, the present disclosure is directed to a ferrochelatase inhibitor of compound 4g Compound 4g

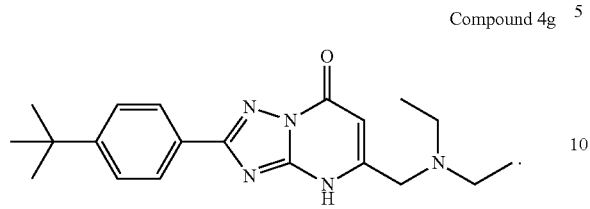

In yet another embodiment, the present disclosure is directed to a ferrochelatase inhibitor selected from the group consisting of

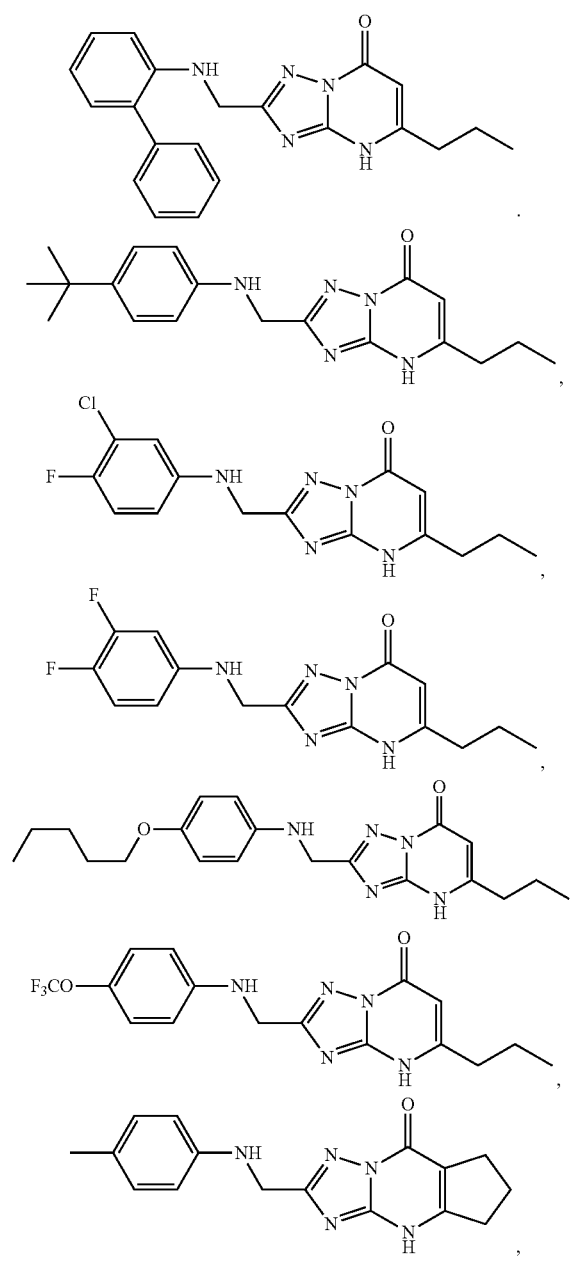

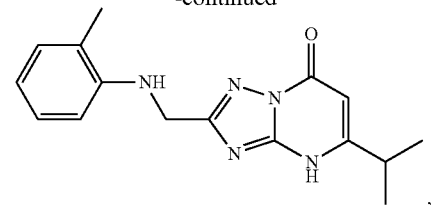

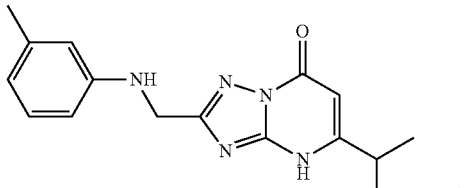

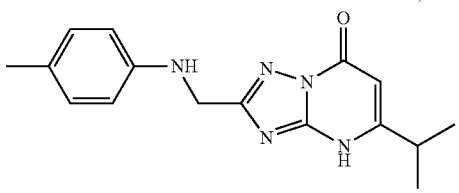

, and or a pharmaceutically acceptable salt thereof.

In another embodiment, a method for treating a patient with an angiogenesis-mediated disease is provided. The method comprises administering to the patient a triazolopyrimidinone, or a derivative thereof, or a pharmaceutically acceptable salt thereof.

In yet another embodiment, a method for treating a patient with malaria is provided. The method comprises administering to the patient a triazolopyrimidinone, or a derivative thereof, or a pharmaceutically acceptable salt thereof.

The various embodiments described in the numbered clauses below are applicable to any of the embodiments described in the "SUMMARY" section and the sections of the patent application titled "DETAILED DESCRIPTION OF ILLUSTRATIVE EMBODIMENTS" or "EXAMPLES" or in the "CLAIMS" appended to this application.

1. A compound of the formula

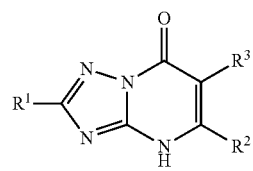

wherein $R^1$ is $C_6$-$C_{10}$ aryl or $C_1$-$C_6$ alkylN$R^4R^5$, wherein each hydrogen atom in $C_6$-$C_{10}$ aryl is independently optionally substituted with $C_1$-$C_6$ alkyl;

each of $R^2$ and $R^3$ is independently selected from the group consisting of H, $C_1$-$C_6$ alkyl, or $C_1$-$C_6$ alkylN$R^6R^7$, provided that at least one of $R^2$ and $R^3$ is not H, and when $R^1$ is $C_1$-$C_6$ alkylN$R^4R^5$, then $R^2$ is $C_3$-$C_6$ alkyl, and $R^3$ is H, wherein each hydrogen atom in $C_1$-$C_6$ alkyl is independently optionally substituted with fluoro, chloro, bromo, or iodo; or $R^2$ and $R^3$, when taken together with the carbon atoms to which they are attached, form a 5-7 membered carbocyclic ring;

R[4] is H;

R[5] is biphenyl, 4-tert-butylphenyl, 3-chloro-4-fluoro-phenyl, 3-fluoro-4-fluoro-phenyl, 4-(O—C$_1$-C$_6$ alkoxy) phenyl, 4-(OCF$_3$)phenyl, 2-methylphenyl, 3-methylphenyl, or 4-methylphenyl, with the proviso that when R[2] and R[3], when taken together with the carbon atoms to which they are attached, form a 5-7 membered carbocyclic ring, then R[5] is 4-methylphenyl; and each of R[6] or R[7] is independently selected from the group consisting of H, C$_1$-C$_6$ alkyl, C$_3$-C$_6$ cycloalkyl, 5- to 7-membered monocyclic heteroaryl, C$_6$-C$_{10}$ bicyclic heteroaryl, or C$_2$-C$_6$ alkyl-C$_6$-C$_{10}$ aryl, wherein each hydrogen atom in C$_1$-C$_6$ alkyl, C$_3$-C$_6$ cycloalkyl, 5- to 7-membered monocyclic heteroaryl, C$_6$-C$_{10}$ bicyclic heteroaryl, or C$_2$-C$_6$ alkyl-C$_6$-C$_{10}$ aryl is independently optionally substituted with fluoro, chloro, bromo, iodo, C$_1$-C$_6$ alkyl, —OC$_1$-C$_6$ alkyl, —OCF$_3$, —CF$_3$ or C$_6$-C$_{10}$ aryl;

or a pharmaceutically acceptable salt thereof.

2. The compound of clause 1, or a pharmaceutically acceptable salt thereof, wherein R[1] is C$_6$-C$_{10}$ aryl, wherein each hydrogen atom in C$_6$-C$_{10}$ aryl is independently optionally substituted with C$_1$-C$_6$ alkyl.

3. The compound of clause 1 or 2, or a pharmaceutically acceptable salt thereof, wherein R[1] is 4-tert-butylphenyl.

4. The compound of any of the preceding clauses, or a pharmaceutically acceptable salt thereof, wherein R[2] is C$_1$-C$_6$ alkylNR[6]R[7], and R[3] is H.

5. The compound of clause 1, or a pharmaceutically acceptable salt thereof, wherein R[1] is C$_1$-C$_6$ alkylNR[4]R[5].

6. The compound of clause 1 or 5, or a pharmaceutically acceptable salt thereof, wherein R[2] is n-propyl or iso-propyl, and R[3] is H.

7. The compound of clause 1, or a pharmaceutically acceptable salt thereof, wherein R[2] and R[3], when taken together with the carbon atoms to which they are attached, form a 5-7 membered carbocyclic ring.

8. The compound of clause 1 or 7, or a pharmaceutically acceptable salt thereof, wherein R[2] and R[3], when taken together with the carbon atoms to which they are attached, form a 5-membered carbocyclic ring.

9. A ferrochelatase inhibitor selected from the group consisting of

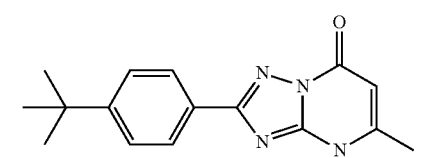

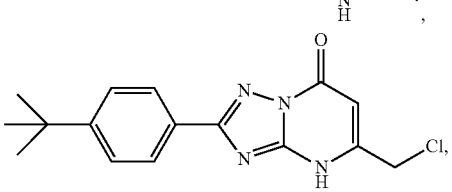

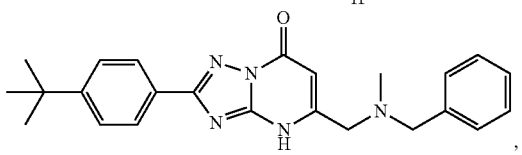

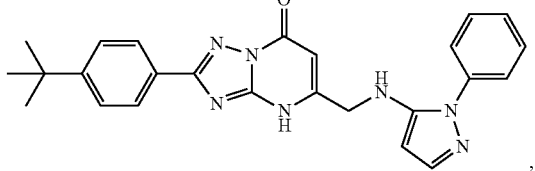

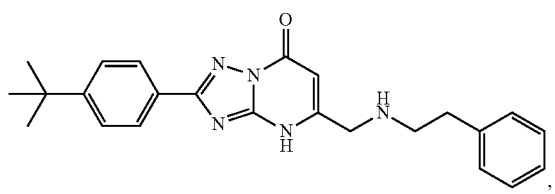

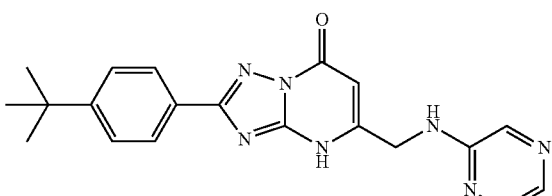

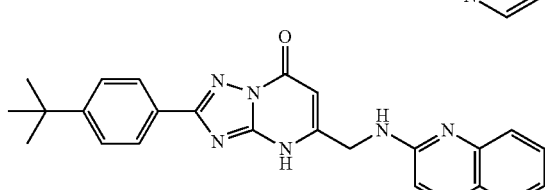

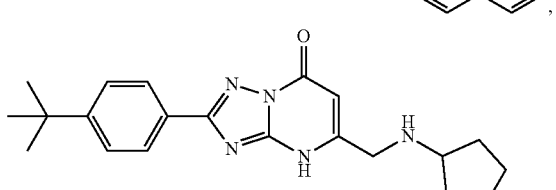, and

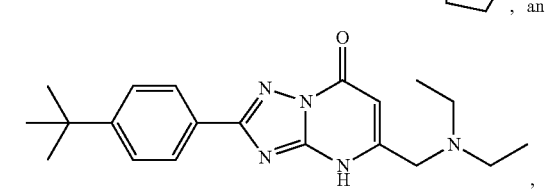, or a pharmaceutically acceptable salt thereof.

10. A ferrochelatase inhibitor selected from the group consisting of

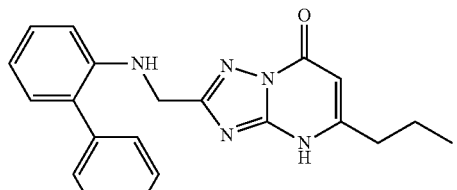

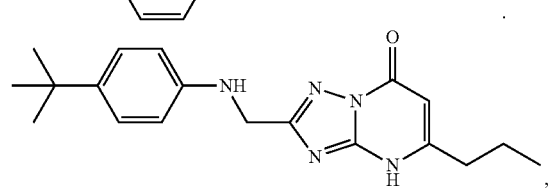,

21

-continued

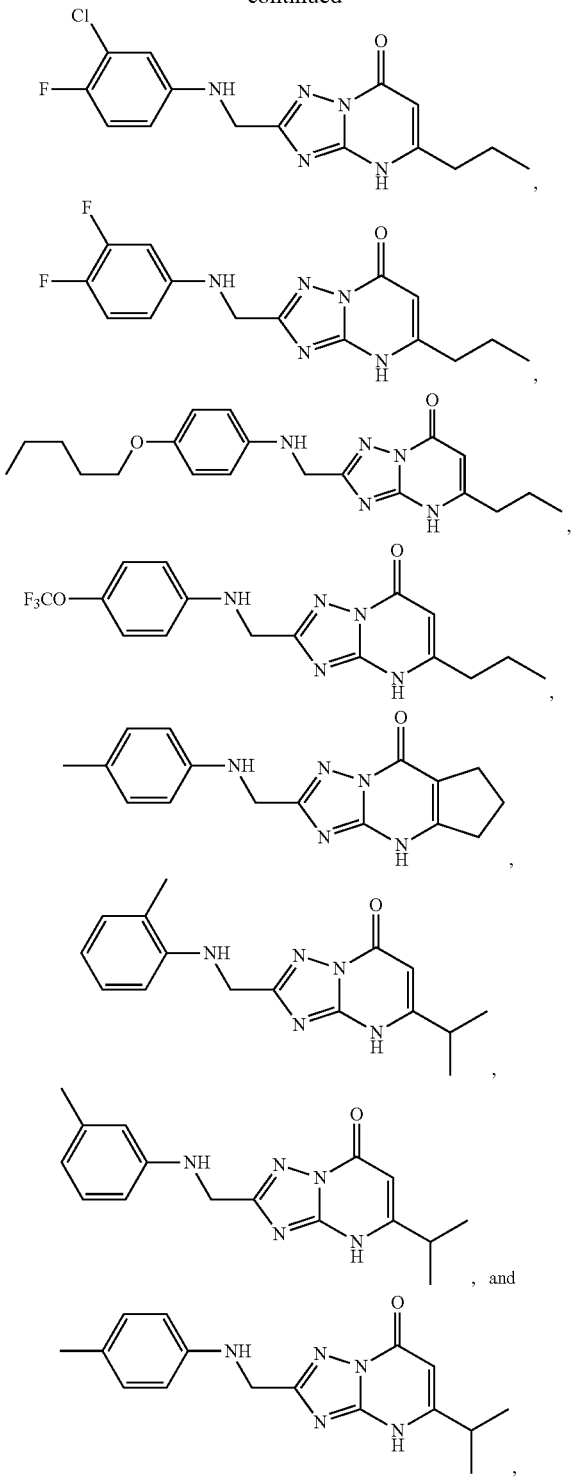

or a pharmaceutically acceptable salt thereof.

11. A method for treating a patient with an angiogenesis-mediated disease, the method comprising administering to the patient a triazolopyrimidinone, or a derivative thereof, or a pharmaceutically acceptable salt thereof.

12. The method of clause 11, wherein the triazolopyrimidinone, or the derivative thereof, or the pharmaceutically acceptable salt thereof, comprises a compound of the formula

22

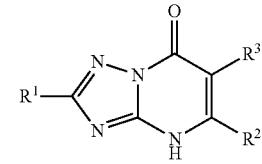

wherein $R^1$ is $C_1$-$C_6$ alkyl, $C_2$-$C_6$ alkenyl, $C_2$-$C_6$ alkynyl, or $C_6$-$C_{10}$ aryl, or $C_1$-$C_6$ alkylN$R^4R^5$, wherein each hydrogen atom in $C_1$-$C_6$ alkyl, $C_2$-$C_6$ alkenyl, $C_2$-$C_6$ alkynyl, or $C_6$-$C_{10}$ aryl, is independently optionally substituted with fluoro, chloro, bromo, iodo, $C_1$-$C_6$ alkyl, —O$C_1$-$C_6$ alkyl, or $C_6$-$C_{10}$ aryl;

each of $R^2$ and $R^3$ is independently selected from the group consisting of H, $C_1$-$C_6$ alkyl, $C_2$-$C_6$ alkenyl, $C_2$-$C_6$ alkynyl, $C_6$-$C_{10}$ aryl, $C_1$-$C_6$ alkyl-$C_6$-$C_{10}$ aryl, and $C_1$-$C_6$ alkyN$R^6R^7$, provided that at least one of $R^2$ and $R^3$ is not H, wherein each hydrogen atom in $C_1$-$C_6$ alkyl, $C_2$-$C_6$ alkenyl, $C_2$-$C_6$ alkynyl, $C_6$-$C_{10}$ aryl, or $C_1$-$C_6$ alkyl-$C_6$-$C_{10}$ aryl, is independently optionally substituted with fluoro, chloro, bromo, iodo, —$CO_2R^8$, $C_1$-$C_6$ alkyl, —O$C_1$-$C_6$ alkyl, or $C_6$-$C_{10}$ aryl; or $R^2$ and $R^3$, when taken together with the carbon atoms to which they are attached, form a 5-7 membered carbocyclic ring;

each of $R^4$, $R^5$, $R^6$, or $R^7$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, and $C_1$-$C_6$ alkyl-$C_6$-$C_{10}$ aryl, wherein each hydrogen atom in $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, or $C_1$-$C_6$ alkyl-$C_6$-$C_{10}$ aryl is independently optionally substituted with fluoro, chloro, bromo, iodo, —$CO_2R^8$, $C_1$-$C_6$ alkyl, —O$C_1$-$C_6$ alkyl, —$OCF_3$, —$CF_3$ or $C_6$-$C_{10}$ aryl; and $R^8$ is H or $C_1$-$C_6$ alkyl.

13. The method of any one of clauses 11 or 12, comprising administering to the patient the triazolopyrimidinone, or the derivative thereof, or the pharmaceutically acceptable salt thereof, to achieve an intravitreal concentration of from about 0.01 µM to about 1000 µM.

14. The method of any one of clauses 11 to 13, wherein the angiogenesis-mediated disease is selected from the group consisting of cancer, a disease involving neovascularization, retinopathy of prematurity, wet age-related macular degeneration, hypertensive retinopathy, central retinal vein occlusion, branch retinal vein occlusion, neovascular glaucoma, retinoblastoma, diabetic macular edema, and proliferative diabetic retinopathy.

15. The method of any one of clauses 11 to 14 further comprising administering one or more of N-methylprotoporphyrin (NMPP) or an analog thereof, griseofulvin or an analog thereof, antisense RNA targeting ferrochelatase RNA, an agent for RNA silencing or RNA interference (RNAi) targeting ferrochelatase RNA, an agent for CRISPR/Cas9-mediated or Zinc-finger nuclease-mediated genetic ablation of ferrochelatase (FECH) DNA, an agent for anti-VEGF therapy, and combinations thereof.

16. The method of any one of clauses 11 to 15, comprising administering to the patient the triazolopyrimidinone, or the derivative thereof, or the pharmaceutically acceptable salt thereof, to achieve an intravitreal concentration of from about 0.01 μM to about 500 μM.

17. The method of clause 14, wherein the disease is cancer and the cancer is selected from the group consisting of glioma, breast cancer, bladder cancer, colon cancer, and combinations thereof.

18. The method of clause 17 further comprising treating the patient with photodynamic therapy (PDT).

19. The method of any one of clauses 11 to 16 wherein the triazolopyrimidinone, or the derivative thereof, or the pharmaceutically acceptable salt thereof, is used to treat an ocular disease and is administered directly into the eye.

20. The method of clause 19 wherein the triazolopyrimidinone, or the derivative thereof, or the pharmaceutically acceptable salt thereof, is administered by injection.

21. The method of clause 19 wherein the triazolopyrimidinone, or the derivative thereof, or the pharmaceutically acceptable salt thereof, is administered in the form of eye drops.

22. The method of clause 19 wherein the triazolopyrimidinone, or the derivative thereof, or the pharmaceutically acceptable salt thereof, is administered in the form of an eye ointment.

23. The method of any one of clauses 11 to 18 wherein the triazolopyrimidinone, or the derivative thereof, or the pharmaceutically acceptable salt thereof, is administered by parenteral administration.

24. The method of any one of clauses 11 to 18 wherein the triazolopyrimidinone, or the derivative thereof, or the pharmaceutically acceptable salt thereof, is administered orally.

25. The method of any one of clauses 11 to 24 wherein the triazolopyrimidinone, or the derivative thereof, or the pharmaceutically acceptable salt thereof, is administered in a pharmaceutical composition and wherein the pharmaceutical composition further comprises a pharmaceutically acceptable carrier.

26. The method of any one of clauses 11 to 25 further comprising the step of administering an anti-VEGF agent to the patient.

27. The method of clause 26 wherein the anti-VEGF agent is selected from the group consisting of ranibizumab, bevacizumab, aflibercept, abicipar pegol, brolucizumab, faricimab, vorolanib, biosimilars to any of these VEGF agents, and combinations thereof.

28. The method of any one of clauses 11 to 20 wherein the triazolopyrimidinone, or the derivative thereof, or the pharmaceutically acceptable salt thereof, is administered using a single injection or multiple injections.

29. A method for treating a patient with malaria, the method comprising administering to the patient a triazolopyrimidinone, or a derivative thereof, or a pharmaceutically acceptable salt thereof.

30. The method of clause 29, wherein the triazolopyrimidinone, or the derivative thereof, or the pharmaceutically acceptable salt thereof, comprises a compound of the formula

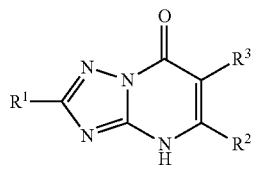

wherein
R$^1$ is C$_1$-C$_6$ alkyl, C$_2$-C$_6$ alkenyl, C$_2$-C$_6$ alkynyl, or C$_6$-C$_{10}$ aryl, or C$_1$-C$_6$ alkylNR$^4$R$^5$, wherein each hydrogen atom in C$_1$-C$_6$ alkyl, C$_2$-C$_6$ alkenyl, C$_2$-C$_6$ alkynyl, or C$_6$-C$_{10}$ aryl, is independently optionally substituted with fluoro, chloro, bromo, iodo, C$_1$-C$_6$ alkyl, —OC$_1$-C$_6$ alkyl, or C$_6$-C$_{10}$ aryl;

wherein
R$^1$ is C$_1$-C$_6$ alkyl, C$_2$-C$_6$ alkenyl, C$_2$-C$_6$ alkynyl, or C$_6$-C$_{10}$ aryl, or C$_1$-C$_6$ alkylNR$^4$R$^5$, wherein each hydrogen atom in C$_1$-C$_6$ alkyl, C$_2$-C$_6$ alkenyl, C$_2$-C$_6$ alkynyl, or C$_6$-C$_{10}$ aryl, is independently optionally substituted with fluoro, chloro, bromo, iodo, C$_1$-C$_6$ alkyl, —OC$_1$-C$_6$ alkyl, or C$_6$-C$_{10}$ aryl;

each of R$^2$ and R$^3$ is independently selected from the group consisting of H, C$_1$-C$_6$ alkyl, C$_2$-C$_6$ alkenyl, C$_2$-C$_6$ alkynyl, C$_6$-C$_{10}$ aryl, C$_1$-C$_6$ alkyl-C$_6$-C$_{10}$ aryl, and C$_1$-C$_6$ alkylNR$^6$R$^7$, provided that at least one of R$^2$ and R$^3$ is not H, wherein each hydrogen atom in C$_1$-C$_6$ alkyl, C$_2$-C$_6$ alkenyl, C$_2$-C$_6$ alkynyl, C$_6$-C$_{10}$ aryl, or C$_1$-C$_6$ alkyl-C$_6$-C$_{10}$ aryl, is independently optionally substituted with fluoro, chloro, bromo, iodo, —CO$_2$R$^1$, C$_1$-C$_6$ alkyl, —OC$_1$-C$_6$ alkyl, or C$_6$-C$_{10}$ aryl; or R$^2$ and R$^3$, when taken together with the carbon atoms to which they are attached, form a 5-7 membered carbocyclic ring;

each of R$^4$, R$^5$, R$^6$, or R$^7$ is independently selected from the group consisting of H, C$_1$-C$_6$ alkyl, C$_2$-C$_6$ alkenyl, C$_2$-C$_6$ alkynyl, C$_3$-C$_6$ cycloalkyl, 5- to 7-membered monocyclic heteroaryl, C$_6$-C$_{10}$ bicyclic heteroaryl, C$_6$-C$_{10}$ aryl, and C$_1$-C$_6$ alkyl-C$_6$-C$_{10}$ aryl, wherein each hydrogen atom in C$_1$-C$_6$ alkyl, C$_2$-C$_6$ alkenyl, C$_2$-C$_6$ alkynyl, C$_3$-C$_6$ cycloalkyl, 5- to 7-membered monocyclic heteroaryl, C$_6$-C$_{10}$ bicyclic heteroaryl, C$_6$-C$_{10}$ aryl, or C$_1$-C$_6$ alkyl-C$_6$-C$_{10}$ aryl is independently optionally substituted with fluoro, chloro, bromo, iodo, —CO$_2$R$^8$, C$_1$-C$_6$ alkyl, —OC$_1$-C$_6$ alkyl, —OCF$_3$, —CF$_3$ or C$_6$-C$_{10}$ aryl; and R$^8$ is H or C$_1$-C$_6$ alkyl.

31. The method of clause 29 or 30 wherein the disease is malaria and the method further comprises administering one or more of chloroquine (Aralen), quinine sulfate (Qualaquin), artemisinin, hydroxychloroquine (Plaquenil), mefloquine, a combination of atovaquone and proguanil (Malarone), and combinations thereof.

The present disclosure is generally related to ferrochelatase inhibitors, or derivatives thereof, or pharmaceutically acceptable salts thereof, and methods of inhibiting ferrochelatase as an antiangiogenic therapy or a therapy for malaria using the inhibitors. Particularly, it has now been found that triazolopyrimidinones, and derivatives thereof, and pharmaceutically acceptable salts thereof, can inhibit ferrochelatase.

In some embodiments, suitable triazolopyrimidinones for use in connection with the methods provided herein, and derivatives thereof, for inhibiting ferrochelatase include those having

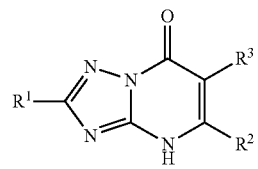

each of $R^2$ and $R^3$ is independently selected from the group consisting of H, $C_1$-$C_6$ alkyl, $C_2$-$C_6$ alkenyl, $C_2$-$C_6$ alkynyl, $C_6$-$C_{10}$ aryl, $C_1$-$C_6$ alkyl-$C_6$-$C_{10}$ aryl, and $C_1$-$C_6$ alkylNR$^6$R$^7$, provided that at least one of $R^2$ and $R^3$ is not H, wherein each hydrogen atom in $C_1$-$C_6$ alkyl, $C_2$-$C_6$ alkenyl, $C_2$-$C_6$ alkynyl, $C_6$-$C_{10}$ aryl, or $C_1$-$C_6$ alkyl-$C_6$-$C_{10}$ aryl, is independently optionally substituted with fluoro, chloro, bromo, iodo, —$CO_2R^8$, $C_1$-$C_6$ alkyl, —$OC_1$-$C_6$ alkyl, or $C_6$-$C_{10}$ aryl; or $R^2$ and $R^3$, when taken together with the carbon atoms to which they are attached, form a 5-7 membered carbocyclic ring;

each of $R^4$, $R^5$, $R^6$, or $R^7$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, and $C_1$-$C_6$ alkyl-$C_6$-$C_{10}$ aryl, wherein each hydrogen atom in $C_1$-$C_6$ alkyl, $C_2$-$C_6$ alkenyl, $C_2$-$C_6$ alkynyl, $C_3$-$C_6$ cycloalkyl, 5- to 7-membered monocyclic heteroaryl, $C_6$-$C_{10}$ bicyclic heteroaryl, $C_6$-$C_{10}$ aryl, or $C_1$-$C_6$ alkyl-$C_6$-$C_{10}$ aryl is independently optionally substituted with fluoro, chloro, bromo, iodo, —$CO_2R^8$, $C_1$-$C_6$ alkyl, —$OC_1$-$C_6$ alkyl, —$OCF_3$, —$CF_3$ or $C_6$-$C_{10}$ aryl; and $R^8$ is H or $C_1$-$C_6$ alkyl.

In some embodiments, suitable triazolopyrimidinones for us in connection with the methods provided herein, and derivatives thereof, for inhibiting ferrochelatase include those having the general formula

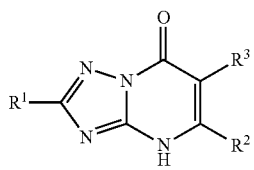

wherein
$R^1$ is $C_6$-$C_{10}$ aryl or $C_1$-$C_6$ alkylNR$^4$R$^5$, wherein each hydrogen atom in $C_6$-$C_{10}$ aryl is independently optionally substituted with $C_1$-$C_6$ alkyl;

each of $R^2$ and $R^3$ is independently selected from the group consisting of H, $C_1$-$C_6$ alkyl, or $C_1$-$C_6$ alkylNR$^6$R$^7$, provided that at least one of $R^2$ and $R^3$ is not H, and when $R^1$ is $C_1$-$C_6$ alkylNR$^4$R$^5$, then $R^2$ is $C_3$-$C_6$ alkyl, and $R^3$ is H, wherein each hydrogen atom in $C_1$-$C_6$ alkyl is independently optionally substituted with fluoro, chloro, bromo, or iodo; or $R^2$ and $R^3$, when taken together with the carbon atoms to which they are attached, form a 5-7 membered carbocyclic ring;

each of $R^4$ is H;

$R^5$ is biphenyl, 4-tert-butylphenyl, 3-chloro-4-fluoro-phenyl, 3-fluoro-4-fluoro-phenyl, 4-(O—$C_1$-$C_6$ alkoxy) phenyl, 4-(OCF$_3$)phenyl, 2-methylphenyl, 3-methylphenyl, or 4-methylphenyl, with the proviso that when $R^2$ and $R^3$, when taken together with the carbon atoms to which they are attached, form a 5-7 membered carbocyclic ring, then $R^5$ is 4-methylphenyl; and each of $R^6$ or $R^7$ is independently selected from the group consisting of H, $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl, wherein each hydrogen atom in $C_1$-$C_6$ alkyl, $C_3$-$C_6$ cycloalkyl, 5- to 7-membered monocyclic heteroaryl, $C_6$-$C_{10}$ bicyclic heteroaryl, or $C_2$-$C_6$ alkyl-$C_6$-$C_{10}$ aryl is independently optionally substituted with fluoro, chloro, bromo, iodo, $C_1$-$C_6$ alkyl, —$OC_1$-$C_6$ alkyl, —$OCF_3$, —$CF_3$ or $C_6$-$C_{10}$ aryl;

or a pharmaceutically acceptable salt thereof.

In some embodiments, suitable triazolopyrimidinones for use in connection with the methods provided herein, and derivatives thereof, for inhibiting ferrochelatase include those having the general formula

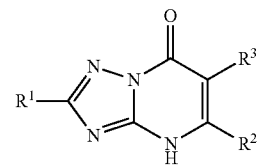

wherein $R^1$, $R^2$ and $R^3$ are independently selected from the group consisting of alkyl, substituted alkyl, alkoxy, substituted alkoxy, aryl, substituted aryl, heteroaryl, substituted heteroaryl, aryl carbonyloxy, substituted aryl carbonyloxy, halogen, amino, nitro, hydrocarbyl, and substituted hydrocarbyl.

Particularly suitable triazolopyrimidinones and derivatives for use in connection with the methods described herein include, for example, those set forth in Tables 1 and 2 in the Examples. Further, particularly suitable triazolopyrimidinones and derivatives for use in connection with the methods described herein include:

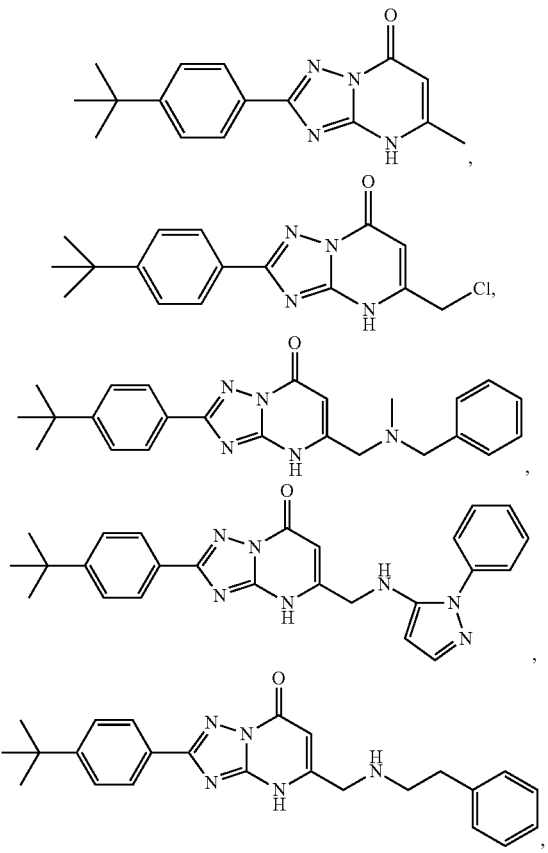

-continued
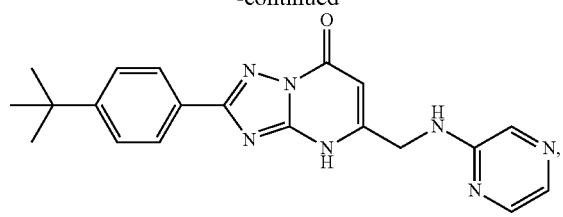
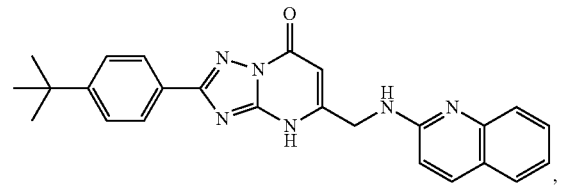
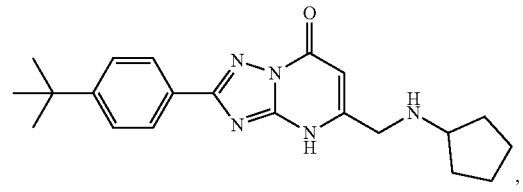
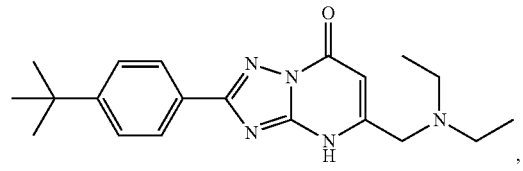
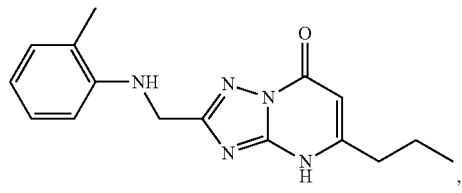
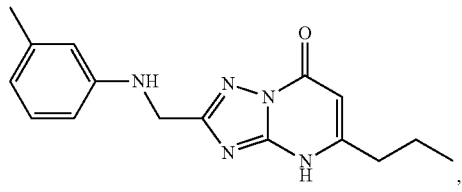
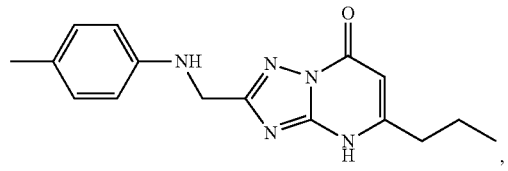
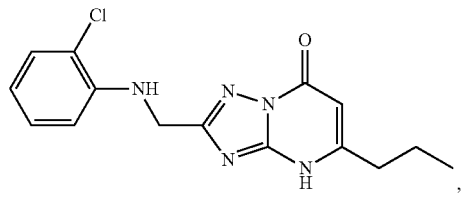
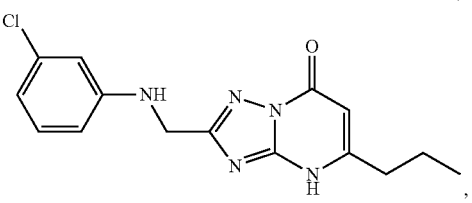
-continued
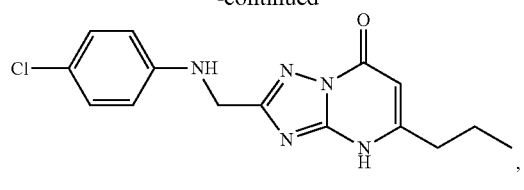
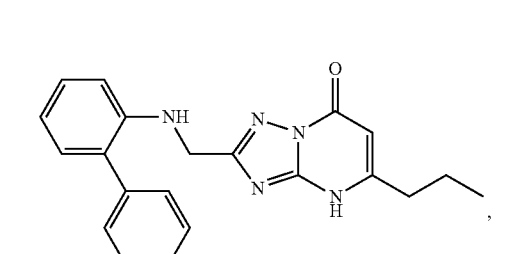
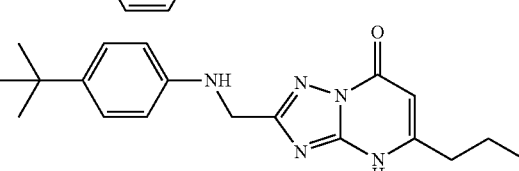
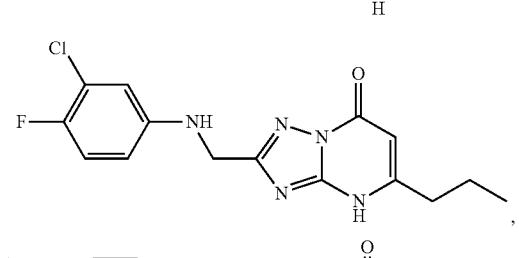
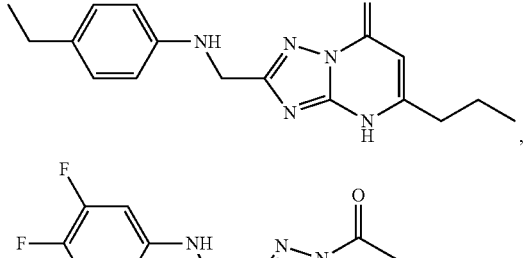
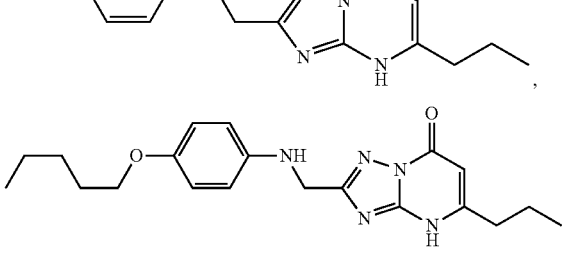
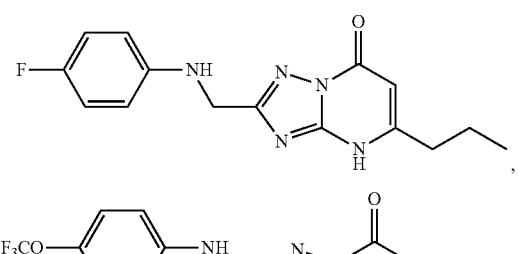
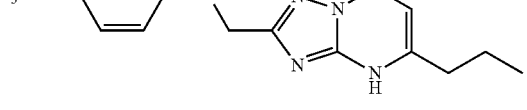

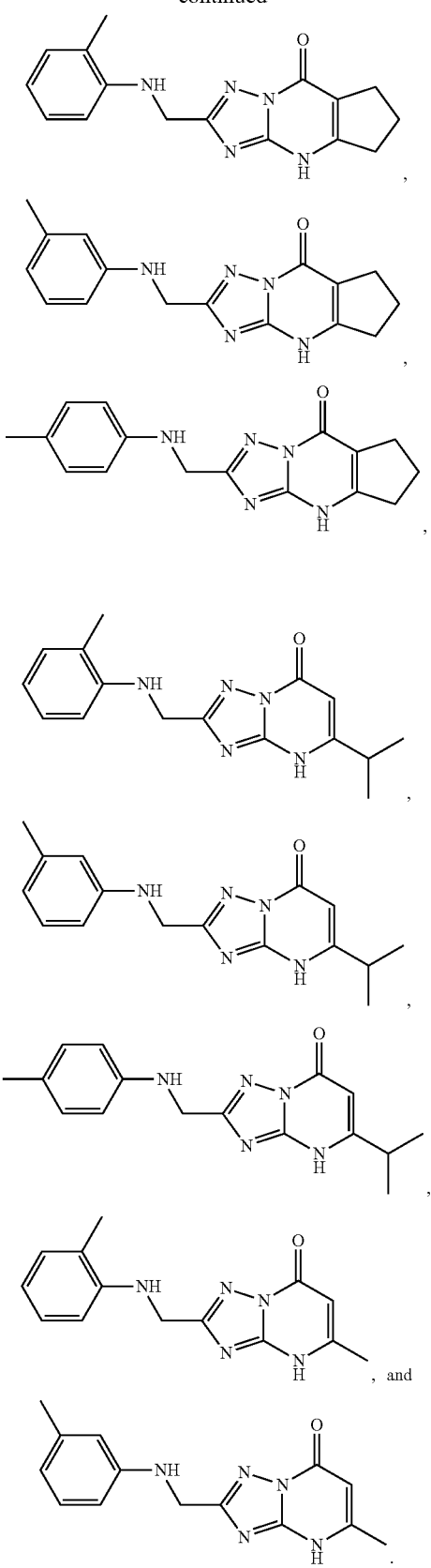
In some embodiments, suitable triazolopyrimidinones, and derivatives thereof, for inhibiting ferrochelatase include
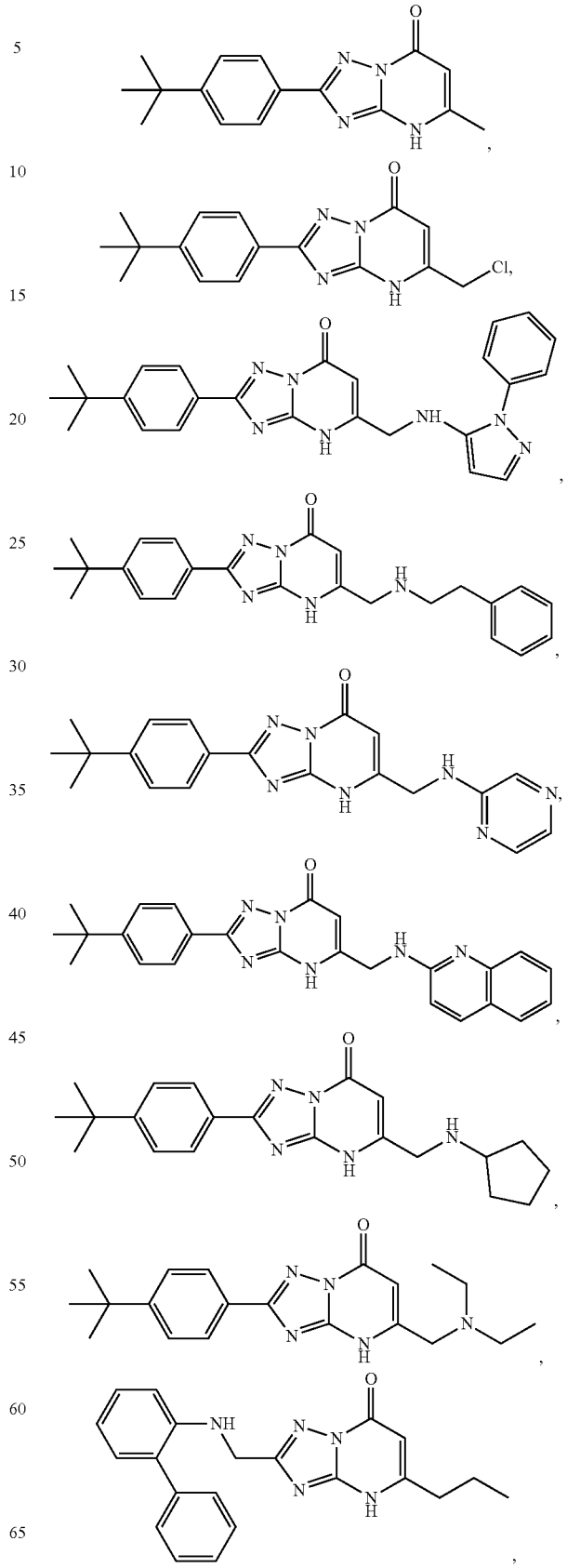

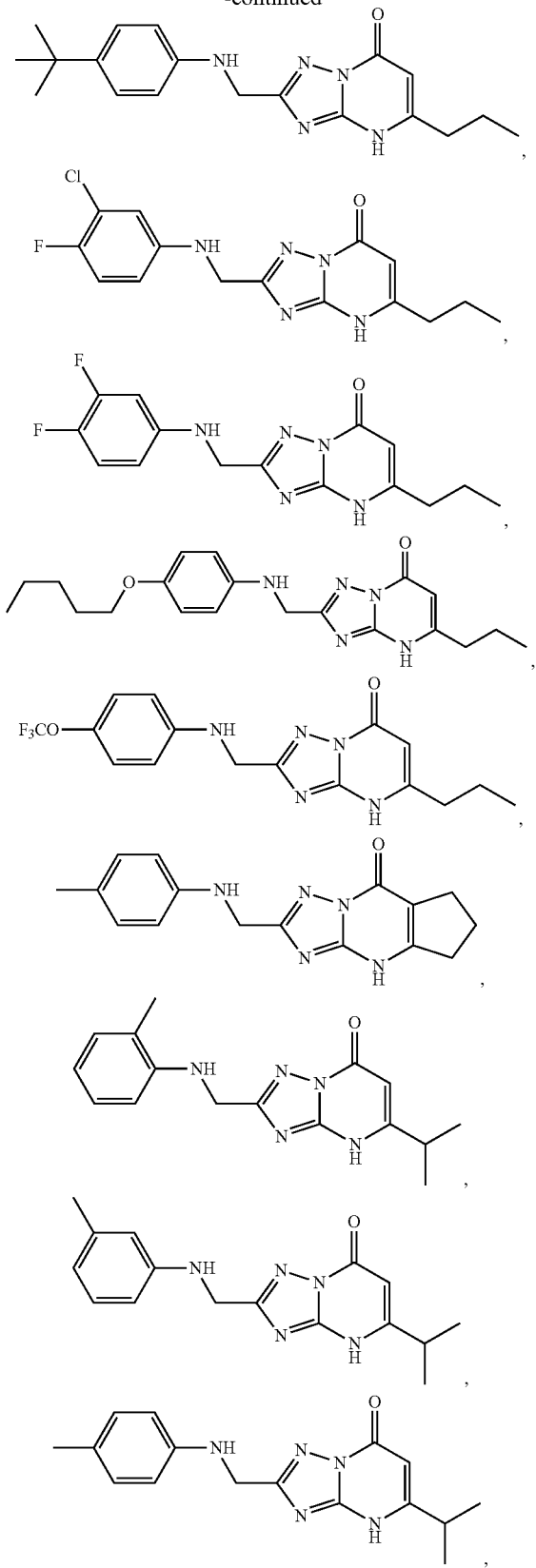

In one embodiment, the present disclosure is directed to the use of the above triazolopyrimidinones, and derivatives thereof, or pharmaceutically acceptable salts thereof, alone or in compositions, to inhibit ferrochelatase. Particularly, it has now been shown that angiogenesis is inhibited by blocking ferrochelatase. Inhibition of ferrochelatase have been shown to block ocular neovascularization, thereby treating neovascular eye diseases such as retinopathy of prematurity (ROP), proliferative diabetic retinopathy (PDR), hypertensive retinopathy, central retinal vein occlusion, branch retinal vein occlusion, neovascular glaucoma, retinoblastoma, diabetic macular edema, pathological myopia, occlusive vasculitis, polypoidal choroidal vasculopathy, uveitic macular edema, corneal neovascularization, retinal neovascularization, ocular histoplasmosis, and wet age-related macular degeneration (AMD), as well as treating cancers. In another aspect, inhibition of ferrochelatase has shown promise for treating malaria.

Ferrochelatase (FECH) is a nuclear-encoded, mitochondrial inner membrane-associated enzyme responsible for the final step of heme biosynthesis. FECH catalyzes the insertion of ferrous ion ($Fe^{2+}$) into the center of protoporphyrin IX (PPIX) to complete the formation of heme. $Fe^{2+}$ is supplied by the inner membrane iron transporter mitoferrin stabilized by the channel ABCB10, while PPIX is produced by a cascade of porphyrin synthetic enzymes ending with protoporphyrinogen oxidase, which likely complexes with FECH to deliver PPIX. FECH-synthesized heme is then utilized as a cofactor by hemoproteins in the cell, including proteins important for angiogenesis such as nitric oxidase synthases (NOSs), mitochondrial Complex IV, hemoxygenase 1 (HO-1), and others.

In one embodiment, a method for treating a patient with an angiogenesis-mediated disease is provided. The method comprises administering to the patient a triazolopyrimidinone, or a derivative thereof, or a pharmaceutically acceptable salt thereof.

As described herein, a "patient" can be a human or, in the case of veterinary applications, the patient can be a laboratory, an agricultural, a domestic, or a wild animal. In various aspects, the patient can be a laboratory animal such as a rodent (e.g., mouse, rat, hamster, etc.), a rabbit, a monkey, a chimpanzee, a domestic animal such as a dog, a cat, or a rabbit, an agricultural animal such as a cow, a horse, a pig, a sheep, a goat, or a wild animal in captivity such as a bear, a panda, a lion, a tiger, a leopard, an elephant, a zebra, a giraffe, a gorilla, a dolphin, or a whale.

Exemplary ferrochelatase inhibitors that can be administered in addition to the triazolopyrimidinone, or the derivative thereof, or the pharmaceutically acceptable salt thereof, include N-methylprotoporphyrin (NMPP), or analogs thereof, and the FDA-approved antifungal drug griseofulvin, or analogs thereof, and combinations thereof. Examples of analogs of griseofulvin are described in De Matteis, et al., Labelling in vivo and chirality of griseofulvin-derived N-alkylated protoporphyrins, *Biochem J.*, vol. 280 (Pt 3), pp. 813-816 (1991), incorporated herein by reference. Examples of analogs of NMPP are described in McCluskey, et al., Differential inhibition of hepatic ferrochelatase by regioisomers of N-butyl-, N-pentyl-, N-hexyl-, and N-isobutylprotoporphyrin IX, *Molecular Pharmacology*, vol. 34, pp. 80-86 (1988), incorporated herein by reference. Other exemplary ferrochelatase inhibitors that can be administered in addition to the triazolopyrimidinone, or the derivative thereof, or the pharmaceutically acceptable salt thereof, include, but are not limited to, antisense RNA targeting ferrochelatase RNA, an agent for RNA silencing or RNA interference (RNAi) targeting ferrochelatase RNA, an agent for CRISPR/Cas9-mediated genetic ablation of ferrochelatase (FECH) DNA, an agent for Zinc-finger nuclease-mediated genetic ablation of ferrochelatase (FECH) DNA, and combinations thereof, or, pharmaceutically acceptable salts thereof for the small molecule inhibitors described in this paragraph.

In one embodiment, the amount of the triazolopyrimidinone, or the derivative thereof, or the pharmaceutically acceptable salt thereof, to be administered to the patient can vary significantly depending on the disease being treated, age and weight of the patient, severity of the disease, the route of administration, and the tissue distribution. In one aspect, the amount to be administered to a patient can be based on body surface area or mass. A suitable dosage can be readily determined by one skilled in the art such as, for example, a physician, a veterinarian, a scientist, and other medical and research professionals.

In various embodiments, a suitable dosage of the triazolopyrimidinone, or the derivative thereof, or the pharmaceutically acceptable salt thereof, may achieve a final intravitreal concentration of from about 0.01 µM to about 10 µM, about 0.01 µM to about 20 µM, about 0.01 µM to about 30 µM, about 0.01 µM to about 40 µM, about 0.01 µM to about 50 µM, about 0.01 µM to about 60 µM, about 0.01 µM to about 70 µM, about 0.01 µM to about 80 µM, about 0.01 µM to about 90 µM, about 0.01 µM to about 100 µM, about 0.01 µM to about 150 µM, about 0.01 µM to about 200 µM, about 0.01 µM to about 300 µM, about 0.01 µM to about 400 µM, about 0.01 µM to about 500 µM, about 0.01 µM to about 1000 µM, about 0.5 µM to about 10 µM, about 0.5 µM to about 20 µM, about 0.5 µM to about 30 µM, about 0.5 µM to about 40 µM, about 0.5 µM to about 50 µM, about 0.5 µM to about 60 µM, about 0.5 µM to about 70 µM, about 0.5 µM to about 80 µM, about 0.5 µM to about 90 µM, about 0.5 µM to about 100 µM, about 0.5 µM to about 150 µM, about 0.5 µM to about 200 µM, about 0.5 µM to about 300 µM, about 0.5 µM to about 400 µM, about 0.5 µM to about 500 µM, about 0.5 µM to about 1000 µM, from about 0.75 µM to about 5 µM, from about 0.75 µM to about 4 µM, from about 0.75 µM to about 3 µM, from about 0.75 µM to about 2 µM, from about 0.75 µM to about 1.5 µM, from about 0.75 µM to about 1.25 µM, from about 0.25 µM to about 500 µM, from about 0.25 µM to about 400 µM, from about 0.25 µM to about 300 µM, from about 0.25 µM to about 200 µM, from about 0.25 µM to about 100 µM, from about 0.25 µM to about 75 µM, from about 0.25 µM to about 50 µM, from about 0.25 µM to about 25 µM, from about 25 µM to about 250 µM, from about 25 µM to about 200 µM, from about 25 µM to about 150 µM, from about 25 µM to about 150 µM, from about 25 µM to about 50 µM, from about 50 µM to about 100 µM, from about 50 µM to about 200 µM, from about 50 µM to about 300 µM, from about 50 µM to about 400 µM, from about 50 µM to about 500 µM, or about 50 µM to about 1000 µM.

In various embodiments, amounts to be administered to the patient for parenteral administration can range, for example, from about 0.05 mg to about 1000 mg, from about 0.05 mg to about 500 mg, from about 0.05 mg to about 400 mg, from about 0.05 mg to about 300 mg, from about 0.05 mg to about 200 mg from about 0.05 mg to about 100 mg, from about 0.05 mg to about 50 mg, from about 0.05 mg to about 30 mg, 0.05 mg to about 25.0 mg, about 0.05 mg to about 20.0 mg, about 0.05 mg to about 15.0 mg, about 0.05 mg to about 10.0 mg, about 0.05 mg to about 9.0 mg, about 0.05 mg to about 8.0 mg, about 0.05 mg to about 7.0 mg, about 0.05 mg to about 6.0 mg, about 0.05 mg to about 5.0 mg, about 0.05 mg to about 4.0 mg, about 0.05 mg to about 3.0 mg, about 0.05 mg to about 2.0 mg, about 0.05 mg to about 1.0 mg, about 0.05 mg to about 0.5 mg, about 0.05 mg to about 0.4 mg, about 0.05 mg to about 0.3 mg, about 0.05 mg to about 0.2 mg, about 0.05 mg to about 0.1 mg, about 0.01 mg to about 2 mg, about 0.3 mg to about 10 mg, about 0.1 mg to about 20 mg, or about 0.8 to about 3 mg. One of skill in the art will readily appreciate that the dose may vary within the various ranges provided above, and may be at the physician's discretion.

In one embodiment, the triazolopyrimidinone, or the derivative thereof, can be in the form of a "pharmaceutically acceptable salt". As used herein, the term "pharmaceutically acceptable salt" refers to those salts whose counter ions may be used in pharmaceuticals. In various embodiments, such salts include, but are not limited to 1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or 2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like. Pharmaceutically acceptable salts are well-known to those skilled in the art, and any such pharmaceutically acceptable salt is contemplated in connection with the embodiments described herein.

In various embodiments, suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

In various embodiments, suitable base salts are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one illustrative aspect, the triazolopyrimidinone, or the derivative thereof, or the pharmaceutically acceptable salt thereof, described herein may contain one or more chiral centers, or may otherwise be capable of existing as multiple stereoisomers. In one aspect, the triazolopyrimidinone, or the derivative thereof, or the pharmaceutically acceptable salt thereof, may be capable of existing as geometric isomers. Accordingly, various embodiments may include pure geometric isomers or mixtures of geometric isomers.

In some aspects, the triazolopyrimidinone, or the derivative thereof, or the pharmaceutically acceptable salt thereof, described herein may exist in unsolvated forms as well as solvated forms, including hydrated forms. In general, the solvated forms are equivalent to unsolvated forms and are encompassed within the scope of the present invention.

In one embodiment, the triazolopyrimidinone, or the derivative thereof, or the pharmaceutically acceptable salt thereof, described herein can be administered to the patient using any suitable method known in the art. As described herein, the term "administering" or "administered" includes all means of introducing the triazolopyrimidinone, or the derivative thereof, or the pharmaceutically acceptable salt thereof, to the patient, including, but not limited to, oral, intravenous, intramuscular, subcutaneous, intravitreal, intraocular, topical, and the like. In one aspect, the triazolopyrimidinone, or the derivative thereof, or the pharmaceutically acceptable salt thereof, described herein may be administered in a unit dosage form and/or in formulations containing conventional nontoxic pharmaceutically acceptable carriers, adjuvants, and vehicles.

In various embodiments, the triazolopyrimidinone, or the derivative thereof, or the pharmaceutically acceptable salt thereof, can be administered directly into the eye, for example, by single or multiple administrations. In other embodiments, the triazolopyrimidinone, or the derivative thereof, or the pharmaceutically acceptable salt thereof, can be administered by injection, in the form of eye drops, in the form of an eye ointment, by parenteral administration, or the triazolopyrimidinone, or the derivative thereof, or the pharmaceutically acceptable salt thereof, can be administered orally, such as by using tablets, capsules, granules, powders, or syrups, for example, or by any other suitable means of administration.

In one aspect, the triazolopyrimidinone, or the derivative thereof, or the pharmaceutically acceptable salt thereof, may be administered directly into the blood stream by parenteral administration. In various embodiments, suitable routes for such parenteral administration include intravenous, intraarterial, intraperitoneal, intramuscular, and subcutaneous delivery. In one embodiment, means for parenteral administration include needle (including microneedle) injectors, needle-free injectors and infusion techniques.

In one illustrative embodiment, the triazolopyrimidinone, or the derivative thereof, or the pharmaceutically acceptable salt thereof, is administered in a pharmaceutical composition and the pharmaceutical composition further comprises a pharmaceutically acceptable carrier. In one illustrative aspect, the pharmaceutical composition may be an aqueous solution which may contain carriers, diluents, solvents, encapsulating materials, a binder, a disintegrating agent, a lubricant, a solubilizing agent, a suspension aid, an emulsifying agent, a coating agent, or excipients, such as salts, carbohydrates and buffering agents (preferably at a pH of from 3 to 9), but they may be also be formulated as a sterile non-aqueous solution or as a dried form to be used in conjunction with a suitable vehicle such as sterile, pyrogen-free water or sterile saline. In other embodiments, a liquid formulation may be adapted for parenteral administration. The preparation under sterile conditions, by lyophilization, to produce a sterile lyophilized powder for a parenteral formulation, may readily be accomplished using standard pharmaceutical techniques well-known to those skilled in the art. In one embodiment, the solubility of the triazolopyrimidinone, or the derivative thereof, or the pharmaceutically acceptable salt thereof, used in the preparation of a parenteral formulation may be increased by the use of appropriate formulation techniques, such as the incorporation of solubility-enhancing agents.

In any of the above-described dose embodiments, a single dose (e.g., a single injection) or multiple doses of the triazolopyrimidinone, or the derivative thereof, or the pharmaceutically acceptable salt thereof, may be administered to the patient. In various aspects, any suitable regimen for administration of the triazolopyrimidinone, or the derivative thereof, or the pharmaceutically acceptable salt thereof, can be used. In accordance with the methods described herein, the triazolopyrimidinone, or the derivative thereof, or the pharmaceutically acceptable salt thereof, may be administered to the patient, for example using a regimen of daily or weekly administration, such as once a day, two times a day, three times a day, every day, every other day, one time weekly, two times weekly, three times weekly, once monthly, once every two, three, four, five, or six months, or any other suitable regimen that would be considered a suitable regimen by a person skilled in the art for administration of the triazolopyrimidinone, or the derivative thereof, or the pharmaceutically acceptable salt thereof. In another aspect, any combination of the embodiments described in this paragraph can be used.

In one aspect, in the methods described herein, the methods can further comprise administering an anti-VEGF agent. In various embodiments, the anti-VEGF agents may include, for example, anti-VEGF biologics such as ranibizumab, bevacizumab, or aflibercept, abicipar pegol, brolucizumab, faricimab, vorolanib, biosimilars to any of these VEGF agents, and combinations thereof. In another aspect, the anti-VEGF agents may include, for example, biologics such as antisense RNA that targets VEGF expression, an agent for RNA silencing or RNA interference (RNAi) that targets VEGF expression, ribozymes that target VEGF expression; FOVISTA™ and other agents targeting platelet derived growth factor (PDGF); squalamine ((1S,2S,5S,7R,9R,10R,11S,14R,15R)—N-{3-[(4-aminobutyl)amino]propyl}-9-hy-droxy-2,15-dimethyl-14-[(2R,5R)-6-methyl-5-(sulfooxy)heptan-2-yl]tetracycl-o[8.7.0.0 {2,7}.0 {11,15}] heptadecan-5-aminium); X-82 (Tyrogenix, NeedhamHeights, Mass.); PAN-90806 (PanOptica, Bernardsville, N.J.); TNP470 (Sigma-Aldrich, St. Louis, Mo.) and fumagillin (2E,4E,6E,8E)-10-{[(3R,4S,5S,6R)-5-methoxy-4-[(2R)-2-methyl-3-(3-methylbu-t-2-enyl)oxiran-2-yl]-1-oxaspiro[2.5]octan-6-yl]oxy}-10-oxodeca-2,4,6,8-te-traenoic acid); protein kinase C inhibitors; inhibitors of VEGF receptor kinase; pigment epithelium derived factor (PEDF); endostatin; angiostatin; anecortave acetate; triamcinolone ((11.beta., 16.alpha.)-9-Fluoro-11,16,17,21-tetrahydroxypregna-1,4-diene-3,20-dione); verteporfin (3-[(23S,24R)-14-ethenyl-5-(3-methoxy-3-oxopropyl)-22,23-bis (methoxycarbo-nyl)-4,10,15,24-tetramethyl-25,26,27,28-tetraazahexacyclo[16.6.1.1.sup.3,6-0.1.sup.8,11.1.sup.13,16.0.sup.19,24]octacosa-1,3,5,7,9,11(27),12,14,16,18(−25),19,21-dodecaen-9-yl]propanoic acid), porfimer sodium (photofrin), 5-aminolevulinic acid, and combinations thereof.

In one embodiment, an anti-VEGF agent is administered in combination with the triazolopyrimidinone, or the derivative thereof, or the pharmaceutically acceptable salt thereof. In one illustrative aspect, the anti-VEGF agent can be administered to the patient before the triazolopyrimidinone, or the derivative thereof, or the pharmaceutically acceptable salt thereof. In another embodiment, the anti-VEGF agent can be administered to the patient at the same time as the triazolopyrimidinone, or the derivative thereof, or the pharmaceutically acceptable salt thereof, but in different formulations, or in the same formulation. In yet another embodiment, the anti-VEGF agent can be administered to the patient after the triazolopyrimidinone, or the derivative thereof, or the pharmaceutically acceptable salt thereof.

In another embodiment, wherein the disease is malaria, the method can further comprise administering one or more of chloroquine (Aralen), quinine sulfate (Qualaquin), artemisinin, hydroxychloroquine (Plaquenil), mefloquine, a combination of atovaquone and proguanil (Malarone), and combinations thereof.

In yet another embodiment, wherein the disease is cancer, the cancer is selected from the group consisting of glioma, breast cancer, bladder cancer, colon cancer, and combinations thereof. In this embodiment, the method can further comprise treating the patient with photodynamic therapy (PDT), with agents such as verteporfin, 5-ALA, and the like, or diagnosing the patient with photodynamic diagnosis (PDD).

Various embodiments of the present disclosure will be more fully understood from the examples shown below. The EXAMPLES do not exemplify the full scope of the disclosure, but provide various additional illustrative aspects of the invention described herein and are not intended to be limiting in any way.

Examples

In these Examples, various triazolopyrimidinones were prepared and analyzed for their ability to inhibit FECH.

Materials and Methods

General methods and materials for the syntheses described below: All starting materials and reagents were obtained from commercial suppliers and were used without further purification. Air and moisture sensitive reactions were performed under an argon atmosphere. Flash column chromatography was performed using silica gel 60 (230-400 mesh, Merck) with the indicated solvents. Thin-layer chromatography was performed using 0.25 mm silica gel plates (Merck). $^1H$ and $^{13}C$ NMR spectra were recorded on a Bruker 600 MHz spectrometer as solutions in chloroform-d or dimethylsulfoxide-d6 or methanol-d4. $^1H$ NMR data were reported in the order of chemical shift, multiplicity (s, singlet; d, doublet; t, triplet; m, multiplet and/or multiple resonances), number of protons, and coupling constant (J) in hertz (Hz). High-resolution mass spectra (HRMS) were recorded on a JEOL JMS-700 (FAB and EI) and an Agilent 6530 Q-TOF LC/MS/MS system (ESI).

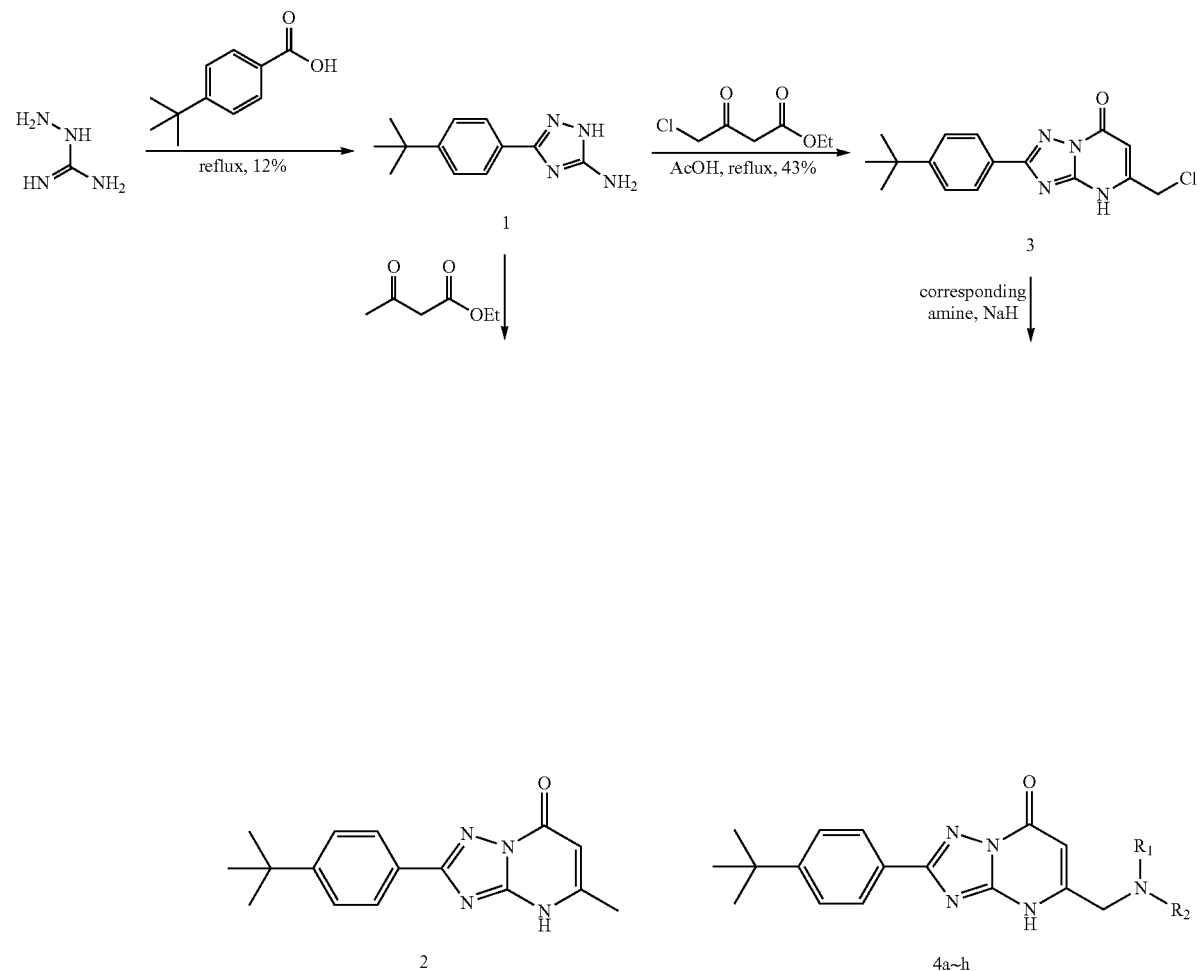

Scheme 1.

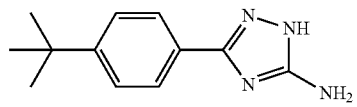

3-(4-(tert-butyl)phenyl)-1H-1,2,4-triazol-5-amine (1). To a solution of 4-tert-butylbenzoic acid (600 mg, 3.36 mmol) in CH$_2$Cl$_2$ (5 ml) was added SOCl$_2$ (2 mL) with stirring and placed in an ice bath. After stirring for 2 h at 60° C., the mixture was cooled to RT. The solvent was removed under reduced pressure. To the mixture was added toluene (2 mL) and aminoguanidine bicarbonate (460 mg, 3.36 mmol). After refluxing for 24 h, the mixture was cooled to RT. The reaction mixture was filtered and then the precipitates were purified by flash column chromatography on silica gel (MeOH/CH$_2$Cl$_2$=1:10) to afford compound (1) (90 mg, 12%). $^1$H-NMR (600 MHz, CDCl$_3$) δ 7.70 (d, 2H, J=9 Hz), 7.24 (d, 2H, J=8.4 Hz), 1.17 (s, 9H); $^{13}$C-NMR (150 MHz, CDCl$_3$) δ 159.6, 157.4, 153.0, 126.2, 126.0 125.7, 34.7, 31.2.

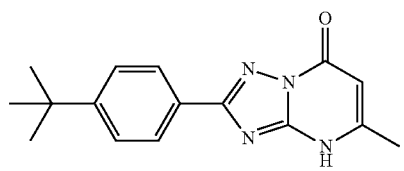 [SMILES: Cc1cc(=O)n2nc(-c3ccc(C(C)(C)C)cc3)nc2[nH]1]

2-(4-(tert-butyl)phenyl)-5-methyl-[1,2,4]triazolo[1,5-a]pyrimidin-7(4H)-one (2). To a mixture of 3-(4-(tert-butyl)phenyl)-1H-1,2,4-triazol-5-amine (1) (1.45 g, 6.73 mmol) and ethyl 3-oxobutanoate (5.1 mL, 40.4 mmol) was stirred at RT for 30 minutes. To the mixture was added toluene (13 mL) and p-toluenesulfonic acid (134 mg, 036 mmol). After refluxing for 24 h, the mixture was cooled to RT. The reaction mixture was filtered and then the precipitates were washed with toluene and dried to afford compound (2) (916 mg, 48%). $^1$H-NMR (600 MHz, DMSO-d6) δ 13.25 (bs, 1H), 8.07 (d, 2H, J=8.4 Hz), 7.55 (d, 2H, J=8.4 Hz), 5.85 (s, 1H), 2.34 (s, 3H), 1.32 (s, 9H); $^{13}$C-NMR (150 MHz, DMSO-d6) δ 161.2, 156.2, 153.4, 151.7, 151.5, 127.9, 126.9, 126.1, 98.9, 35.0, 31.4, 19.0.

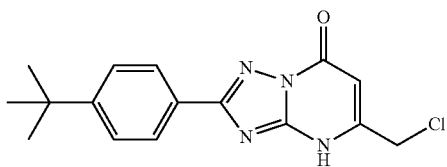 [SMILES: CC(C)(C)c1ccc(-c2nc3[nH]c(CCl)cc(=O)n3n2)cc1]

2-(4-(tert-butyl)phenyl)-5-(chloromethyl)-[1,2,4]triazolo[1, 5-a]pyrimidin-7(4H)-one (3). To a solution of 3-(4-(tert-butyl)phenyl)-1H-1,2,4-triazol-5-amine (1) (1.17 g, 5.14 mmol) in acetic acid (6 mL) was added ethyl 4-chloro-3-oxobutanoate (2.21 mL, 15.4 mmol). After stirring for 24 h at 80° C., a mixture was cooled to RT. The reaction mixture was filtered and then the precipitates were washed with acetonitrile and dried to afford the product (3) (690 mg, 43%). $^1$H-NMR (600 MHz, DMSO-d6) δ 13.79 (bs, 1H), 8.06 (d, 2H, J=8.4 Hz), 7.58 (d, 2H, J=8.4 Hz), 6.2 (s, 1H), 4.69 (s, 2H), 1.32 (s, 9H); $^{13}$C-NMR (150 MHz, DMSO-d6) δ 158.5, 156.2, 153.8, 151.9, 149.4, 127.2, 126.9, 126.2, 100.4, 41.8, 35.1, 31.4.

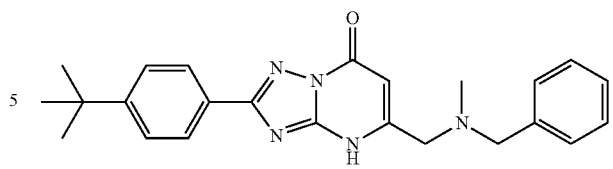

5-((benzyl(methyl)amino)methyl)-2-(4-(tert-butyl)phenyl)-[1,2,4]triazolo[1,5-a]pyrimidin-7(4H)-one (4a). A reaction mixture of chloromethyl compound (3) (55 mg, 0.17 mmol), N-benzylmethylamine (27 uL, 0.17 mmol) and sodium hydride (60% in oil, 20 mg, 0.51 mmol) in DMA (1 mL) was stirred in microwave at 250° C. for 60 minutes. The solvent was removed under reduced pressure and purified by flash column chromatograph on silica gel (MeOH/CH$_2$Cl$_2$/NH$_4$OH=1:20:0.1) to afford product (4a) (27.9 mg, 40%). $^1$H-NMR (600 MHz, DMSO-d6) δ 8.09 (d, 2H, J=8.4 Hz), 7.45 (d, 2H, J=7.8 Hz), 7.39 (t, 2H, J=7.8 Hz), 7.31 (t, 1H, J=7.2 Hz), 6.0 (s, 1H), 3.74 (s, 2H), 3.64 (s, 2H), 2.28 (s, 3H), 1.33 (s, 9H); $^{13}$C-NMR (150 MHz, DMSO-d6) δ 160.8, 156.5, 153.5, 153.3, 152.6, 137.0, 129.2, 128.3, 128.0, 127.5, 126.4, 125.6, 97.3, 60.6, 58.0, 41.4, 34.5, 31.0.

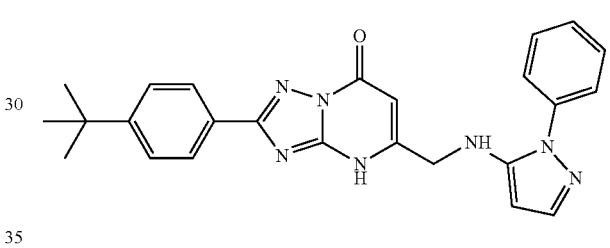

2-(4-(tert-butyl)phenyl)-5-(((1-phenyl-1H-pyrazol-5-yl)amino)methyl)-[1,2,4]triazolo[1,5-a]pyrimidin-7(4H)-one (4b). A reaction mixture of chloromethyl compound (3) (50 mg, 0.158 mmol), 5-Amino-1-phenylpyrazole (30 mg, 0.19 mmol) and sodium hydride (60% in oil, 19 mg, 0.47 mmol) in DMA (1 mL) was stirred in microwave at 250° C. for 60 minutes. The solvent was removed under reduced pressure and purified by flash column chromatography on silica gel (MeOH/CH$_2$Cl$_2$/NH$_4$OH=1:20:0.1) to afford product (4b) (7.6 mg, 11%). $^1$H-NMR (600 MHz, DMSO-d6) δ 8.05 (d, 2H, J=9 Hz), 7.68 (d, 2H, J=7.2 Hz), 7.57-7.53 (m, 4H), 7.40 (t, 1H, J=7.2 Hz), 7.36 (d, 1H, J=1.8 Hz), 6.26 (t, 1H, J=6 Hz), 6.06 (s, 1H), 5.58 (d, 1H, J=1.8 Hz), 4.26 (d, 2H, J=6 Hz), 1.33 (s, 9H); $^{13}$C-NMR (150 MHz, DMSO-d6) δ 156.3, 153.6, 151.8, 147.7, 140.4, 139.4, 129.8, 127.2, 126.9, 129.2, 124.0, 97.6, 88.7, 35.1, 31.4.(−3)

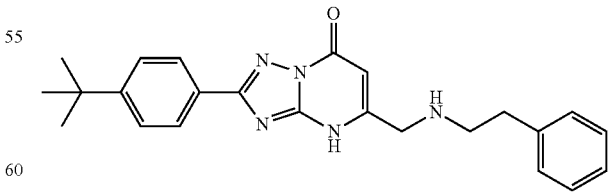

2-(4-(tert-butyl)phenyl)-5-((phenethylamino)methyl)-[1,2, 4]triazolo[1,5-a]pyrimidin-7(4H)-one (4c). A reaction mixture of chloromethyl compound (3) (50 mg, 0.158 mmol), Phenethylamine (23 uL, 0.19 mmol) and sodium hydride (60% in oil, 19 mg, 0.47 mmol) in DMA (1 mL) was stirred in microwave at 250° C. for 100 minutes. The solvent was removed under reduced pressure and purified by flash column chromatography on silica gel (MeOH/CH$_2$Cl$_2$/NH$_4$OH=1:20:0.1) to afford product (4c) (8.1 mg, 13%). $^1$H-NMR (600 MHz, DMSO-d6) δ 8.05 (d, 2H, J=8.4 Hz), 7.57 (d, 2H, J=8.4 Hz), 7.32-7.19 (m, 5H), 5.79 (d, 1H, J=40.8 Hz), 4.50 (d, 2H, J=5.4 Hz), 3.62 (t, 1H, J=7.2 Hz), 3.52 (t, 1H, J=7.2 Hz), 2.90 (t, 1H, J=7.2 Hz), 2.80 (t, 1H, J=7.2 Hz), 1.33 (d, 9H, J=1.2 Hz); $^{13}$C-NMR (150 MHz, DMSO-d6) δ 171.2, 156.3, 153.6, 151.9, 139.0, 129.4, 129.1, 128.9, 128.8, 126.9, 126.6, 126.2, 96.7, 60.2, 50.8, 35.1, 34.5, 31.4.

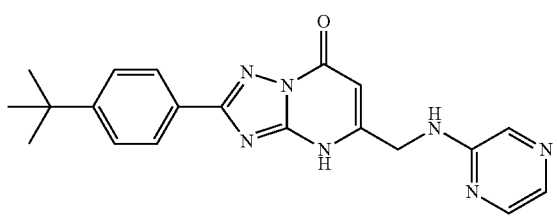 [SMILES: CC(C)(C)c1ccc(-c2nc3[nH]c(CNc4cnccn4)cc(=O)n3n2)cc1]

2-(4-(tert-butyl)phenyl)-5-((pyrazin-2-ylamino)methyl)-[1,2,4]triazolo[1,5-a]pyrimidin-7(4H)-one (4d). A reaction mixture of chloromethyl compound (3) (50 mg, 0.158 mmol), 2-Aminopyrazine (22.5 mg, 0.237 mmol) and sodium hydride (60% in oil, 19 mg, 0.47 mmol) in DMA (1 mL) was stirred in microwave at 250° C. for 50 minutes. The solvent was removed under reduced pressure and purified by flash column chromatography on silica gel (MeOH/CH$_2$Cl$_2$/NH$_4$OH=1:20:0.1) to afford the product (4d) (6.4 mg, 11%). $^1$H-NMR (600 MHz, CD$_3$OD) δ 8.15 (d, 2H, J=9 Hz), 8.09 (d, 1H, J=1.8 Hz), 8.03 (q, 1H, J=1.8 Hz), 7.79 (d, 1H, J=3 Hz), 7.57 (d, 2H, J=8.4 Hz), 6.03 (s, 1H), 4.62 (s, 2H), 1.39 (s, 9H).

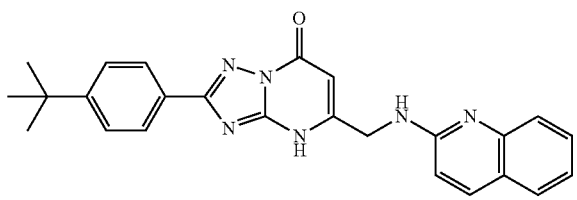 [SMILES: CC(C)(C)c1ccc(-c2nc3[nH]c(CNc4ccc5ccccc5n4)cc(=O)n3n2)cc1]

2-(4-(tert-butyl)phenyl)-5-((quinolin-2-ylamino)methyl)-[1,2,4]triazolo[1,5-a]pyrimidin-7(4H)-one (4e). A reaction mixture of 2-Aminoquinoline (34 mg, 0.237 mmol) and sodium hydride (60% in oil, 19 mg, 0.47 mmol) in DMF (1 mL) was stirred at 0° C. for 30 minutes. To the resultant clear solution was added chloromethyl compound (3) (50 mg, 0.158 mmol). The reaction mixture was stirred in microwave at 150° C. for 30 minutes. The solvent was removed under reduced pressure and purified by flash column chromatography on silica gel (MeOH/CH$_2$Cl$_2$/NH$_4$OH=1:20:0.1) to afford the product (4e) (6.1 mg, 10%). $^1$H-NMR (600 MHz, CD$_3$OD) δ 8.02 (d, 2H, J=8.4 Hz), 7.94 (d, 1H, J=9 Hz), 7.62 (d, 1H, J=8.4 Hz), 7.60 (d, 1H, J=7.8 Hz), 7.49 (t, 1H, J=7.2 Hz), 7.42 (d, 2H, J=9 Hz), 7.21 (t, 1H, J=7.2 Hz), 6.88 (d, 1H, J=9 Hz), 5.93 (s, 1H), 4.60 (s, 2H), 1.26 (s, 9H); $^{13}$C-NMR (150 MHz, DMSO-d6) δ 170.0, 156.6, 156.5, 153.5, 152.1, 147.5, 137.4, 129.8, 128.1, 127.9, 126.9, 126.1, 126.1, 123.7, 122.4, 113.5, 96.5, 41.9, 35.1, 31.4.

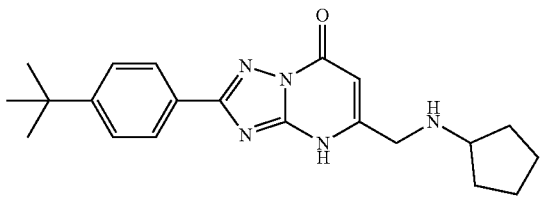 [SMILES: CC(C)(C)c1ccc(-c2nc3[nH]c(CNC4CCCC4)cc(=O)n3n2)cc1]

2-(4-(tert-butyl)phenyl)-5-((cyclopentylamino)methyl)-[1,2,4]triazolo[1,5-a]pyrimidin-7(4H)-one (4f). A reaction mixture of cyclopentylamine (24 uL, 0.237 mmol) and sodium hydride (60% in oil, 19 mg, 0.47 mmol) in DMF (1 mL) was stirred at 0° C. for 10 minutes. To the resultant was added chloromethyl compound (3) (50 mg, 0.158 mmol). The reaction mixture was stirred in microwave at 150° C. for 10 minutes. The solvent was removed under reduced pressure and purified by flash column chromatography on silica gel (MeOH/CH$_2$Cl$_2$/NH$_4$OH=1:20:0.1) to afford the product (4f) (32.6 mg, 10%). $^1$H-NMR (600 MHz, DMSO-d6) δ 8.06 (d, 2H, J=9 Hz), 7.50 (d, 2H, J=8.4 Hz), 5.66 (s, 1H), 4.02 (s, 2H), 3.53 (m, 1H), 2.00 (m, 2H), 1.72 (m, 4H), 1.55 (m, 2H), 1.32 (s, 9H); $^{13}$C-NMR (150 MHz, DMSO-d6) δ 160.5, 159.0, 157.8, 155.0, 151.7, 129.7, 126.2, 125.2, 94.4, 58.2, 49.2, 34.5, 31.1, 29.1, 23.6.

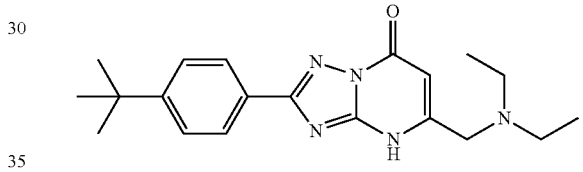

2-(4-(tert-butyl)phenyl)-5-((diethylamino)methyl)-[1,2,4]triazolo[1,5-a]pyrimidin-7(4H)-one (4 g). A reaction mixture of diethylamine (13 uL, 0.12 mmol) and sodium hydride (60% in oil, 10 mg, 0.237 mmol) in DMF (1 mL) was stirred at 0° C. for 10 minutes. To the resultant clear solution was added chloromethyl compound (3) (25 mg, 0.079 mmol). The reaction mixture was stirred in microwave at 150° C. for 10 minutes. The solvent was removed under reduced pressure and purified by flash column chromatography on silica gel (MeOH/CH$_2$Cl$_2$/NH$_4$OH=1:20:0.1) to afford product (4 g) (6.4 mg, 23%). $^1$H-NMR (600 MHz, CD$_3$OD) δ 8.03 (d, 2H, J=8.4 Hz), 7.44 (d, 2H, J=9 Hz), 5.86 (s, 1H), 4.15 (s, 2H), 3.19 (m, 4H), 1.28 (m, 15H); $^{13}$C-NMR (150 MHz, CD$_3$OD) δ 161.8, 159.6, 158.3, 157.6, 153.1, 128.1, 126.5, 125.2, 95.6, 55.6, 48.2, 34.3, 30.3, 8.0.

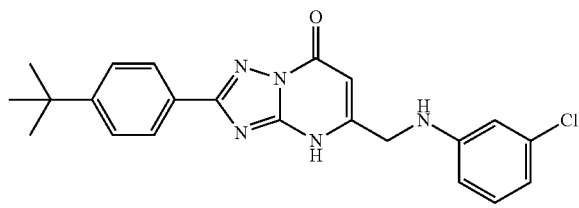 [SMILES: CC(C)(C)c1ccc(-c2nc3[nH]c(CNc4cccc(Cl)c4)cc(=O)n3n2)cc1]

2-(4-(tert-butyl)phenyl)-5-(((3-chlorophenyl)amino)methyl)-[1,2,4]triazolo[1,5-a]pyrimidin-7(4H)-one (4h). A reaction mixture of 3-chloroaniline (13 uL, 0.12 mmol) and sodium hydride (60% in oil, 20 mg, 0.47 mmol) in DMF (1 mL) was stirred at 0° C. for 10 minutes. To the resultant clear solution was added chloromethyl compound (3) (25 mg, 0.079 mmol). The reaction mixture was stirred in microwave at 150° C. for 2 minutes. The solvent was removed under reduced pressure and purified by flash column chromatography on silica gel (MeOH/CH$_2$Cl$_2$/NH$_4$OH=1:30:0.1) to afford the product (4h) (8.4 mg, 26%). $^1$H-NMR (600 MHz, CD$_3$OD) δ 8.15 (d, 2H, J=9 Hz), 7.54 (d, 2H, J=9 Hz), 7.08 (t, 1H, J=8.4 Hz), 6.66 (t, 1H, J=2.4 Hz), 6.61 (m, 1H), 6.57 (m, 1H), 6.06 (s, 1H), 4.32 (s, 2H), 1.38 (s, 9H); $^{13}$C-NMR (150 MHz, CD$_3$OD) δ 162.0, 161.3, 159.3, 156.2, 153.1, 149.5, 134.5, 129.9, 127.9, 126.7, 125.1, 116.4, 112.0, 110.7, 94.4, 46.7, 34.3, 30.3.

Scheme 2.

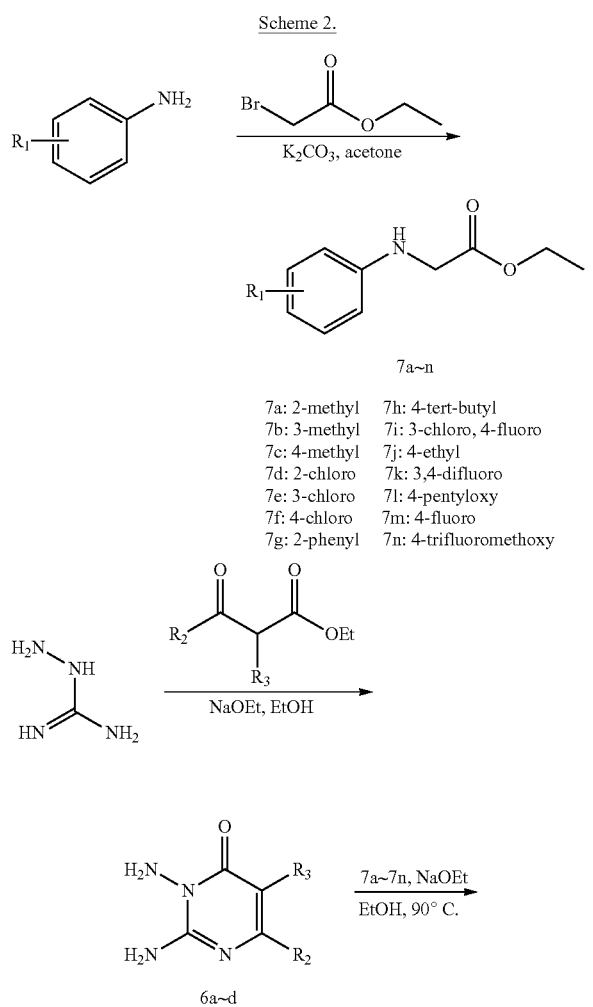

7a: 2-methyl  7h: 4-tert-butyl
7b: 3-methyl  7i: 3-chloro, 4-fluoro
7c: 4-methyl  7j: 4-ethyl
7d: 2-chloro  7k: 3,4-difluoro
7e: 3-chloro  7l: 4-pentyloxy
7f: 4-chloro  7m: 4-fluoro
7g: 2-phenyl  7n: 4-trifluoromethoxy 6a: R$_2$ = propyl, R$_3$ = H
6b: R$_2$,R$_3$ = cyclopentenyl
6c: R$_2$ = isopropyl, R$_3$ = H
6d: R$_2$ = methyl, R$_3$ = H

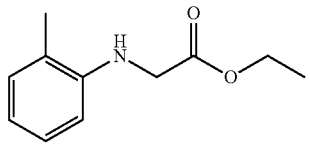

ethyl o-tolylglycinate (7a) To a THF (5 mL) solution of ethyl 2-bromoacetate (220 uL, 2 mmol), o-toluidine (214 uL, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:5) to afford ethyl o-tolylglycinate (7a) (386 mg, quantitative). $^1$H NMR (600 MHz, CDCl$_3$) δ 7.14 (td, 1H, J=7.8 and 1.2 Hz), 7.09 (d, 1H, J=7.2 Hz), 6.73 (td, 1H, J=7.8 and 0.6 Hz), 6.52 (d, 1H, J=7.8 Hz), 4.28 (q, 2H, J=7.2 Hz), 3.95 (s, 2H), 2.23 (s, 3H), 1.33 (t, 3H, J=7.2 Hz); $^{13}$C NMR (150 MHz, CDCl$_3$) δ 171.2, 144.9, 130.3, 127.1, 122.7, 118.0, 110.1, 61.4, 46.0, 17.4, 14.2.

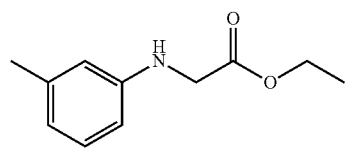

ethyl m-tolylglycinate (7b) To a THF (5 mL) solution of ethyl 2-bromoacetate (220 uL, 2 mmol), m-toluidine (214 uL, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:5) to afford ethyl m-tolylglycinate (7b) (364 mg, 94%). $^1$H NMR (600 MHz, CDCl$_3$) δ 7.11 (td, 1H, J=7.8 and 1.2 Hz), 6.26 (t, 1H, J=7.8 Hz), 6.49 (s, 2H), 4.26 (q, 2H, J=7.2 Hz), 3.91 (t, 2H, J=1.8 Hz), 2.29 (s, 3H), 1.31 (t, 3H, J=7.2 Hz); $^{13}$C NMR (150 MHz, CDCl$_3$) δ 171.1, 146.8, 139.2, 129.2, 119.5, 114.1, 110.4, 61.3, 46.1, 21.6, 14.2

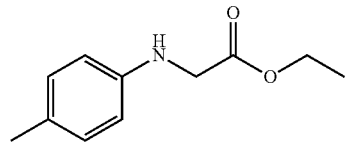

ethyl p-tolylglycinate (7c) To a THF (5 mL) solution of ethyl 2-bromoacetate (220 uL, 2 mmol), p-toluidine (214 uL, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:5) to afford ethyl p-tolylglycinate (7c) (331 mg, 86%). $^1$H NMR (600 MHz, CDCl$_3$) δ 7.01 (d, 2H, J=8.4 Hz), 6.57 (d, 2H, J=8.4 Hz), 4.25 (q, 2H, J=6.6 Hz), 3.88 (s, 2H), 2.24 (s,

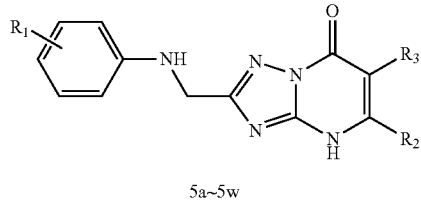

5a~5w

3H), 1.30 (t, 3H, J=7.2 Hz); $^{13}$C NMR (150 MHz, CDCl$_3$) δ 171.2, 144.6, 129.8, 127.7, 113.4, 61.3, 46.4, 20.4, 14.2.

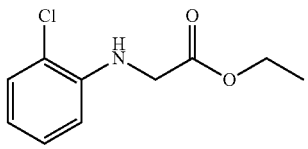

ethyl (2-chlorophenyl)glycinate (7d) To a THF (5 mL) solution of ethyl 2-bromoacetate (220 uL, 2 mmol), 2-chloroaniline (328 mg, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:5) to afford ethyl (2-chlorophenyl)glycinate (7d) (96 mg, 23%). $^1$H NMR (600 MHz, CDCl$_3$) δ 7.22 (dd, 1H, J=8.4 and 1.8 Hz), 7.09 (td, 1H, J=7.8 and 1.2 Hz), 6.64 (t, 1H, J=8.4 Hz), 6.50 (t, 1H, J=7.2 Hz), 4.21 (q, 2H, J=7.2 Hz), 3.89 (s, 3H), 1.25 (t, 3H, J=7.2 Hz); $^{13}$C NMR (150 MHz, CDCl$_3$) δ 170.5, 142.8, 129.3, 127.8, 119.8, 118.3, 111.5, 61.5, 46.7, 14.2.

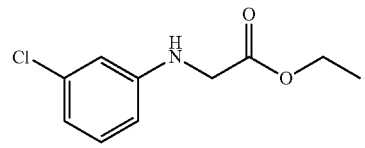

ethyl (3-chlorophenyl)glycinate (7e) To a THF (5 mL) solution of ethyl 2-bromoacetate (220 uL, 2 mmol), 3-chloroaniline (328 mg, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:10) to afford ethyl (3-chlorophenyl) glycinate (7e) (274 mg, 64%). $^1$H NMR (600 MHz, CDCl$_3$) δ 7.04 (t, 1H, J=8.4 Hz), 6.67 (d, 1H, J=7.8 Hz), 6.54 (d, 1H, J=1.8 Hz), 6.46 (dd, 1H, J=8.4 and 2.4 Hz), 4.20 (q, 2H, J=7.2 Hz), 3.81 (s, 2H), 1.25 (t, 3H, J=7.2 Hz); $^{13}$C NMR (150 MHz, CDCl$_3$) δ 170.5, 147.8, 135.1, 130.3, 118.4, 113.0, 111.7, 64.6, 45.7, 14.2.

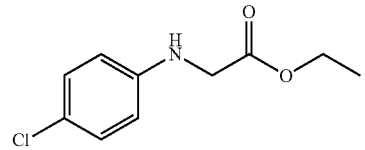

ethyl (4-chlorophenyl)glycinate (7f) To a THF (5 mL) solution of ethyl 2-bromoacetate (220 uL, 2 mmol), 4-chloroaniline (255 mg, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:5) to afford ethyl (4-chlorophenyl)glycinate (7f) (322 mg, 76%). $^1$H NMR (600 MHz, CDCl$_3$) δ 7.09 (d, 2H, J=8.4 Hz), 6.52 (m, 2H), 4.19 (q, 2H, J=7.2 Hz), 3.81 (s, 2H), 1.24 (t, 3H, J=7.2 Hz); $^{13}$C NMR (150 MHz, CDCl$_3$) δ 170.6, 145.2, 129.9, 129.2, 114.6, 61.5, 46.2, 14.2.

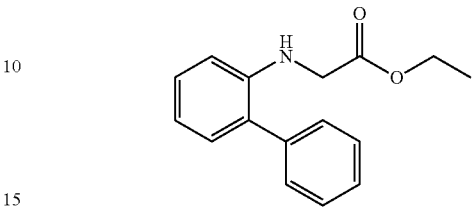

ethyl [1,1'-biphenyl]-2-ylglycinate (7 g) To a THF (5 mL) solution of ethyl 2-bromoacetate (220 uL, 2 mmol), 2-Aminobiphenyl (340 mg, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:10) to afford ethyl [1,1'-biphenyl]-2-ylglycinate (7 g) (100 mg, 19%). $^1$H NMR (600 MHz, CDCl$_3$) δ 7.50 (d, 4H, J=4.2 Hz), 7.41 (m, 1H), 7.29 (td, 1H, J=7.8 and 1.2 Hz), 7.18 (dd, 1H, J=7.2 and 1.2 Hz), 6.87 (td, 1H, J=7.2 and 0.6 Hz), 6.63 (d, 1H, J=7.8 Hz), 4.24 (q, 2H, J=7.2 Hz), 3.92 (s, 2H), 1.31 (t, 3H, J=7.2 Hz); $^{13}$C NMR (150 MHz, CDCl$_3$) δ 171.0, 143.9, 139.1, 130.4, 129.3, 129.0, 128.7, 128.2, 127.4, 117.9, 110.5, 61.3, 45.9, 14.2.

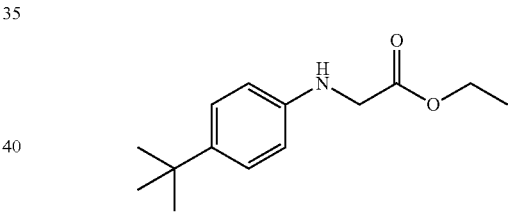

ethyl (4-(tert-butyl)phenyl)glycinate (7h) To a THF (5 mL) solution of ethyl 2-bromoacetate (322 mg, 2 mmol), 4-tert-Butylaniline (315 uL, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:10) to afford ethyl (4-(tert-butyl)phenyl) glycinate (7h) (306 mg, 65%). $^1$H NMR (600 MHz, CDCl$_3$) δ 7.26 (d, 2H, J=9 Hz), 6.64 (m, 2H), 4.29 (q, 2H, J=6.6 Hz), 3.92 (s, 2H), 1.33 (t, 3H, J=7.2 Hz), 1.30 (s, 9H); $^{13}$C NMR (150 MHz, CDCl$_3$) δ 171.2, 144.3, 141.4, 126.1, 113.1, 61.3, 46.3, 33.9, 31.5, 14.2.

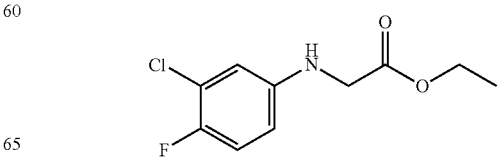

ethyl (3-chloro-4-fluorophenyl)glycinate (7i) To a THF (5 mL) solution of ethyl 2-bromoacetate (322 mg, 2 mmol), 3-chloro-4-fluoro aniline (291 mg, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:5) to afford ethyl (3-chloro-4-fluorophenyl)glycinate (7i) (119 mg, 26%). $^1$H NMR (600 MHz, CDCl$_3$) δ 6.90 (t, 1H, J=9 Hz), 6.53 (dd, 1H, J=6 and 3 Hz), 6.38-6.35 (m, 1H), 4.19 (q, 2H, J=7.2 Hz), 3.77 (s, 2H), 1.24 (t, 3H, J=7.2 Hz); $^{13}$C NMR (150 MHz, CDCl$_3$) δ 170.7, 152.2, 150.6, 144.0, 121.2, 116.9, 114.0, 112.3, 61.5, 46.1, 14.2.

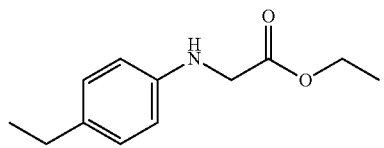

ethyl (4-ethylphenyl)glycinate (7j) To a THF (5 mL) solution of ethyl 2-bromoacetate (322 mg, 2 mmol), 4-Ethylaniline (249 uL, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:10) to afford ethyl (4-ethylphenyl)glycinate (7j) (245 mg, 59%). $^1$H NMR (600 MHz, CDCl$_3$) δ 7.07 (d, 2H, J=8.4 Hz), 6.62 (dd, 2H, J=6.6 and 2.4 Hz), 4.28 (q, 2H, J=7.2 Hz), 3.92 (s, 2H), 2.59 (q, 2H, J=7.8 Hz), 1.33 (t, 3H, J=7.2 Hz), 1.22 (t, 3H, J=7.8 Hz); $^{13}$C NMR (150 MHz, CDCl$_3$) δ 171.2, 144.7, 134.4, 128.7, 113.4, 61.3, 46.4, 27.9, 15.9, 14.2.

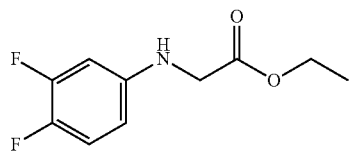

ethyl (3,4-difluorophenyl)glycinate (7k) To a THF (5 mL) solution of ethyl 2-bromoacetate (322 mg, 2 mmol), 3,4-difluoroaniline (258 mg, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:7) to afford ethyl (3,4-difluorophenyl)glycinate (7k) (125 mg, 29%). $^1$H NMR (600 MHz, CDCl$_3$) δ 6.90 (q, 1H, J=9 Hz), 6.31 (dd, 1H, J=6.6 and 3 Hz), 6.19 (d, 1H, J=9 Hz), 4.24 (bs, 1H), 4.18 (q, 2H, J=7.2 Hz), 3.74 (s, 2H), 1.22 (td, 3H, J=7.2 and 1.2 Hz); $^{13}$C NMR (150 MHz, CDCl$_3$) δ 170.7, 151.7, 150.0, 144.2, 144.1, 142.7, 117.5, 108.1, 101.7, 61.5, 46.0, 14.1.

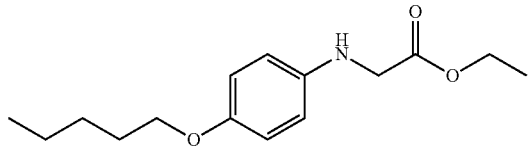 [SMILES: CCCCCOc1ccc(NCC(=O)OCC)cc1]

ethyl (4-(pentyloxy)phenyl)glycinate (7l) To a THF (5 mL) solution of ethyl 2-bromoacetate (322 mg, 2 mmol), 4-(pentyloxy)aniline (370 uL, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:5) to afford ethyl (4-(pentyloxy)phenyl)glycinate (7l) (171 mg, 32%). $^1$H NMR (600 MHz, CDCl$_3$) δ 6.72 (d, 2H, J=8.4 Hz), 6.54 (d, 2H, J=8.4 Hz), 4.18 (q, 2H, J=6.6 Hz), 3.82 (d, 2H, J=6.6 Hz), 3.80 (s, 2H), 1.68 (dd, 2H, J=8.4 and 7.2 Hz), 1.36-1.29 (m, 4H), 1.23 (t, 3H), 0.86 (t, 3H, J=7.2 Hz); $^{13}$C NMR (150 MHz, CDCl$_3$) δ 171.3, 147.8, 140.8, 123.7, 115.8, 68.7, 61.3, 47.1, 29.1, 28.2, 22.5, 14.2, 14.0.

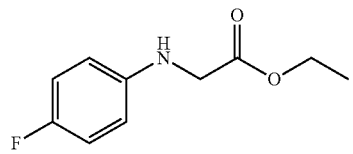

ethyl (4-fluorophenyl)glycinate (7m) To a THF (5 mL) solution of ethyl 2-bromoacetate (322 mg, 2 mmol), 4-fluoroaniline (190 uL, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:5) to afford ethyl (4-fluorophenyl)glycinate (7m) (193 mg, 49%). $^1$H NMR (600 MHz, CDCl$_3$) δ 6.85 (d, 2H, J=8.4 Hz), 6.49 (dd, 2H, J=9 and 4.2 Hz), 4.19 (q, 2H, J=7.2 Hz), 3.79 (s, 2H), 1.24 (t, 3H, J=7.2 Hz); $^{13}$C NMR (150 MHz, CDCl$_3$) δ 171.1, 157.0, 155.5, 143.4, 115.9, 113.9, 61.4, 46.5, 14.2.

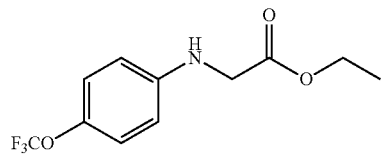

ethyl (4-(trifluoromethoxy)phenyl)glycinate (7n) To a THF (5 mL) solution of ethyl 2-bromoacetate (322 mg, 2 mmol), 4-(trifluoromethoxy)aniline (268 uL, 2 mmol) and K$_2$CO$_3$ (830 mg, 6 mmol) were added. After refluxing for 24 h, the reaction mixture was diluted with ethyl acetate and the organic phase was washed with water and brine, dried over MgSO$_4$, and concentrated under reduced pressure. The residue was purified by flash column chromatography on silica gel (ethyl acetate/n-hexane=1:5) to afford ethyl (4-(tert-butyl)phenyl)glycinate (7n) (134 mg, 25%). $^1$H NMR (600 MHz, CDCl₃) δ 7.08 (d, 2H, J=8.4 Hz), 6.58 (d, 2H, J=9 Hz), 4.44 (bs, 1H), 4.29 (q, 2H, J=6.6 Hz), 3.89 (s, 2H), 1.33 (t, 3H, J=7.2 Hz); $^{13}$C NMR (150 MHz, CDCl₃) δ 170.9, 145.9, 141.0, 122.4, 121.5, 119.9, 113.2, 61.5, 45.8, 14.1.

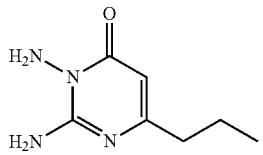

2,3-diamino-6-propylpyrimidin-4(3H)-one (6a) To a solution of NaOEt prepared from sodium (340 mg, 14.7 mmol) and ethanol (10 mL), 2-aminoguanidine (1.62 g, 14.7 mmol) was added and the reaction was heated at 90° C. for 30 min and after cooling NaCl filtered. Then, ethyl 3-oxohexanoate (2.34 mL, 14.7 mmol) was added to the reaction mixture and heated at reflux for 15 h. The precipitate obtained was filtered and dried under vacuum to afford 2,3-diamino-6-propylpyrimidin-4(3H)-one (6a) (515 mg, 21%). $^{1}$H NMR (600 MHz, DMSO-d6) δ 7.07 (bs, 2H), 5.53 (s, 1H), 5.35 (m, 2H), 2.23 (t, 2H, J=7.2 Hz), 1.57 (m, 2H), 0.88-0.85 (m, 3H); $^{13}$C NMR (150 MHz, DMSO-d6) δ 166.8, 161.8, 156.0, 98.6, 39.3, 21.4, 14.0.

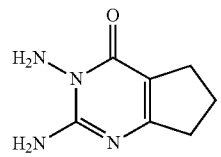

2,3-diamino-3,5,6,7-tetrahydro-4H-cyclopenta[d]pyrimidin-4-one (6b) To a solution of NaOEt prepared from sodium (340 mg, 14.7 mmol) and ethanol (10 mL), 2-aminoguanidine (1.62 g, 14.7 mmol) was added and the reaction was heated at 90° C. for 30 min and after cooling NaCl filtered. Then, ethyl 2-cyclopentane-1-carboxylate (2.12 mL, 14.7 mmol) was added to the reaction mixture and heated at reflux for 15 h. The precipitate obtained was filtered and dried under vacuum to afford 2,3-diamino-3,5,6,7-tetrahydro-4H-cyclopenta[d]pyrimidin-4-one (6b) (250 mg, 10%). $^{1}$H NMR (600 MHz, DMSO-d6) δ 6.92 (bs, 2H), 5.30 (s, 2H), 2.56 (q, 4H, J=9 Hz), 1.92 (m, 2H); $^{13}$C NMR (150 MHz, DMSO-d6) δ 167.1, 158.6, 155.3, 108.3, 33.8, 26.6, 20.7.

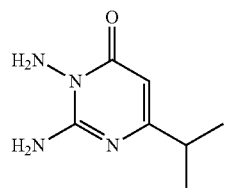

2,3-diamino-6-isopropylpyrimidin-4(3H)-one (6c) To a solution of NaOEt prepared from sodium (340 mg, 14.7 mmol) and ethanol (10 mL), 2-aminoguanidine (1.62 g, 14.7 mmol) was added and the reaction was heated at 90° C. for 30 min and after cooling NaCl filtered. Then, ethyl 4-methyl-3-oxopentanoate (2.37 mL, 14.7 mmol) was added to the reaction mixture and heated at reflux for 15 h. The precipitate obtained was filtered and dried under vacuum to afford 2,3-diamino-6-isopropylpyrimidin-4(3H)-one (6c) (469 mg, 19%). $^{1}$H NMR (600 MHz, DMSO-d6) δ 7.02 (bs, 2H), 5.53 (s, 1H), 5.32 (s, 2H), 2.50 (m, 1H), 1.10 (s, 3H), 1.09 (s, 3H); $^{13}$C NMR (150 MHz, DMSO-d6) δ 170.8, 160.9, 155.0, 95.2, 34.4, 20.7.

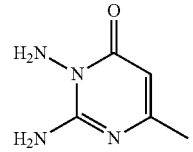

2,3-diamino-6-methylpyrimidin-4(3H)-one (6d) To a solution of NaOEt prepared from sodium (340 mg, 14.7 mmol) and ethanol (10 mL), 2-aminoguanidine (1.62 g, 14.7 mmol) was added and the reaction was heated at 90° C. for 30 min and after cooling NaCl filtered. Then, ethyl 3-oxobutanoate (1.35 mL, 14.7 mmol) was added to the reaction mixture and heated at reflux for 15 h. The precipitate obtained was filtered and dried under vacuum to afford 2,3-diamino-6-methyl-pyrimidin-4(3H)-one (6d) (335 mg, 16%). $^{1}$H NMR (600 MHz, DMSO-d6) δ 7.03 (bs, 2H), 5.52 (s, 1H), 5.30 (s, 2H), 1.99 (s, 3H); $^{13}$C NMR (150 MHz, DMSO-d6) δ 162.4, 160.5, 154.8, 98.0, 22.9.

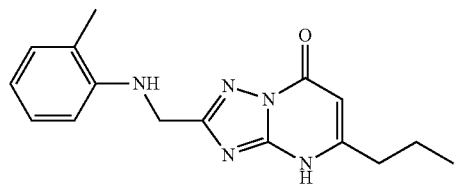 [SMILES: CCCc1cc(=O)n2nc(CNc3ccccc3C)nc2[nH]1]

5-propyl-2-((o-tolylamino)methyl)-[1,2,4]triazolo[1,5-a]pyrimidin-7(4H)-one (5a) To a solution of NaOEt prepared from sodium (6 mg) and ethanol (1 mL), 2,3-diamino-6-propyl-pyrimidin-4-one (6a) (20 mg, 118.9 umol) was added and the reaction was heated at 80° C. for 30 min. Then, ethyl 2-(2-methylanilino)acetate (7a) (23 mg, 118.9 umol) was added to the reaction mixture and heated at reflux for 15 h, and then stirred at RT overnight. The precipitate obtained was filtered and dried under vacuum, then purified by flash column chromatography on silica gel (MeOH/CH₂Cl₂=1:30) to afford 5-propyl-2-((o-tolylamino)methyl)-[1,2,4]triazolo[1,5-a]pyrimidin-7(4H)-one (5a) (8.7 mg, 25%). $^{1}$H NMR (600 MHz, DMSO-d6) δ 13.09 (bs, 1H), 6.97 (m, 2H), 6.61 (d, 1H, J=7.8 Hz), 6.52 (t, 1H, J=7.2 Hz), 5.81 (s, 1H), 4.42 (s, 2H), 2.55 (t, 2H, J=7.2 Hz), 2.13 (s, 3H), 1.68 (m, 2H), 0.92 (t, 3H, J=7.2 Hz); $^{13}$C NMR (150 MHz, DMSO-d6) δ 163.6, 156.3, 155.1, 151.4, 146.4, 130.2, 127.1, 122.2, 116.6, 110.0, 98.2, 41.6, 40.5, 21.6, 18.1, 13.7.

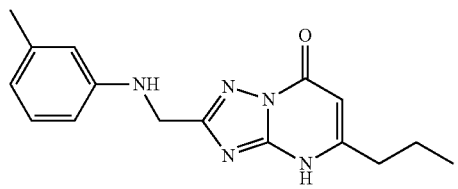 [SMILES: CCCc1cc(=O)n2nc(CNc3cccc(C)c3)nc2[nH]1]

5-propyl-2-((m-tolylamino)methyl)-[1,2,4]triazolo[1,5-a]pyrimidin-7(4H)-one (5b) To a solution of NaOEt prepared from sodium (6 mg) and ethanol (1 mL), 2,3-diamino-6-propyl-pyrimidin-4-one (6a) (20 mg, 118.9 umol) was added and the reaction was heated at 80° C. for 30 min. Then, ethyl 2-(3-methylanilino)acetate (7b) (23 mg, 118.9 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 5-propyl-2-((m-tolylamino)methyl)-[1,2,4]triazolo[1,5-a]pyrimidin-7(4H)-one (5b) (5.7 mg, 16%). $^1$H NMR (600 MHz, DMSO-d6) δ 13.06 (bs, 1H), 6.94 (t, 1H, J=7.8 Hz), 6.48 (s, 1H), 6.46 (d, 2H, J=7.8 Hz), 6.36 (d, 1H, J=7.2 Hz), 6.08 (t, 1H, J=6.6 Hz), 5.79 (s, 1H), 4.32 (d, 2H, J=60 Hz), 2.54 (t, 2H, J=7.8 Hz), 2.16 (s, 3H), 1.68 (m, 2H), 0.91 (t, 3H, J=7.2 Hz); $^{13}$C NMR (150 MHz, DMSO-d6) δ 173.3, 156.4, 148.8, 138.2, 130.2, 129.1, 122.1, 117.5, 113.5, 110.0, 98.0, 41.4, 40.5, 21.8, 21.7, 13.7.

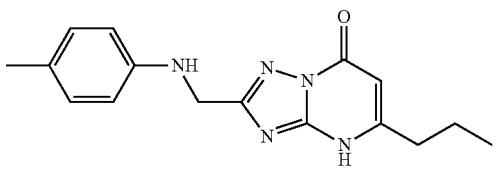 [SMILES: CCCc1cc(=O)n2nc(CNc3ccc(C)cc3)nc2[nH]1]

5-propyl-2-((p-tolylamino)methyl)-[1,2,4]triazolo[1,5-a]pyrimidin-7(4H)-one (5c) To a solution of NaOEt prepared from sodium (6 mg) and ethanol (1 mL), 2,3-diamino-6-propyl-pyrimidin-4-one (6a) (20 mg, 118.9 umol) was added and the reaction was heated at 80° C. for 30 min. Then, ethyl 2-(4-methylanilino)acetate (7c) (23 mg, 118.9 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 5-propyl-2-((p-tolylamino)methyl)-[1,2,4]triazolo[1,5-a]pyrimidin-7(4H)-one (5c) (9.7 mg, 28%). $^1$H NMR (600 MHz, DMSO-d6) δ 13.05 (bs, 1H), 6.87 (d, 2H, J=8.4 Hz), 6.57 (d, 2H, J=8.4 Hz), 5.97 (t, 1H, J=6 Hz), 5.79 (s, 1H), 4.30 (d, 2H, J=6 Hz), 2.54 (t, 2H, J=7.2 Hz), 2.12 (s, 3H), 1.67 (m, 2H), 0.91 (t, 3H, J=7.2 Hz); $^{13}$C NMR (150 MHz, DMSO-d6) δ 168.9, 156.3, 151.4, 149.5, 146.5, 129.7, 124.9, 112.9, 98.1, 41.6, 40.5, 21.6, 20.5, 13.7.

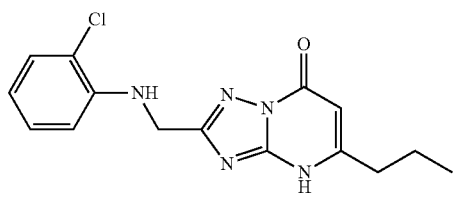 [SMILES: CCCc1cc(=O)n2nc(CNc3ccccc3Cl)nc2[nH]1]

2-(((2-chlorophenyl)amino)methyl)-5-propyl-[1,2,4]triazolo[1,5-a]pyrimidin-7(4H)-one (5d) To a solution of NaOEt prepared from sodium (6 mg) and ethanol (1 mL), 2,3-diamino-6-propyl-pyrimidin-4-one (6a) (20 mg, 118.9 umol) was added and the reaction was heated at 80° C. for 30 min. Then, ethyl (2-chlorophenyl)glycinate (7d) (25 mg, 118.9 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(((2-chlorophenyl)amino)methyl)-5-propyl-[1,2,4]triazolo[1,5-a]pyrimidin-7(4H)-one (5d) (14.7 mg, 39%). $^1$H NMR (600 MHz, DMSO-d6) δ 13.11 (bs, 1H), 7.27 (dd, 1H, J=7.8 and 1.2 Hz), 7.11 (t, 1H, J=8.4 Hz), 6.79 (dd, 1H, J=7.8 and 0.6 Hz), 6.61 (td, 1H, J=7.8 and 1.2 Hz), 5.96 (t, 1H, J=6 Hz), 5.81 (s, 1H), 4.50 (d, 2H, J=6 Hz), 2.54 (t, 2H, J=7.2 Hz), 1.67 (m, 2H), 0.92 (t, 3H, J=7.2 Hz); $^{13}$C NMR (150 MHz, DMSO-d6) δ 162.8, 156.3, 155.3, 151.6, 144.2, 129.4, 128.4, 118.3, 117.4, 112.1, 98.2, 41.2, 34.6, 21.6, 13.7.

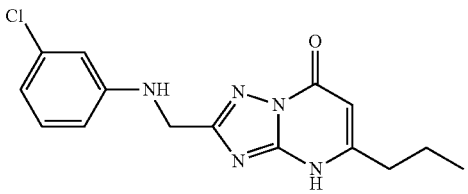 [SMILES: CCCc1cc(=O)n2nc(CNc3cccc(Cl)c3)nc2[nH]1]

2-(((3-chlorophenyl)amino)methyl)-5-propyl-[1,2,4]triazolo[1,5-a]pyrimidin-7(4H)-one (5e) To a solution of NaOEt prepared from sodium (6 mg) and ethanol (1 mL), 2,3-diamino-6-propyl-pyrimidin-4-one (6a) (20 mg, 118.9 umol) was added and the reaction was heated at 80° C. for 30 min. Then, ethyl (3-chlorophenyl)glycinate (7e) (25 mg, 118.9 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(((3-chlorophenyl)amino)methyl)-5-propyl-[1,2,4]triazolo[1,5-a]pyrimidin-7(4H)-one (5e) (12.3 mg, 33%). $^1$H NMR (600 MHz, DMSO-d6) δ 13.07 (bs, 1H), 7.07 (td, 1H, J=7.8 and 1.8 Hz), 6.70 (s, 1H), 6.62 (m, 2H), 6.54 (d, 1H, J=7.8 Hz), 5.81 (d, 1H, J=1.8 Hz), 4.37 (d, 2H, J=6.6 Hz), 2.55 (t, 2H, J=7.8 Hz), 1.68 (m, 2H), 0.92 (td, 3H, J=7.8 Hz); $^{13}$C NMR (150 MHz, DMSO-d6) δ 172.8, 162.9, 156.3, 151.5, 150.4, 134.0, 130.7, 115.9, 111.9, 111.5, 98.2, 41.1, 34.6, 21.6, 13.7.

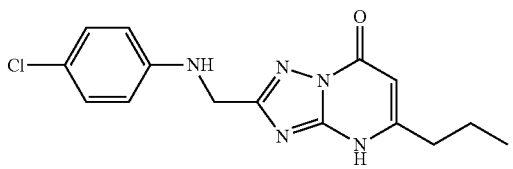 [SMILES: CCCc1cc(=O)n2nc(CNc3ccc(Cl)cc3)nc2[nH]1]

2-(((4-chlorophenyl)amino)methyl)-5-propyl-[1,2,4]triazolo[1,5-a]pyrimidin-7(4H)-one (5f) To a solution of NaOEt prepared from sodium (6 mg) and ethanol (1 mL), 2,3-diamino-6-propyl-pyrimidin-4-one (6a) (20 mg, 118.9 umol) was added and the reaction was heated at 80° C. for 30 min. Then, ethyl (4-chlorophenyl)glycinate (7f) (25 mg, 118.9 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(((4-chlorophenyl)amino)methyl)-5-propyl-[1,2,4]triazolo[1,5-a]pyrimidin-7(4H)-one (5f) (18.5 mg, 49%). $^1$H NMR (600 MHz, DMSO-d6) δ 13.05 (bs, 1H), 7.08 (d, 2H, J=8.4 Hz), 6.68 (d, 2H, J=9 Hz), 6.47 (t, 1H, J=6 Hz), 5.80 (s, 1H), 4.35 (d, 2H, J=6 Hz), 2.54 (t, 2H, J=7.2 Hz), 1.67-1.63 (m, 2H), 0.91 (t, 3H, J=7.2

Hz); $^{13}$C NMR (150 MHz, DMSO-d6) δ 172.4, 162.6, 155.8, 151.1, 147.3, 128.5, 119.3, 113.7, 97.7, 40.8, 34.1, 21.2, 13.2.

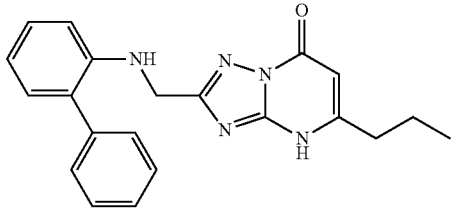 [SMILES: CCCc1cc(=O)n2nc(CNc3ccccc3-c3ccccc3)nc2[nH]1]

2-(([1,1'-biphenyl]-2-ylamino)methyl)-5-propyl-[1,2,4]triazolo[1,5-a]pyrimidin-7(4H)-one (5 g) To a solution of NaOEt prepared from sodium (13 mg) and ethanol (1 mL), 2,3-diamino-6-propyl-pyrimidin-4-one (6a) (30 mg, 178 umol) was added and the reaction was heated at 80° C. for 30 min. Then, ethyl [1,1'-biphenyl]-2-ylglycinate (7 g) (45 mg, 178 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(([1,1'-biphenyl]-2-ylamino)methyl)-5-propyl-[1,2,4]triazolo[1,5-a]pyrimidin-7(4H)-one (5 g) (18.9 mg, 30%). $^1$H NMR (600 MHz, CDCl$_3$) δ 12.41 (bs, 1H), 7.09 (d, 5H, J=4.2 Hz), 7.05-7.03 (m, 1H), 6.95 (dd, 1H, J=7.2 and 1.2 Hz), 6.71 (td, 1H, J=7.8 and 1.2 Hz), 6.66 (d, 1H, J=7.8 Hz), 5.65 (s, 1H), 4.55 (bs, 1H), 4.31 (s, 2H), 2.32 (t, 2H, J=7.8 Hz), 1.44 (m, 2H), 0.77 (t, 3H, J=7.8 Hz); $^{13}$C NMR (150 MHz, CDCl$_3$) δ 162.6, 156.3, 155.0, 150.6, 143.8, 138.8, 130.4, 128.8, 128.8, 128.6, 127.8, 127.1, 118.2, 110.8, 98.7, 42.0, 34.8, 20.9, 13.5.

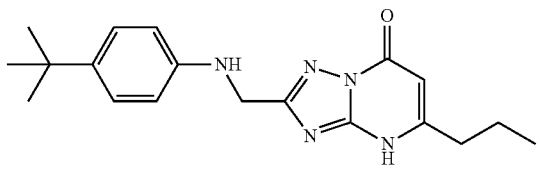 [SMILES: CCCc1cc(=O)n2nc(CNc3ccc(C(C)(C)C)cc3)nc2[nH]1]

2-(((4-(tert-butyl)phenyl)amino)methyl)-5-propyl-[1,2,4]triazolo[1,5-a]pyrimidin-7(4H)-one (5h) To a solution of NaOEt prepared from sodium (13 mg) and ethanol (1 mL), 2,3-diamino-6-propyl-pyrimidin-4-one (6a) (30 mg, 178 umol) was added and the reaction was heated at 80° C. for 30 min. Then, ethyl (4-(tert-butyl)phenyl)glycinate (7h) (42 mg, 178 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(((4-(tert-butyl)phenyl)amino)methyl)-5-propyl-[1,2,4]triazolo[1,5-a]pyrimidin-7(4H)-one (5h) (31.2 mg, 52%). $^1$H NMR (600 MHz, CDCl$_3$) δ 7.15 (d, 2H, J=8.4 Hz), 6.52 (d, 2H, J=8.4 Hz), 5.77 (s, 1H), 4.47 (s, 2H), 2.54 (t, 2H, J=7.8 Hz), 1.63 (m, 2H), 1.24 (s, 9H), 0.92 (t, 3H, J=7.2 Hz); $^{13}$C NMR (150 MHz, CDCl$_3$) δ 163.0, 156.5, 155.3, 150.8, 144.7, 141.1, 126.0, 112.6, 98.7, 42.3, 34.8, 33.9, 31.5, 21.1, 13.4.

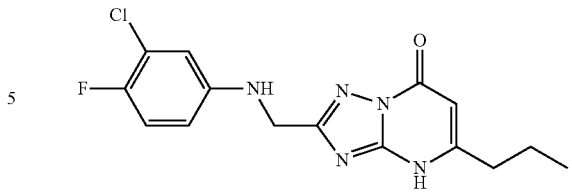

2-(((3-chloro-4-fluorophenyl)amino)methyl)-5-propyl-[1,2,4]triazolo[1,5-a]pyrimidin-7(4H)-one (5i) To a solution of NaOEt prepared from sodium (13 mg) and ethanol (1 mL), 2,3-diamino-6-propyl-pyrimidin-4-one (6a) (30 mg, 178 umol) was added and the reaction was heated at 80° C. for 30 min. Then, ethyl (3-chloro-4-fluorophenyl)glycinate (7i) (42 mg, 178 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(((3-chloro-4-fluorophenyl)amino)methyl)-5-propyl-[1,2,4]triazolo[1,5-a]pyrimidin-7(4H)-one (5i) (10.1 mg, 17%). $^1$H NMR (600 MHz, DMSO-d6) δ 13.03 (bs, 1H), 7.04 (t, 1H, J=9 Hz), 6.73 (dd, 1H, J=6.6 and 3 Hz), 6.57 (m, 1H), 6.40 (t, 1H, J=6 Hz), 5.72 (s, 1H), 4.27 (d, 2H, J=6 Hz), 2.47 (t, 2H, J=7.2 Hz), 1.61 (m, 1H), 0.85 (t, 3H, J=7.2 Hz); $^{13}$C NMR (150 MHz, DMSO-d6) δ 162.8, 156.4, 155.7, 151.8, 150.4, 148.9, 146.5, 119.7, 117.2, 113.0, 112.5, 98.0, 41.5, 34.8, 21.7, 13.7.

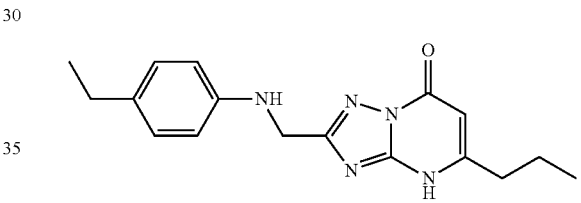

2-(((4-ethylphenyl)amino)methyl)-5-propyl-[1,2,4]triazolo[1,5-a]pyrimidin-7(4H)-one (5j) To a solution of NaOEt prepared from sodium (13 mg) and ethanol (1 mL), 2,3-diamino-6-propyl-pyrimidin-4-one (6a) (30 mg, 178 umol) was added and the reaction was heated at 80° C. for 30 min. Then, ethyl (4-ethylphenyl)glycinate (7j) (37 mg, 178 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(((4-ethylphenyl)amino)methyl)-5-propyl-[1,2,4]triazolo[1,5-a]pyrimidin-7(4H)-one (5j) (26 mg, 47%). $^1$H NMR (600 MHz, DMSO-d6) δ 13.06 (bs, 1H), 6.90 d, 2H, J=8.4 Hz), 6.60 (d, 2H, J=8.4 Hz), 5.99 (s, 1H), 5.80 (s, 1H), 4.32 (d, 2H, J=3.6 Hz), 2.54 (t, 2H, J=7.2 Hz), 2.44 (q, 2H, J=7.8 Hz), 1.68 (m, 2H), 1.10 (t, 3H, J=7.8 Hz), 0.92 (t, 3H, J=7.8 Hz); $^{13}$C NMR (150 MHz, DMSO-d6) δ 163.5, 156.3, 155.3, 151.5, 146.7, 131.7, 128.5, 112.9, 98.1, 41.6, 34.6, 27.8, 21.6, 16.6, 13.7.

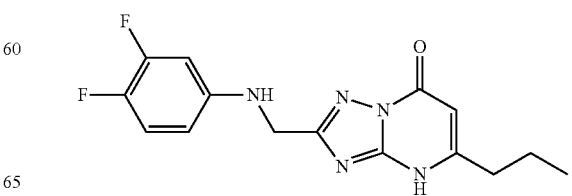

2-(((3,4-difluorophenyl)amino)methyl)-5-propyl-[1,2,4]triazolo[1,5-a]pyrimidin-7(4H)-one (5k) To a solution of NaOEt prepared from sodium (13 mg) and ethanol (1 mL), 2,3-diamino-6-propyl-pyrimidin-4-one (6a) (30 mg, 178 umol) was added and the reaction was heated at 80° C. for 30 min. Then, ethyl (3,4-difluorophenyl)glycinate (7k) (38 mg, 178 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(((3,4-difluorophenyl)amino)methyl)-5-propyl-[1,2,4]triazolo[1,5-a]pyrimidin-7(4H)-one (5k) (16.1 mg, 28%). $^1$H NMR (600 MHz, DMSO-d6) δ 13.08 (bs, 1H), 7.12 (q, 1H, J=3 Hz), 6.67 (m, 1H), 6.49 (t, 1H, J=6.6 Hz), 6.45 (d, 1H, J=9 Hz), 5.81 (s, 1H), 4.34 (d, 2H, J=6 Hz), 2.55 (t, 2H, J=7.2 Hz), 1.67 (m, 2H), 0.92 (t, 3H, J=7.2 Hz); $^{13}$C NMR (150 MHz, DMSO-d6) δ 162.4, 155.8, 154.8, 151.0, 150.7, 149.0, 146.1, 142.0, 140.5, 117.3, 107.9, 100.4, 97.7, 41.0, 34.1, 21.1, 13.2.

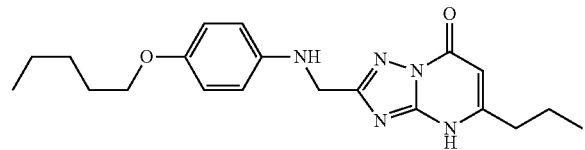 [SMILES: CCCCCOc1ccc(NCc2nc3[nH]c(CCC)cc(=O)n3n2)cc1]

2-(((4-(pentyloxy)phenyl)amino)methyl)-5-propyl-[1,2,4]triazolo[1,5-a]pyrimidin-7(4H)-one (5l) To a solution of NaOEt prepared from sodium (13 mg) and ethanol (1 mL), 2,3-diamino-6-propyl-pyrimidin-4-one (6a) (30 mg, 178 umol) was added and the reaction was heated at 80° C. for 30 min. Then, ethyl (4-(pentyloxy)phenyl)glycinate (7l) (47 mg, 178 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(((4-(pentyloxy)phenyl)amino)methyl)-5-propyl-[1,2,4]triazolo[1,5-a]pyrimidin-7(4H)-one (5l) (4.5 mg, 7%). $^1$H NMR (600 MHz, DMSO-d6) δ 13.06 (bs, 1H), 6.69 (d, 2H, J=9 Hz), 6.61 (d, 2H, J=9 Hz), 5.79 (s, 1H), 5.75 (bs, 1H), 4.28 (d, 2H, J=6 Hz), 3.81 (t, 2H, J=6.6 Hz), 2.54 (t, 2H, J=7.2 Hz), 1.67-1.61 (m, 2H), 1.37-1.30 (m, 4H), 0.92 (t, 3H, J=7.8 Hz), 0.89 (t, 3H, J=7.2 Hz); $^{13}$C NMR (150 MHz, DMSO-d6) δ 163.5, 156.4, 150.7, 143.0, 115.8, 113.8, 98.0, 68.3, 42.1, 34.7, 29.1, 28.2, 22.4, 21.7, 14.4, 13.7.

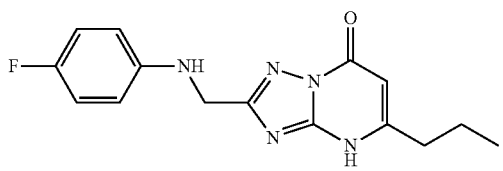 [SMILES: CCCc1cc(=O)n2nc(CNc3ccc(F)cc3)nc2[nH]1]

2-(((4-fluorophenyl)amino)methyl)-5-propyl-[1,2,4]triazolo[1,5-a]pyrimidin-7(4H)-one (5m) To a solution of NaOEt prepared from sodium (13 mg) and ethanol (1 mL), 2,3-diamino-6-propyl-pyrimidin-4-one (6a) (30 mg, 178 umol) was added and the reaction was heated at 80° C. for 30 min. Then, ethyl (4-fluorophenyl)glycinate (7m) (35 mg, 178 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-(((4-fluorophenyl)amino)methyl)-5-propyl-[1,2,4]triazolo[1,5-a]pyrimidin-7(4H)-one (5m) (16 mg, 30%). $^1$H NMR (600 MHz, DMSO-d6) δ 13.08 (bs, 1H), 6.92 (t, 2H, J=9 Hz), 6.67 (dd, 2H, J=9 and 4.8 Hz), 6.17 (t, 1H, J=6 Hz), 5.80 (s, 1H), 4.33 (d, 2H, J=6 Hz), 2.54 (t, 2H, J=7.2 Hz), 1.68-1.62 (m, 2H), 0.92 (t, 3H, J=7.2 Hz); $^{13}$C NMR (150 MHz, DMSO-d6) δ 163.2, 156.3, 155.7, 155.4, 154.1, 151.5, 145.5, 115.5, 113.5, 98.1, 41.8, 34.6, 21.6, 13.7.

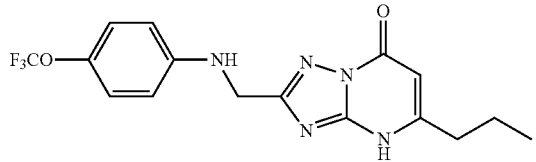 [SMILES: CCCc1cc(=O)n2nc(CNc3ccc(OC(F)(F)F)cc3)nc2[nH]1]

5-propyl-2-(((4-(trifluoromethoxy)phenyl)amino)methyl)-[1,2,4]triazolo[1,5-a]pyrimidin-7(4H)-one (5n) To a solution of NaOEt prepared from sodium (13 mg) and ethanol (1 mL), 2,3-diamino-6-propyl-pyrimidin-4-one (6a) (30 mg, 178 umol) was added and the reaction was heated at 80° C. for 30 min. Then, ethyl (4-(trifluoromethoxy)phenyl)glycinate (7n) (47 mg, 178 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 5-propyl-2-(((4-(trifluoromethoxy)phenyl)amino)methyl)-[1,2,4]triazolo[1,5-a]pyrimidin-7(4H)-one (5n) (19 mg, 29%). $^1$H NMR (600 MHz, DMSO-d6) δ 13.08 (bs, 1H), 7.06 (d, 2H, J=8.4 Hz), 6.71 (d, 2H, J=8.4 Hz), 6.56 (t, 1H, J=6.6 Hz), 5.81 (s, 1H), 4.37 (d, 2H, J=6.6 Hz), 2.55 (t, 2H, J=7.2 Hz), 1.67 (m, 2H), 0.92 (t, 3H, J=7.2 Hz); $^{13}$C NMR (150 MHz, DMSO-d6) δ 163.1, 156.3, 155.2, 151.5, 148.1, 139.1, 122.4, 121.7, 120.0, 113.1, 98.2, 41.3, 34.5, 21.6, 13.7

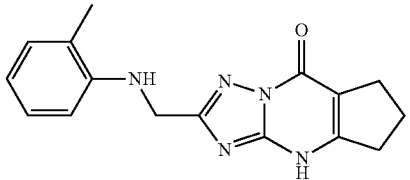 [SMILES: Cc1ccccc1NCc1nc2[nH]c3c(c(=O)n2n1)CCC3]

2-((o-tolylamino)methyl)-4,5,6,7-tetrahydro-8H-cyclopenta[d][1,2,4]triazolo[,5-a]pyrimidin-8-one (5o) To a solution of NaOEt prepared from sodium (6 mg) and ethanol (1 mL), 2,3-diamino-3,5,6,7-tetrahydro-4H-cyclopenta[d]pyrimidin-4-one (6b) (20 mg, 120 umol) was added and the reaction was heated at 80° C. for 30 min. Then, ethyl 2-(2-methylanilino)acetate (7a) (28 mg, 144 umol) was added to the reaction mixture and heated at reflux for 15 h, and then stirred at RT overnight. The precipitate obtained was filtered and dried under vacuum, then purified by flash column chromatography on silica gel (MeOH/CH$_2$Cl$_2$=1:30) to afford 2-((o-tolylamino)methyl)-4,5,6,7-tetrahydro-8H-cyclopenta[d][1,2,4]triazolo[1,5-a]pyrimidin-8-one (5o) (6.7 mg, 19%). $^1$H NMR (600 MHz, DMSO-d6) δ 13.31 (bs, 1H), 6.97 (m, 2H), 6.59 (d, 1H, J=7.8 Hz), 6.52 (t, 1H, J=7.2 Hz), 5.50 (t, 1H, J=6 Hz), 4.41 (d, 2H, J=6 Hz), 2.91 (t, 2H, J=7.2 Hz), 2.69 (t, 2H, J=7.2 Hz), 2.13 (s, 3H), 2.11-2.06 (m, 2H); ¹³C NMR (150 MHz, DMSO-d6) δ 173.2, 154.9, 151.9, 146.5, 130.2, 127.1, 122.2, 116.5, 110.0, 109.6, 41.7, 40.5, 31.9, 27.3, 22.2, 18.1.

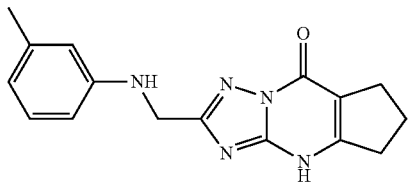 [SMILES: Cc1cccc(NCc2nc3[nH]c4c(c(=O)n3n2)CCC4)c1]

2-((m-tolylamino)methyl)-4,5,6,7-tetrahydro-8H-cyclopenta[d][1,2,4]triazolo[,5-a]pyrimidin-8-one (5p) To a solution of NaOEt prepared from sodium (6 mg) and ethanol (1 mL), 2,3-diamino-3,5,6,7-tetrahydro-4H-cyclopenta[d]pyrimidin-4-one (6b) (20 mg, 120 umol) was added and the reaction was heated at 80° C. for 30 min. Then, ethyl 2-(3-methylanilino)acetate (7b) (28 mg, 144 umol) was added to the reaction mixture and heated at reflux for 15 h, and then stirred at RT overnight. The precipitate obtained was filtered and dried under vacuum, then purified by flash column chromatography on silica gel (MeOH/CH₂Cl₂=1:30) to afford 2-((m-tolylamino)methyl)-4,5,6,7-tetrahydro-8H-cyclopenta[d][1,2,4]triazolo[1,5-a]pyrimidin-8-one (5p) (15.7 mg, 45%). ¹H NMR (600 MHz, DMSO-d6) δ 13.22, (bs, 1H), 6.87 (t, 1H, J=7.8 Hz), 6.41 (s, 1H), 6.39 (d, 1H, J=8.4 Hz), 6.29 (d, 1H, J=7.2 Hz), 6.00 (bs, 1H), 4.24 (d, 2H, J=4.2 Hz), 2.84 (t, H, J=7.8 Hz), 2.61 (t, 2H, J=7.2 Hz), 2.09 (s, 3H), 2.03-1.98 (m, 2H); ¹³C NMR (150 MHz, DMSO-d6) δ 163.1, 155.4, 154.8, 151.7, 148.8, 138.2, 129.1, 117.5, 113.5, 110.4, 110.0, 41.5, 31.8, 27.2, 22.2, 21.8.

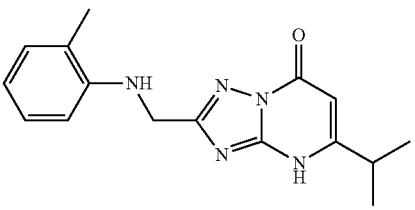

5-isopropyl-2-((o-tolylamino)methyl)-[1,2,4]triazolo[1,5-a]pyrimidin-7(4H)-one (5r) To a solution of NaOEt prepared from sodium (6 mg) and ethanol (1 mL), 2,3-diamino-6-isopropylpyrimidin-4(3H)-one (6c) (20 mg, 118.9 umol) was added and the reaction was heated at 80° C. for 30 min. Then, ethyl 2-(2-methylanilino)acetate (7a) (28 mg, 142.6 umol) was added to the reaction mixture and heated at reflux for 15 h, and then stirred at RT overnight. The precipitate obtained was filtered and dried under vacuum, then purified by flash column chromatography on silica gel (MeOH/CH₂Cl₂=1:30) to afford 5-isopropyl-2-((o-tolylamino)methyl)-[1,2,4]triazolo[1,5-a]pyrimidin-7(4H)-one (5r) (24.3 mg, 69%). ¹H NMR (600 MHz, DMSO-d6) δ 13.06 (BS, 1H), 6.98 (m, 2H), 6.6 (d, 1H, J=8.4 Hz), 6.52 (t, 1H, J=7.8 Hz), 5.81 (s, 1H), 5.51 (t, 1H, J=5.4 Hz), 4.43 (d, 2H, J=5.4 Hz), 2.87-2.82 (m, 1H), 2.13 (s, 3H), 1.24 (s, 3H), 1.23 (s, 3H); ¹³C NMR (150 MHz, DMSO-d6) δ 173.2, 163.4, 156.6, 151.5, 146.4, 130.2, 127.1, 122.2, 116.5, 110.0, 95.7, 41.5, 32.2, 21.3, 18.1.

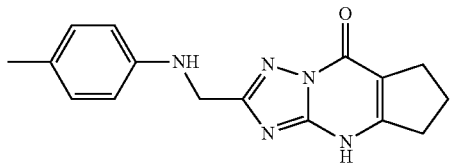 [SMILES: Cc1ccc(NCc2nc3[nH]c4c(c(=O)n3n2)CCC4)cc1]

2-((p-tolylamino)methyl)-4,5,6,7-tetrahydro-8H-cyclopenta[d][1,2,4]triazolo[,5-a]pyrimidin-8-one (5q) To a solution of NaOEt prepared from sodium (6 mg) and ethanol (1 mL), 2,3-diamino-3,5,6,7-tetrahydro-4H-cyclopenta[d]pyrimidin-4-one (6b) (20 mg, 120 umol) was added and the reaction was heated at 80° C. for 30 min. Then, ethyl 2-(4-methylanilino)acetate (7c) (28 mg, 144 umol) was added to the reaction mixture and heated at reflux for 15 h, and then stirred at RT overnight. The precipitate obtained was filtered and dried under vacuum, then purified by flash column chromatography on silica gel (MeOH/CH₂Cl₂=1:30) to afford 2-[(4-methylanilino)methyl]-5-propyl-4H-[1,2,4]triazolo[1,5-a]pyrimidin-7-one (5q) (9 mg, 25%). H NMR (600 MHz, DMSO-d6) δ13.29 (bs, 1H), 6.87 (d, 2H, J=8.4 Hz), 6.58 (d, 2H, J=8.4 Hz), 5.95 (s, 1H), 4.30 (d, 2H, J=5.4 Hz), 2.92 (t, 2H, J=7.8 Hz), 2.69 (t, 2H, J=7.2 Hz), 2.13 (s, 3H), 2.11-2.06 (m, 2H); ¹³C NMR (150 MHz, DMSO-d6) δ 173.3, 163.1, 154.8, 151.8, 146.5, 129.7, 124.9, 112.9, 110.3, 41.7, 31.8, 27.2, 22.2, 20.5.

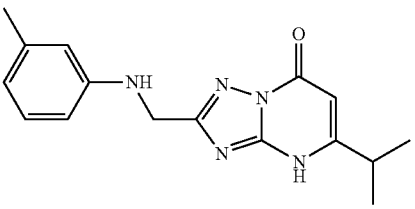 [SMILES: Cc1cccc(NCc2nc3[nH]c(C(C)C)cc(=O)n3n2)c1]

5-isopropyl-2-((m-tolylamino)methyl)-[1,2,4]triazolo[1,5-a]pyrimidin-7(4H)-one (5s) To a solution of NaOEt prepared from sodium (6 mg) and ethanol (1 mL), 2,3-diamino-6-isopropylpyrimidin-4(3H)-one (6c) (20 mg, 118.9 umol) was added and the reaction was heated at 80° C. for 30 min. Then, ethyl 2-(3-methylanilino)acetate (7b) (28 mg, 142.6 umol) was added to the reaction mixture and heated at reflux for 15 h, and then stirred at RT overnight. The precipitate obtained was filtered and dried under vacuum, then purified by flash column chromatography on silica gel (MeOH/CH₂Cl₂=1:30) to afford 5-isopropyl-2-((m-tolylamino)methyl)-[1,2,4]triazolo[1,5-a]pyrimidin-7(4H)-one (5s) (13.4 mg, 38%). ¹H NMR (600 MHz, DMSO-d6) δ 13.03 (bs, 1H), 6.95 (t, 1H, J=7.8 Hz), 6.48 (s, 1H), 6.47 (d, 1H, J=7.8 Hz), 6.37 (d, 1H, J=7.2 Hz), 6.09 (bs, 1H), 5.80 (s, 1H), 4.34 (d, 2H, J=3.6 Hz), 2.88 (m, 1H), 2.16 (s, 3H), 1.24 (s, 3H), 1.23 (s, 3H); ¹³C NMR (150 MHz, DMSO-d6) δ 172.7, 156.1, 151.0, 148.3, 137.8, 137.7, 128.7, 117.0, 113.0, 109.5, 95.2, 40.8, 31.7, 21.3, 20.9.

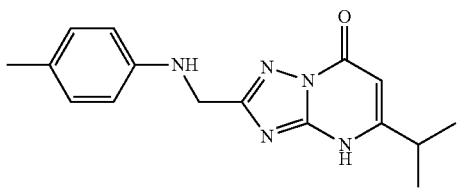 [SMILES: Cc1ccc(NCc2nc3[nH]c(C(C)C)cc(=O)n3n2)cc1]

5-isopropyl-2-((p-tolylamino)methyl)-[1,2,4]triazolo[1,5-a]pyrimidin-7(4H)-one (5t) To a solution of NaOEt prepared from sodium (6 mg) and ethanol (1 mL), 2,3-diamino-6-isopropylpyrimidin-4(3H)-one (6c) (20 mg, 118.9 umol) was added and the reaction was heated at 80° C. for 30 min. Then, ethyl 2-(4-methylanilino)acetate (7c) (28 mg, 142.6 umol) was added to the reaction mixture and heated at reflux for 15 h, and then stirred at RT overnight. The precipitate obtained was filtered and dried under vacuum, then purified by flash column chromatography on silica gel (MeOH/$CH_2Cl_2$=1:30) to afford 5-isopropyl-2-((p-tolylamino)methyl)-[1,2,4]triazolo[1,5-a]pyrimidin-7(4H)-one (5t) (11 mg, 32%). $^1$H NMR (600 MHz, DMSO-d6) δ; 12.96 (bs, 1H), 6.87 (d, 2H, J=7.8 Hz), 6.58 (d, 2H, J=8.4 Hz), 5.97 (bs, 1H), 5.80 (s, 1H), 4.32 (s, 2H), 2.87-2.83 (m, 1H), 2.13 (s, 3H), 1.24 (s, 3H), 1.23 (s, 3H); $^{13}$C NMR (150 MHz, DMSO-d6) δ 173.3, 156.6, 151.5, 146.5, 146.4, 129.7, 129.2, 112.9, 95.7, 41.6, 32.2, 21.4, 20.5.

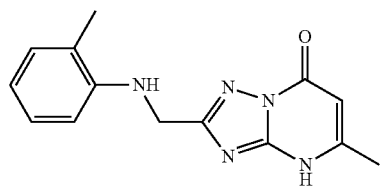 [SMILES: Cc1cc(=O)n2nc(CNc3ccccc3C)nc2[nH]1]

5-methyl-2-((o-tolylamino)methyl)-[1,2,4]triazolo[1,5-a]pyrimidin-7(4H)-one (5u) To a solution of NaOEt prepared from sodium (6 mg) and ethanol (1 mL), 2,3-diamino-6-methylpyrimidin-4(3H)-one (6d) (20 mg, 140 umol) was added and the reaction was heated at 80° C. for 30 min. Then, ethyl 2-(2-methylanilino)acetate (7a) (33 mg, 168 umol) was added to the reaction mixture and heated at reflux for 15 h, and then stirred at RT overnight. The precipitate obtained was filtered and dried under vacuum, then purified by flash column chromatography on silica gel (MeOH/$CH_2Cl_2$=1:30) to afford 5-methyl-2-((o-tolylamino)methyl)-[1,2,4]triazolo[1,5-a]pyrimidin-7(4H)-one (5u) (11.1 mg, 30%). $^1$H NMR (600 MHz, DMSO-d6) δ 13.12 (bs, 1H), 6.97 (m, 2H), 6.60 (d, 1H, J=7.8 Hz), 6.52 (t, 1H, J=7.8 Hz), 5.79 (s, 1H), 5.49 (t, 1H, J=6 Hz), 4.41 (d, 2H, J=6 Hz), 2.29 (s, 3H), 2.13 (s, 3H); $^{13}$C NMR (150 MHz, DMSO-d6) δ 172.8, 162.9, 155.7, 150.9, 146.0, 129.7, 126.7, 121.8, 116.1, 109.6, 98.2, 41.1, 18.6, 17.6.

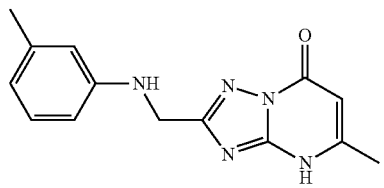 [SMILES: Cc1cccc(NCc2nc3[nH]c(C)cc(=O)n3n2)c1]

5-methyl-2-((m-tolylamino)methyl)-[1,2,4]triazolo[1,5-a]pyrimidin-7(4H)-one (5v) To a solution of NaOEt prepared from sodium (6 mg) and ethanol (1 mL), 2,3-diamino-6-methylpyrimidin-4(3H)-one (6d) (20 mg, 140 umol) was added and the reaction was heated at 80° C. for 30 min. Then, ethyl 2-(3-methylanilino)acetate (7b) (33 mg, 168 umol) was added to the reaction mixture and heated at reflux for 15 h, and then stirred at RT overnight. The precipitate obtained was filtered and dried under vacuum, then purified by flash column chromatography on silica gel (MeOH/$CH_2Cl_2$=1:30) to afford 5-methyl-2-((m-tolylamino)methyl)-[1,2,4]triazolo[1,5-a]pyrimidin-7(4H)-one (5v) (4.8 mg, 13%). $^1$H NMR (600 MHz, DMSO-d6) δ 13.10 (bs, 1H), 6.95 (t, 1H, J=7.8 Hz), 6.48 (s, 1H), 6.47 (d, 1H, J=7.8 Hz), 6.37 (d, 1H, J=7.2 Hz), 6.09 (t, 1H, J=6 Hz), 5.80 (s, 1H), 4.33 (d, 2H, J=6 Hz), 2.30 (s, 3H), 2.16 (s, 3H); $^{13}$C NMR (150 MHz, DMSO-d6) δ 163.3, 156.2, 151.7, 151.4, 148.8, 138.2, 129.1, 117.5, 113.5, 110.0, 98.7, 41.4, 21.8, 19.1.

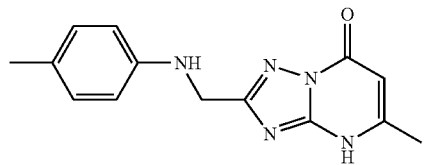

5-methyl-2-((p-tolylamino)methyl)-[1,2,4]triazolo[1,5-a]pyrimidin-7(4H)-one (5w) To a solution of NaOEt prepared from sodium (6 mg) and ethanol (1 mL), 2,3-diamino-6-methylpyrimidin-4(3H)-one (6d) (20 mg, 168 umol) was added and the reaction was heated at 80° C. for 30 min. Then, ethyl 2-(4-methylanilino)acetate (7c) (33 mg, 168 umol) was added to the reaction mixture and heated at reflux for 15 h, and then stirred at RT overnight. The precipitate obtained was filtered and dried under vacuum, then purified by flash column chromatography on silica gel (MeOH/$CH_2Cl_2$=1:30) to afford 5-methyl-2-((p-tolylamino)methyl)-[1,2,4]triazolo[1,5-a]pyrimidin-7(4H)-one (5w) (5.2 mg, 14%). $^1$H NMR (600 MHz, DMSO-d6) δ 13.08 (bs, 1H), 6.87 (d, 2H, J=7.8 Hz), 6.58 (d, 2H, J=8.4 Hz), 5.98 (s, 1H), 5.79 (s, 1H), 4.31 (d, 2H), 2.29 (s, 3H), 2.13 (s, 3H); $^{13}$C NMR (150 MHz, DMSO-d6) δ 163.4, 156.2, 151.7, 151.3, 146.5, 129.7, 124.9, 112.9, 98.7, 41.6, 20.5, 19.1

Biological Reagents and Chemicals

The human FECH expression plasmid pHDTF20 was obtained in *E. coli* cells from the Dailey Lab (University of Georgia). The cells were grown in Circlegrow medium (MP Biomedicals, LLC #3000-122) with ampicillin for 20 hours. Cells were harvested, lysed in a Tris-MOPS buffer and purified by immobilized metal affinity chromatography using HisPur Cobalt resin (Thermo Fisher #89965).

The activity assay buffer was 100 mM Tris-HCl pH 8.0 with 0.05% octyl glucoside detergent. Assay reagents included 100 µM NiCl (Sigma #339350), 0.75 µM FECH enzyme and 100 µM mesoporphyrin (Sigma #258806) prepared in ammonium hydroxide (Santa Cruz #sc-214535). FECH activity can be completely inhibited with 10 µM NMPP (Santa Cruz #sc-263846), and this was used a positive control in the screen.

Screening Optimization

The kinetic assay was optimized for a 384-well format. For the 384-well assay, each well contained a 50 µL reaction with 40 µL buffer, 5 µL mesoporphyrin solution, 5 µL NiCl and FECH solution. FECH activity was monitored, and the slope was consistently linear over the first 20 minutes of the reaction. This time point was used for the chemical screen. This assay gave Z'>0.5 across multiple replicate assays, where the positive control was FECH activity inhibited by NMPP and the negative control was FECH activity+DMSO vehicle alone.

Small Molecule Screen

Initial screening took place at the Indiana University School of Medicine Chemical Genomics Core Facility (CGCF) using the ChemDiv 10K and a portion (10,000 compounds) of the ChemBridge 50K libraries of chemical compounds. The compounds were diluted from parent plates with compounds in DMSO to the assay plate as 20 µL of a 25 µL solution in water for a final assay concentration of 10 µM. NMPP (2 µL) was added to two columns of wells on the assay plate left without compounds for a positive control. Two columns were also left without compounds to assay uninhibited FECH activity.

A mixture of assay buffer, NiCl and FECH enzyme (15 µL) was added to all wells on the assay plate using a MulitFlo dispenser. To start the reaction, 15 µL of a 333 µM mesoporphyrin solution in assay buffer was added to the plate, the plate spun down and the absorbance at OD=550 nm immediately read to establish a read at time 0. Plates were read for absorbance at OD=550 nm again at t=20 minutes and the activity was expressed as the change in the absorbance over the 20 minute reaction.

$IC_{50}$ Determination

Compounds, reordered from ChemDiv or synthesized as described above, were made to 10 mM in DMSO and tested in the FECH enzymatic assay at final concentrations of 100 µM to 100 pM (1% final DMSO concentration). $IC_{50}$ values for the compounds were determined using GraphPad Prism software.

Cell-Based $GI_{50}$ Determination

Human retinal microvascular endothelial cells (HRECs) were cultured in EGM-2 medium (Lonza). Cells (2500/well) in EGM-2 medium were plated in 48 wells in the center of a 96-well black with clear bottom TC treated plate are allowed to attach overnight. The cells were treated with compounds such that final assay concentrations were 100 µM, 30 µM, 10 µM, 3 µM, 1 µM, 100 nM, and 10 nM with DMSO control (1% final DMSO concentration). Cells were allowed to proliferate for 44 hours prior to addition of alamarBlue. The alamarBlue reagent is a fluorometric/colorimetric redox reagent that is reduced in the presence of growing cells. The assay was completed with a read of fluorescence at excitation of 560 nm and emission of 590 nm. $GI_{50}$ values were determined using GraphPad Prism software.

PPIX Accumulation Assay

To confirm that ferrochelatase is inhibited in HRECs after treatment with compounds, the buildup of FECH's substrate PPIX was assayed fluorometrically. HRECs were plated for 80% confluency at the time of treatment in 6 cm dishes coated with attachment factor. Cells were then treated with compound in DMSO (1% DMSO final concentration) for 2 hours at 37° C. 5-Aminolevulinic acid, the first dedicated precursor in the heme synthesis pathway, was then added to the cells at 1 mM and allowed to incubate at 37° C. for another 2 hours. Cells were washed with PBS and flash frozen. Cells were lysed in 200 µL RIPA buffer and cleared by centrifugation at 14,000 g for 15 minutes at 4° C. The cleared lysates (20 µL) were added to wells of a 384 well plate in triplicate. An equal volume of 2M HC104 prepared in methanol was added to each well and PPIX was detected by immediately reading fluorescence on a Biotek Synergy H1 plate reader at 406 nm excitation and 610 nm emission. Total PPIX accumulation was determined by comparing fluorescence output with PPIX standards, prepared in DMSO and diluted in RIPA buffer and 2M HC104 (1:1 ratio) and read on the same plate. Protein in the cleared lysates was quantified with a standard Bradford assay and the amount of PPIX accumulation is expressed per mg protein.

Tube Formation Assay

The Matrigel-based tube formation assay was performed. Briefly, 50 µL Matrigel was allowed to solidify in a 96-well black, clear bottom plate at 37° C. for 20 minutes. HRECs were added to the solid Matrigel at 15,000 cells/well in 100 µL EGM-2 and dosed with appropriate concentrations of compound in DMSO, 1 µL/well. Tube formation was observed every 2 hours by brightfield microscopy and images were taken after 8 hours of tube formation. Six images per treatment were analyzed using the AngiogenesisAnalyzer plugin for ImageJ and HREC total tubule length for treated cells was normalized to DMSO controls. Statistical analysis was completed using GraphPad Prism, with ANOVA followed by Dunnett's post hoc tests used to compare treatments to control (DMSO).

Results

High-Throughput Screen Identifies FECH Inhibitors

A kinetic assay to monitor FECH enzymatic activity was adapted from a published protocol (Burden et a., Biochim Biophys Acta 1435, 191-197 (1999)). Recombinant human FECH activity was established by monitoring the increase of $Ni^{2+}$ mesoporphyrin IX reaction product at 550 nm over time (FIG. 1).

Figure 2:
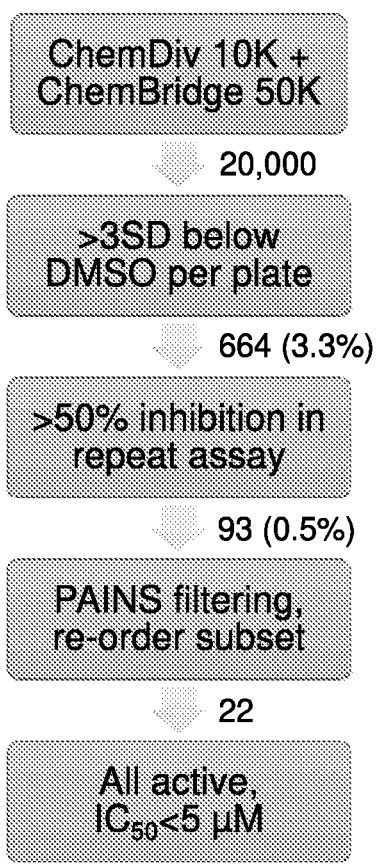
FIG. 2 depicts workflow for the high-throughput FECH screen. The number of compounds (% of the starting number) passing each stage is indicated.

20,000 compounds were analyzed in the initial screen (FIG. 2). Because each plate had both negative (uninhibited FECH activity) and positive (NMPP) controls, and there was considerable inter-plate variability, a hit was established as reduction >3 standard deviations from the average activity of the negative control (100% activity) for each plate. Using this metric, 664 (3.3%) of the compounds tested in the initial screen were designated hits. All these compounds were selected for secondary screening.

Figure 3:
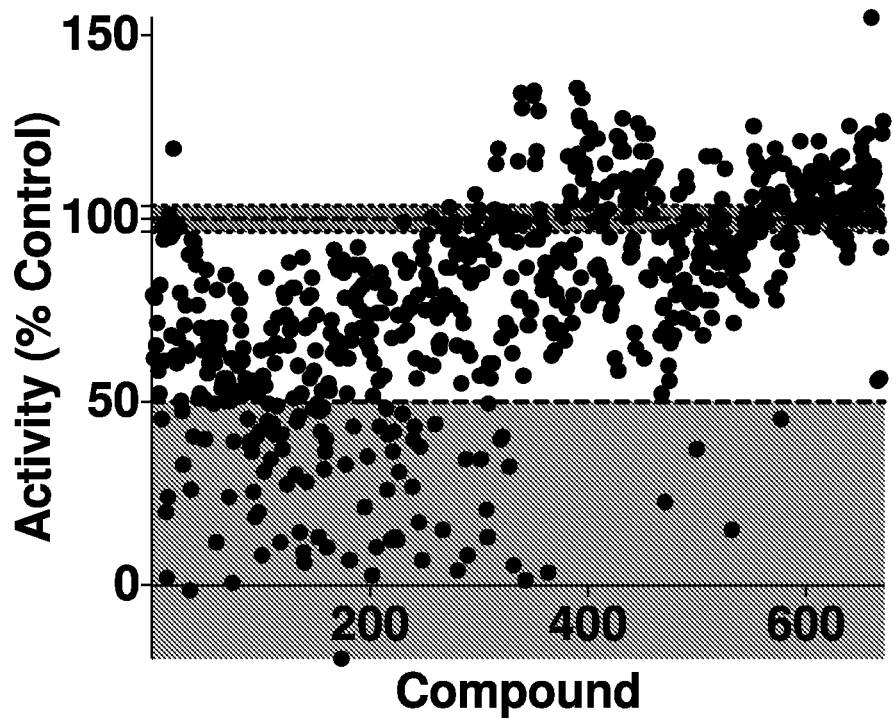
FIG. 3 depicts secondary screen results of 664 compounds tested at 10 μM. Hits were selected as those inhibiting FECH activity by >50% (lower shaded region) compared to DMSO control (mean±SD, upper shaded region). 93 compounds were selected as hits from this screen.

Secondary screening with these hits was run so that the assay was set up identically to the initial screen. However, analysis for hits from this secondary screen differed from the initial screen. Hits were defined from the secondary screen by their percent inhibition of FECH activity (the average of the activity from negative controls from two plates used in the secondary screen) (FIG. 3). The 93 compounds (0.5%) that inhibited FECH activity by 50% or more in this secondary screen were subjected to further scrutiny. Two were removed after pan-assay interference compound assessment. Intriguingly, the 91 remaining 'hit' compounds from the secondary screen (0.5% of the initial screen) included 62 triazolopyrimidinones. Twenty-two compounds, including 19 triazolopyrimidinones (Table 1), were reordered for dose-response testing.

TABLE 1

Triazolopyrimidinone screening hits, with IC$_{50}$ against recombinant FECH and GI$_{50}$ against proliferation of HRECs. (ND = no data)

| Library ID | Structure | FECH IC$_{50}$ (μM) | GI$_{50}$ on HRECs (μM) |
| --- | --- | --- | --- |
| D351-0312 | 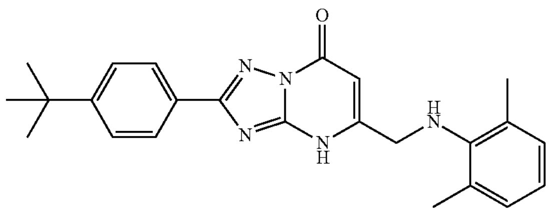 [SMILES: Cc1cccc(C)c1NCc1cc(=O)n2nc(-c3ccc(C(C)(C)C)cc3)nc2[nH]1] | 1.39 | >100 |
| D351-0310 | 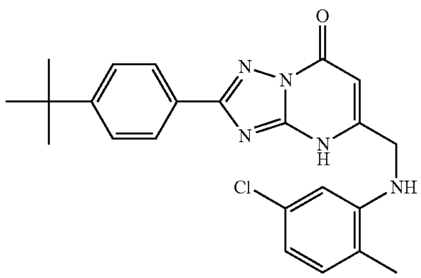 [SMILES: Cc1ccc(Cl)cc1NCc1cc(=O)n2nc(-c3ccc(C(C)(C)C)cc3)nc2[nH]1] | 0.0981 | 42.3 |
| D351-0414 | 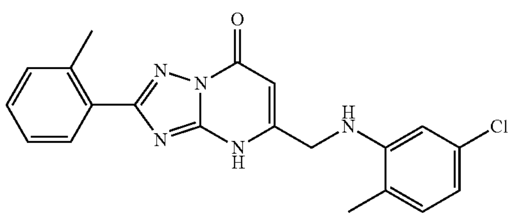 [SMILES: Cc1ccc(Cl)cc1NCc1cc(=O)n2nc(-c3ccccc3C)nc2[nH]1] | 0.346 | >100 |
| D351-0303 | 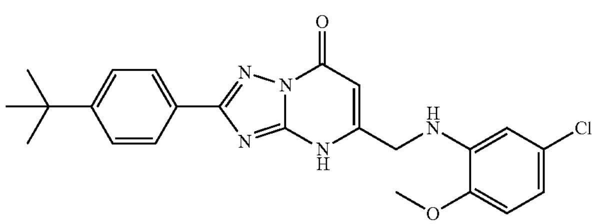 [SMILES: COc1ccc(Cl)cc1NCc1cc(=O)n2nc(-c3ccc(C(C)(C)C)cc3)nc2[nH]1] | 0.808 | 21.7 |
| D351-0319 | 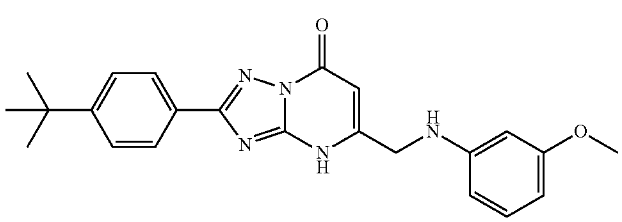 [SMILES: COc1cccc(NCc2cc(=O)n3nc(-c4ccc(C(C)(C)C)cc4)nc3[nH]2)c1] | 0.491 | >100 |
| D433-1800 | 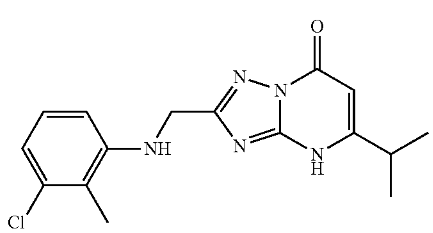 [SMILES: Cc1c(Cl)cccc1NCc1nc2[nH]c(C(C)C)cc(=O)n2n1] | 0.751 | ND |

TABLE 1-continued

Triazolopyrimidinone screening hits, with $IC_{50}$ against recombinant FECH and $GI_{50}$ against proliferation of HRECs. (ND = no data)

| Library ID | Structure | FECH $IC_{50}$ (μM) | $GI_{50}$ on HRECs (μM) |
| --- | --- | --- | --- |
| D433-1748 | 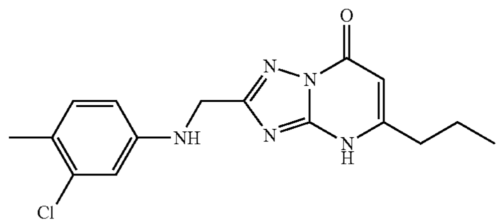 [SMILES: CCCc1cc(=O)n2nc(CNc3ccc(C)c(Cl)c3)nc2[nH]1] | 0.570 | >100 |
| D433-1750 | 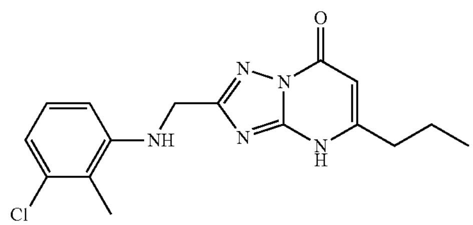 [SMILES: CCCc1cc(=O)n2nc(CNc3cccc(Cl)c3C)nc2[nH]1] | 2.15 | >100 |
| D433-1739 | 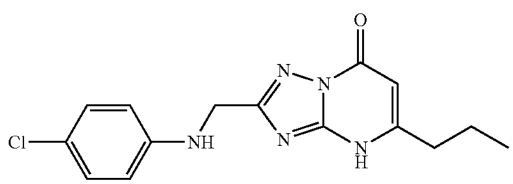 [SMILES: CCCc1cc(=O)n2nc(CNc3ccc(Cl)cc3)nc2[nH]1] | 0.829 | 3.14 |
| D433-1798 | 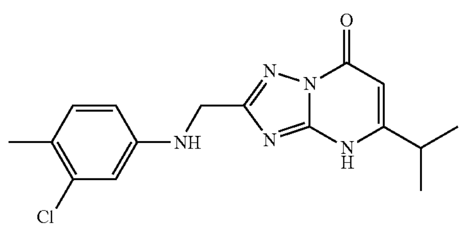 [SMILES: Cc1ccc(NCc2nc3[nH]c(C(C)C)cc(=O)n3n2)cc1Cl] | 1.02 | >100 |
| D433-1741 | 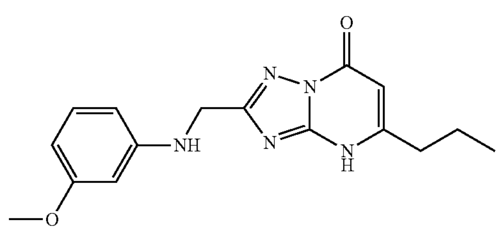 [SMILES: CCCc1cc(=O)n2nc(CNc3cccc(OC)c3)nc2[nH]1] | 2.86 | 1.61 |
| D433-1725 | 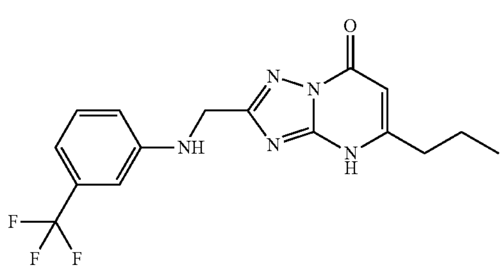 [SMILES: CCCc1cc(=O)n2nc(CNc3cccc(C(F)(F)F)c3)nc2[nH]1] | 4.39 | 1.17 |
| D433-1839 | 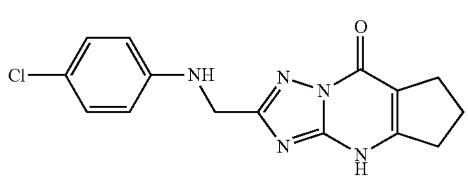 [SMILES: O=c1c2c([nH]c3nc(CNc4ccc(Cl)cc4)nn13)CCC2] | 1.05 | 81.5 |

TABLE 1-continued

Triazolopyrimidinone screening hits, with IC$_{50}$ against recombinant FECH and GI$_{50}$ against proliferation of HRECs. (ND = no data)

| Library ID | Structure | FECH IC$_{50}$ (μM) | GI$_{50}$ on HRECs (μM) |
|---|---|---|---|
| D433-1848 | 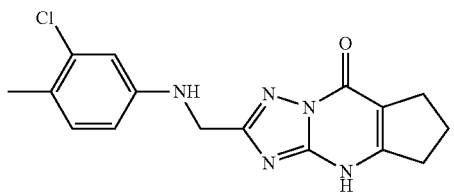 [SMILES: Cc1ccc(NCc2nc3[nH]c4c(c(=O)n3n2)CCC4)cc1Cl] | 0.227 | >100 |
| D433-1831 | 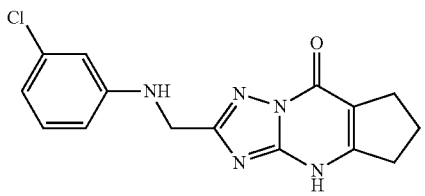 [SMILES: O=c1c2c([nH]c3nc(CNc4cccc(Cl)c4)nn13)CCC2] | 1.57 | >100 |
| D433-1841 | 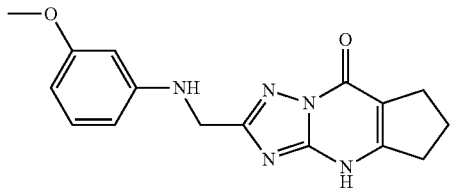 [SMILES: COc1cccc(NCc2nc3[nH]c4c(c(=O)n3n2)CCC4)c1] | 3.75 | >100 |
| D433-1688 | 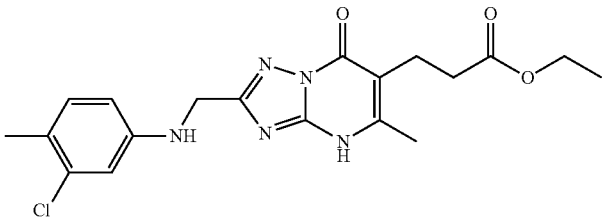 [SMILES: CCOC(=O)CCc1c(C)[nH]c2nc(CNc3ccc(C)c(Cl)c3)nn2c1=O] | 2.99 | >100 |
| D433-1585 | 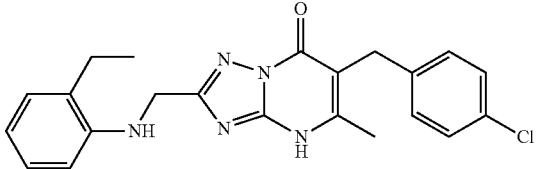 [SMILES: CCc1ccccc1NCc1nc2[nH]c(C)c(Cc3ccc(Cl)cc3)c(=O)n2n1] | 1.25 | 74.6 |
| D433-1582 | 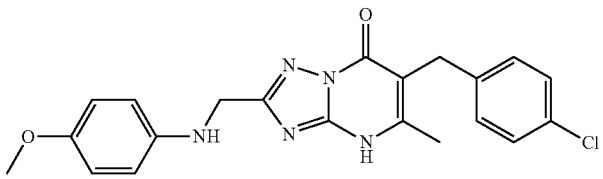 [SMILES: COc1ccc(NCc2nc3[nH]c(C)c(Cc4ccc(Cl)cc4)c(=O)n3n2)cc1] | 0.0614 | >100 |

Dose Response Assays Confirm Activity Against FECH and in Cells

Figure 4:
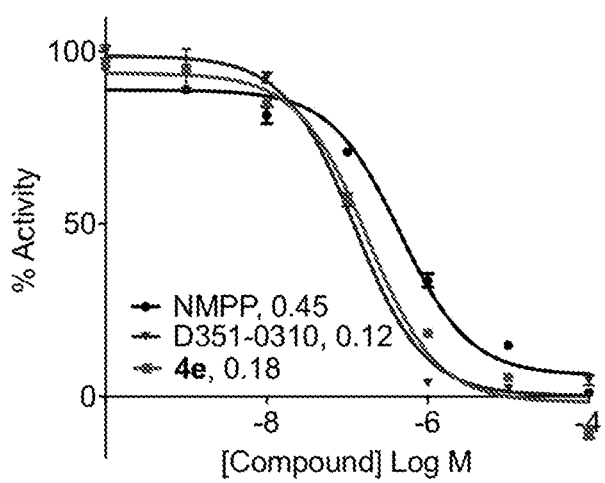
FIG. 4 depicts the dose-response for inhibition of FECH. $IC_{50}$ (μM) against recombinant FECH indicated for positive control compound NMPP, screening hit D351-0310, and novel compound 4e.

Ten of the compounds tested had an IC$_{50}$ value in the low micromolar range with nine in the mid- to high nanomolar range (Table 1; FIG. 4), indicating fairly potent FECH inhibition, comparable to NMPP (IC$_{50}$=450 nM in our assay).

To assess the potential disease-treatment relevance of these hits, the effect of these compounds on angiogenesis were analyzed. Since FECH knockdown and inhibition with NMPP or griseofulvin reduces Human Retinal Endothelial Cell (HREC) proliferation, this was used as an initial assessment of the bioactivity of the screening hits. HREC proliferation was inhibited only in the micromolar range (Table 1), suggesting that further SAR was needed to find potently cell-active FECH inhibitors.

Synthetic Compounds Inhibited FECH

To explore the SAR of triazolopyrimidinone inhibition of FECH, a series of compounds were synthesized as described above. From 4-tert-butylbenzoic acid, aminotriazole 1, which was the starting point for a series of 4-tert-butylphenyltriazolopyrimidinones, 2, 3, 4a-4h (Scheme 1), was synthesized. Further analogs modified on the left and right sides were subsequently synthesized (5a~5w) (Scheme 2). Using the same screening methods as in the FECH activity assay, compounds 1, 2, 3, 4a~4h, and 5a~5w were tested for FECH inhibition (Table 2). Two compounds in the first series (4a~4h) were potent FECH inhibitors, with one compound (4e) performing better than the control compound NMPP (FIG. 2), and having an effect on HREC proliferation (Table 2). There were substantially more active compounds in the second series (5a~5w), with compounds 5a, 5c, 5d, and 5h showing a good balance of activity against recombinant FECH and antiproliferative effects on HRECs (Table 2).

TABLE 2

Synthetic triazolopyrimidinones, with $IC_{50}$ against recombinant FECH and $GI_{50}$ against proliferation of HRECs.

| Example | Structure | FECH $IC_{50}$ (μM) | $GI_{50}$ on HRECs (μM) |
|---|---|---|---|
| 1 | 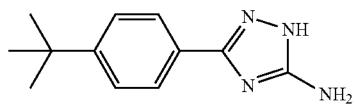 [SMILES: CC(C)(C)c1ccc(-c2n[nH]c(N)n2)cc1] | >100 | >100 |
| 2 | 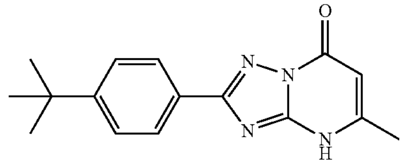 [SMILES: Cc1cc(=O)n2nc(-c3ccc(C(C)(C)C)cc3)nc2[nH]1] | >100 | >100 |
| 3 | 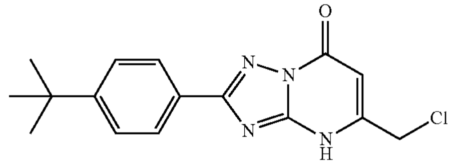 [SMILES: CC(C)(C)c1ccc(-c2nc3[nH]c(CCl)cc(=O)n3n2)cc1] | >100 | >100 |
| 4a | 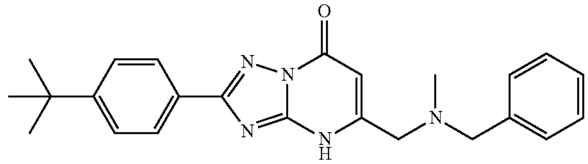 [SMILES: CN(Cc1ccccc1)Cc1cc(=O)n2nc(-c3ccc(C(C)(C)C)cc3)nc2[nH]1] | >100 | >100 |
| 4b | 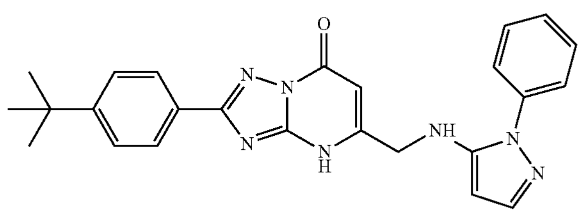 [SMILES: CC(C)(C)c1ccc(-c2nc3[nH]c(CNc4ccnn4-c4ccccc4)cc(=O)n3n2)cc1] | >100 | >100 |
| 4c | 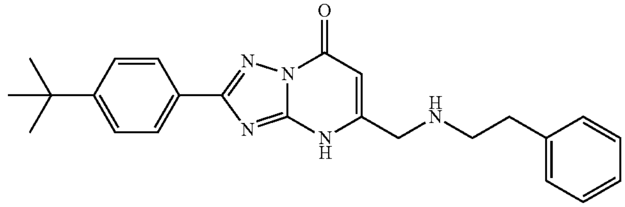 [SMILES: CC(C)(C)c1ccc(-c2nc3[nH]c(CNCCc4ccccc4)cc(=O)n3n2)cc1] | >100 | >100 |
| 4d | 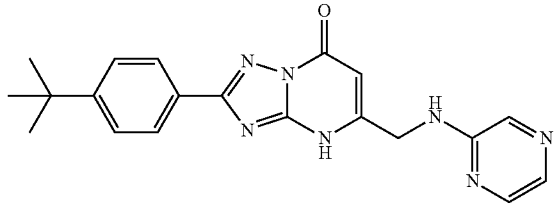 [SMILES: CC(C)(C)c1ccc(-c2nc3[nH]c(CNc4cnccn4)cc(=O)n3n2)cc1] | >100 | >100 |

TABLE 2-continued
Synthetic triazolopyrimidinones, with IC$_{50}$ against recombinant FECH and GI$_{50}$ against proliferation of HRECs.
| Example | Structure | FECH IC$_{50}$ (μM) | GI$_{50}$ on HRECs (μM) |
|---|---|---|---|
| 4e | 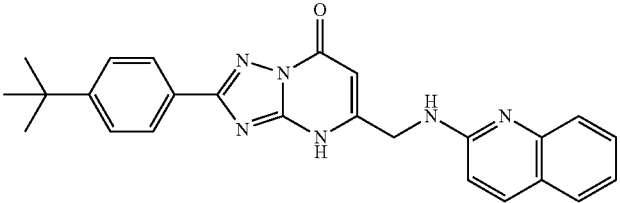 [SMILES: CC(C)(C)c1ccc(-c2nc3[nH]c(CNc4ccc5ccccc5n4)cc(=O)n3n2)cc1] | 0.178 | 92.5 |
| 4f | 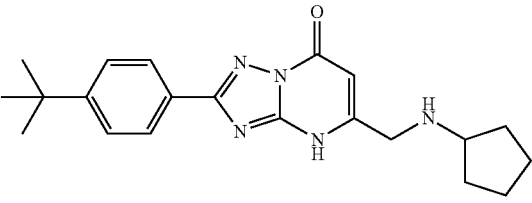 [SMILES: CC(C)(C)c1ccc(-c2nc3[nH]c(CNC4CCCC4)cc(=O)n3n2)cc1] | >100 | >100 |
| 4g | 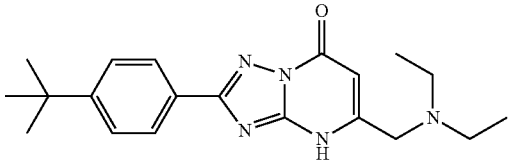 [SMILES: CCN(CC)Cc1cc(=O)n2nc(-c3ccc(C(C)(C)C)cc3)nc2[nH]1] | >100 | >100 |
| 4h | 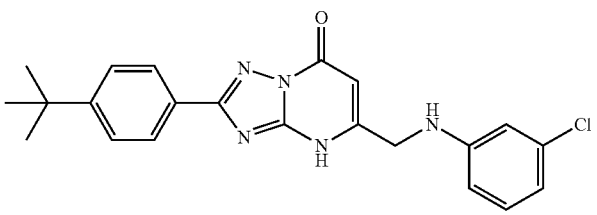 [SMILES: CC(C)(C)c1ccc(-c2nc3[nH]c(CNc4cccc(Cl)c4)cc(=O)n3n2)cc1] | 0.511 | >100 |
| 5a | 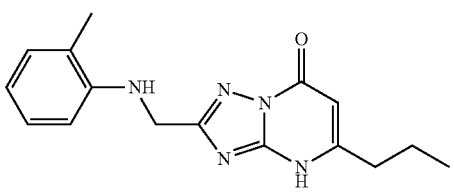 [SMILES: CCCc1cc(=O)n2nc(CNc3ccccc3C)nc2[nH]1] | 92 | 75.5 |
| 5b | 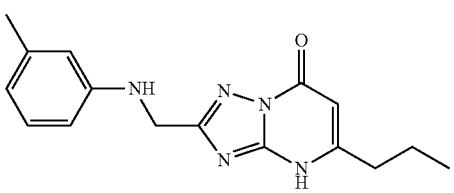 [SMILES: CCCc1cc(=O)n2nc(CNc3cccc(C)c3)nc2[nH]1] | 0.508 | >100 |
| 5c | 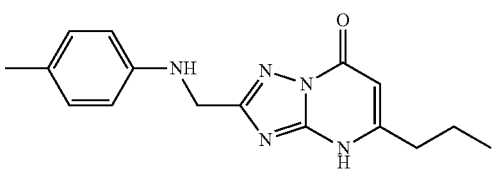 [SMILES: CCCc1cc(=O)n2nc(CNc3ccc(C)cc3)nc2[nH]1] | 0.293 | 28.3 |

TABLE 2-continued

Synthetic triazolopyrimidinones, with IC$_{50}$ against recombinant FECH and GI$_{50}$ against proliferation of HRECs.

| Example | Structure | FECH IC$_{50}$ (μM) | GI$_{50}$ on HRECs (μM) |
| --- | --- | --- | --- |
| 5d | 2-Cl-phenyl derivative | >100 | 25.7 |
| 5e | 3-Cl-phenyl derivative | 0.346 | >100 |
| 5f | 4-Cl-phenyl derivative | 0.0916 | >100 |
| 5g | 2-biphenyl derivative | 27.3 | >100 |
| 5h | 4-tert-butyl-phenyl derivative | >100 | 3.8 |
| 5i | 3-Cl-4-F-phenyl derivative | 0.0336 | >100 |
| 5j | 4-ethyl-phenyl derivative | 10.6 | >100 |

TABLE 2-continued

Synthetic triazolopyrimidinones, with IC$_{50}$ against recombinant FECH and GI$_{50}$ against proliferation of HRECs.

| Example | Structure | FECH IC$_{50}$ (μM) | GI$_{50}$ on HRECs (μM) |
|---|---|---|---|
| 5k | 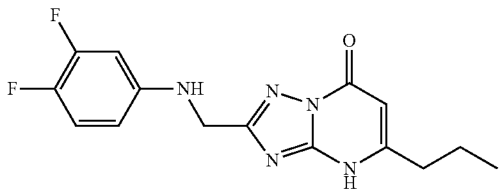 [SMILES: CCCc1cc(=O)n2nc(CNc3ccc(F)c(F)c3)nc2[nH]1] | 0.0429 | >100 |
| 5l | 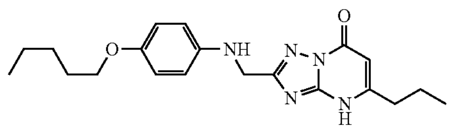 [SMILES: CCCCCOc1ccc(NCc2nc3[nH]c(CCC)cc(=O)n3n2)cc1] | 78 | >100 |
| 5m | 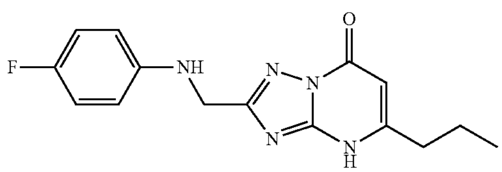 [SMILES: CCCc1cc(=O)n2nc(CNc3ccc(F)cc3)nc2[nH]1] | 0.525 | >100 |
| 5n | 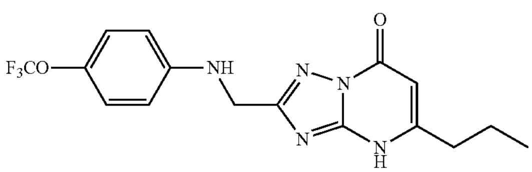 [SMILES: CCCc1cc(=O)n2nc(CNc3ccc(OC(F)(F)F)cc3)nc2[nH]1] | 34.1 | >100 |
| 5o | 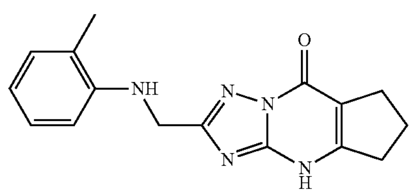 [SMILES: Cc1ccccc1NCc1nc2[nH]c3c(c(=O)n2n1)CCC3] | >100 | >100 |
| 5p | 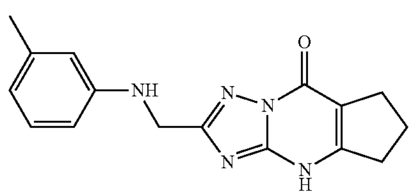 [SMILES: Cc1cccc(NCc2nc3[nH]c4c(c(=O)n3n2)CCC4)c1] | 9.34 | >100 |
| 5q | 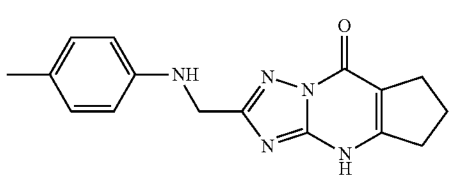 [SMILES: Cc1ccc(NCc2nc3[nH]c4c(c(=O)n3n2)CCC4)cc1] | 3.62 | >100 |
| 5r | 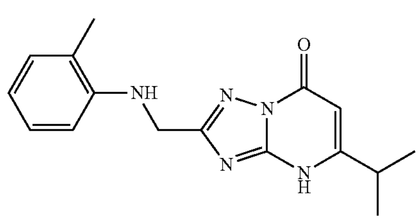 [SMILES: Cc1ccccc1NCc1nc2[nH]c(C(C)C)cc(=O)n2n1] | 17.9 | >100 |

TABLE 2-continued

Synthetic triazolopyrimidinones, with $IC_{50}$ against recombinant FECH and $GI_{50}$ against proliferation of HRECs.

| Example | Structure | FECH $IC_{50}$ (μM) | $GI_{50}$ on HRECs (μM) |
|---|---|---|---|
| 5s | 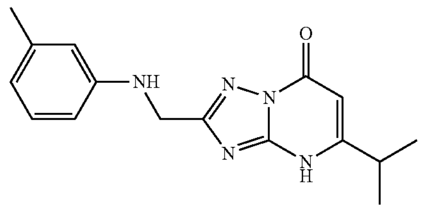 [SMILES: Cc1cccc(NCc2nc3[nH]c(C(C)C)cc(=O)n3n2)c1] | 28.1 | >100 |
| 5t | 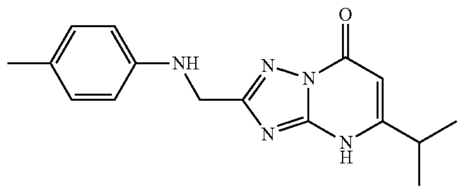 [SMILES: Cc1ccc(NCc2nc3[nH]c(C(C)C)cc(=O)n3n2)cc1] | 16.8 | >100 |
| 5u | 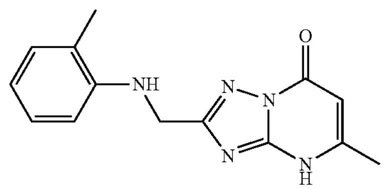 [SMILES: Cc1cc(=O)n2nc(CNc3ccccc3C)nc2[nH]1] | 77.2 | >100 |
| 5v | 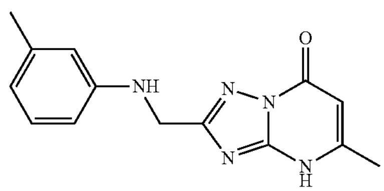 [SMILES: Cc1cccc(NCc2nc3[nH]c(C)cc(=O)n3n2)c1] | 18.7 | >100 |
| 5w | 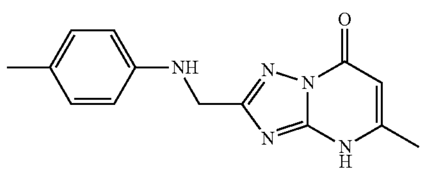 | 22.5 | >100 |

Figure 5:
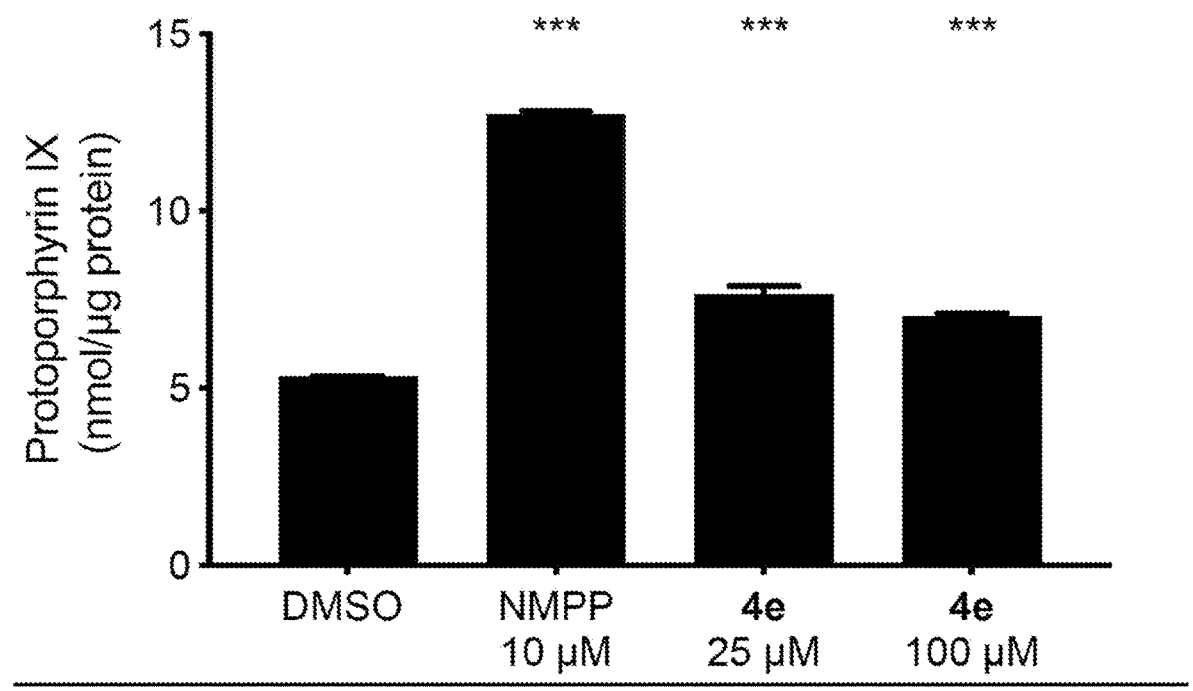
FIG. 5. depicts the buildup of protoporphyrin IX (PPIX) in HRECs. FECH inhibition should lead to a buildup of its substrate PPIX. Treatment with both NMPP, a known FECH inhibitor, and two concentrations of compound 4e led to an accumulation of PPIX in HRECs, showing that these compounds are inhibiting FECH in the cells. ***, p<0.001 vs. DMSO control, ANOVA with Dunnett's post hoc test. Mean±SD, n=3.

To assess if novel compounds could inhibit FECH activity in cells, the buildup of the FECH substrate PPIX was assessed in HRECs treated with compound 4e. After enhancing flux through the heme synthesis pathway by treatment with the heme precursor 5-ALA, it was observed that both compound 4e and the positive control compound NMPP induced a buildup of PPIX (FIG. 5). This finding indicates that 4e acts as a FECH inhibitor in the cellular context.

Angiogenesis Assay

Figure 6A:
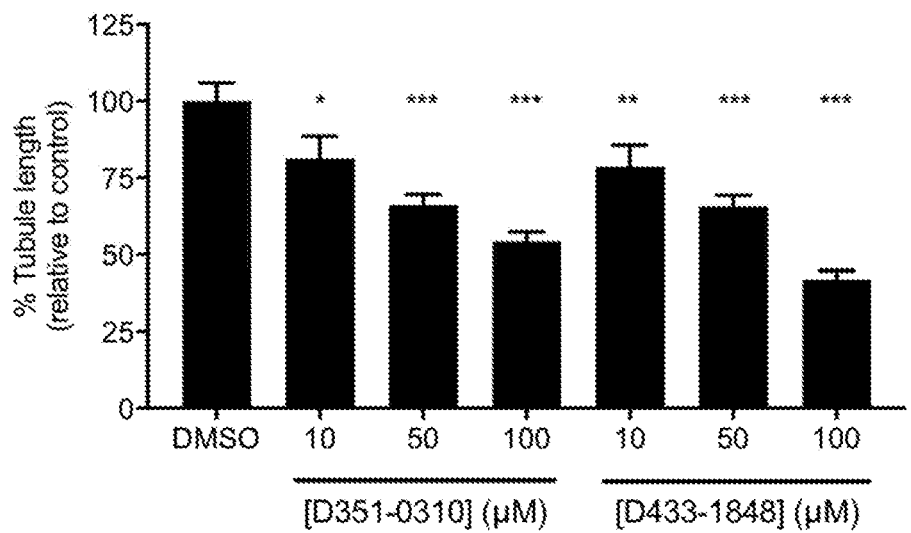
FIGS. 6A & 6B depict that triazolopyrimidinones dose-dependently blocked tube formation of HRECs.
Figure 6B:
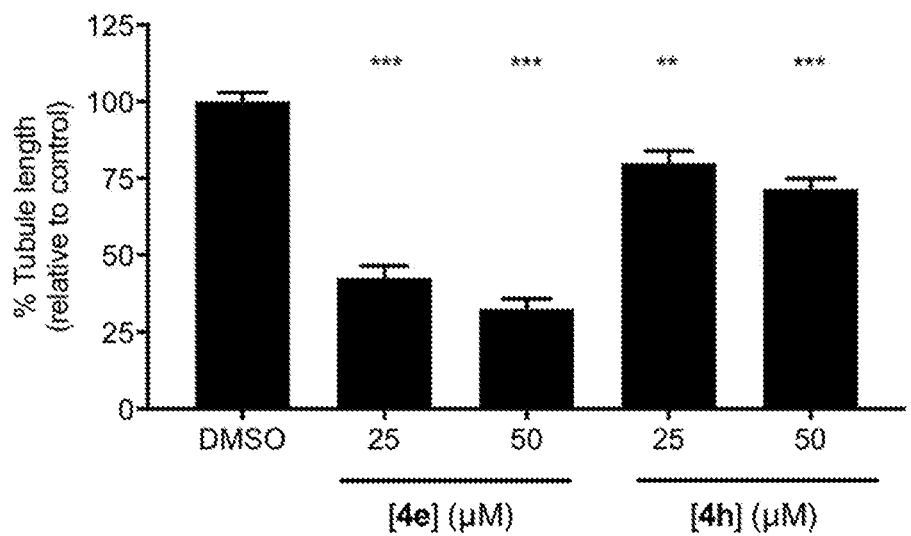
Figure 7A:
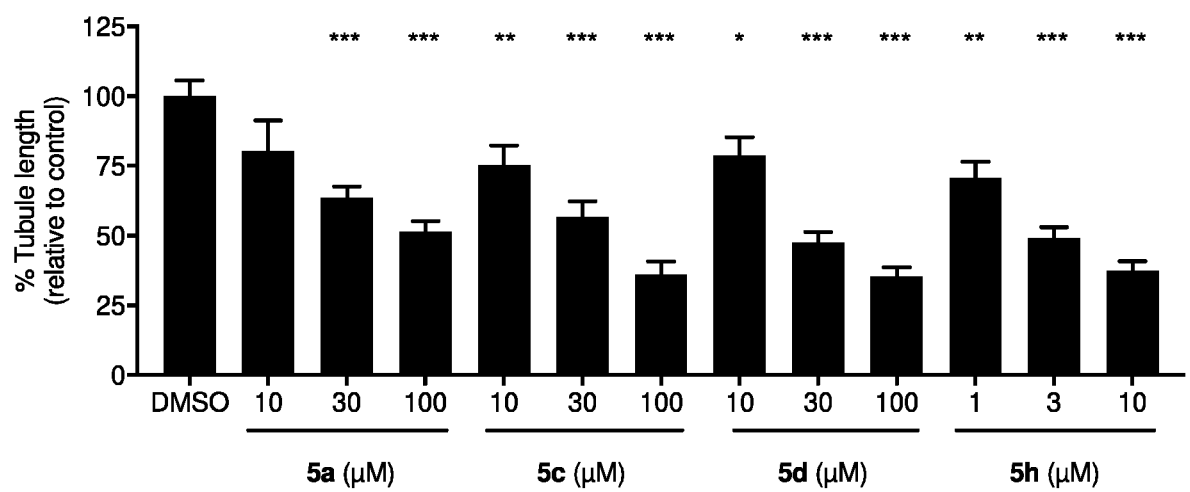
FIGS. 7A-D depict that novel triazolopyrimidinones dose-dependently blocked tube formation of HRECs. Shown are the effects of newly synthesized compounds, active against FECH, on HREC tube formation, with representative images. *, p<0.05; , p<0.01; *, p<0.001 vs. DMSO control, ANOVA with Dunnett's post hoc test. Mean±SEM, n=6. Scale bar=500 μm.
Figure 7B:
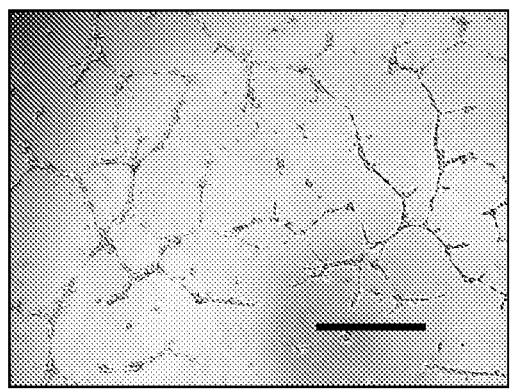
Figure 7B:
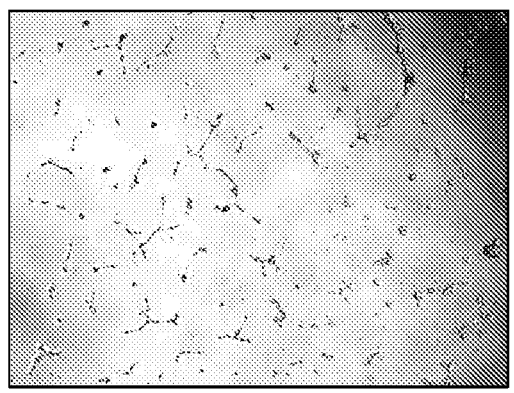
Figure 7C:
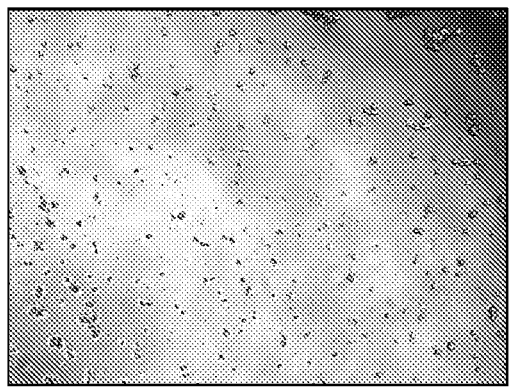
Figure 7C:
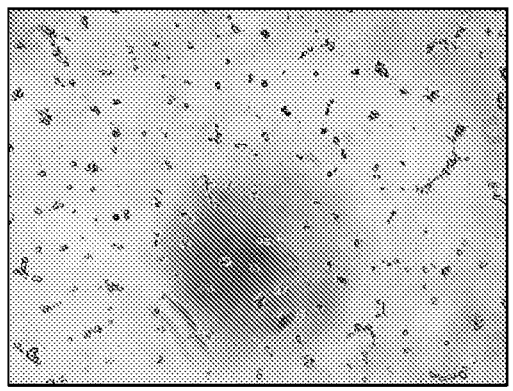
Figure 7D:
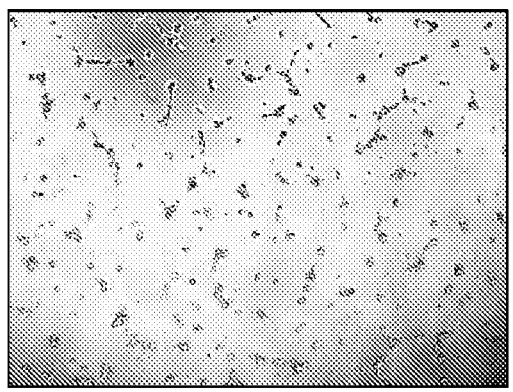

Inhibition of FECH by the canonical chemical inhibitor, NMPP, also inhibits angiogenic properties of HRECs beyond proliferation. To see if the small molecules identified as FECH inhibitors in the compound screen had a similar effect, two compounds were tested in a Matrigel based tube formation assay. Both compounds blocked tube formation effectively (FIG. 6A). Moreover, several newly-synthesized triazolopyrimidinones with good FECH inhibitory activity and effects on HREC proliferation, 4e, 4h, 5a, 5c, 5d, and 5h, also blocked tube formation of HRECs (FIGS. 6B and 7). These findings are suggestive of antiangiogenic activity in vivo, to be explored in future.

DISCUSSION

The enzyme FECH has significant promise for therapeutic targeting in multiple diseases, and lacks good, targeted inhibitors. A high-throughput screen was used to find FECH inhibitors. There was a striking over-representation of triazolopyrimidinones amongst the screening hits, suggesting that this scaffold might have promise as the basis of FECH inhibitors, and room for SAR studies to optimize inhibition. Several triazolopyrimidinones showed FECH inhibition and antiangiogenic activity in some cases. These compounds could form the basis for new therapies for neovascular diseases or malaria, or be combined with 5-aminolevulinic acid for PDT or PDD of various cancers.

What is claimed is:

1. A compound of the formula

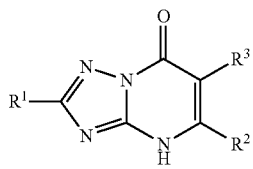

wherein $R^1$ is $C_6$-$C_{10}$ aryl or $C_1$-$C_6$ alkylNR$^4$R$^5$, wherein $C_6$-$C_{10}$ aryl is substituted with a $C_1$-$C_6$ alkyl;

each of $R^2$ and $R^3$ is independently selected from the group consisting of H, $C_1$-$C_6$ alkyl, or $C_1$-$C_6$ alkylNR$^6$R$^7$, provided that at least one of $R^2$ and $R^3$ is not H, and when $R^1$ is $C_1$-$C_6$ alkylNR$^4$R$^5$, then $R^2$ is $C_3$-$C_6$ alkyl, and $R^3$ is H, wherein each hydrogen atom in $C_1$-$C_6$ alkyl is independently optionally substituted with fluoro, chloro, bromo, or iodo;

$R^4$ is H;

$R^5$ is biphenyl, 4-tert-butylphenyl, 3-chloro-4-fluoro-phenyl, 3-fluoro-4-fluoro-phenyl, 4-(O—$C_1$-$C_6$ alkoxy) phenyl, 4-(OCF$_3$)phenyl, 2-methylphenyl, and each of $R^6$ or $R^7$ is independently selected from the group consisting of H, $C_3$-$C_6$ cycloalkyl, 5 to 7-membered monocyclic heteroaryl, $C_6$-$C_{10}$ bicyclic heteroaryl, or $C_2$-$C_6$ alkyl-$C_6$-$C_{10}$ aryl, or each of $R^6$ and $R^7$ is $C_1$-$C_6$ alkyl, wherein each hydrogen atom in $C_1$-$C_6$ alkyl, $C_3$-$C_6$ cycloalkyl, 5 to 7-membered monocyclic heteroaryl, $C_6$-$C_{10}$ bicyclic heteroaryl, or $C_2$-$C_6$ alkyl-$C_6$-$C_{10}$ aryl is independently optionally substituted with fluoro, chloro, bromo, iodo, $C_1$-$C_6$ alkyl, —O$C_1$-$C_6$ alkyl, —OCF$_3$, —CF$_3$ or $C_6$-$C_{10}$ aryl;

or a pharmaceutically acceptable salt thereof.

2. The compound of claim 1, or a pharmaceutically acceptable salt thereof, wherein $R^1$ is 4-tert-butylphenyl.

3. The compound of claim 1, or a pharmaceutically acceptable salt thereof, wherein $R^2$ is $C_1$-$C_6$ alkylNR$^6$R$^7$, and $R^3$ is H.

4. The compound of claim 1, or a pharmaceutically acceptable salt thereof, wherein $R^1$ is $C_1$-$C_6$ alkylNR$^4$R$^5$.

5. The compound of claim 1, or a pharmaceutically acceptable salt thereof, wherein $R^2$ is n-propyl or iso-propyl, and $R^3$ is H.

6. The compound of claim 1, or a pharmaceutically acceptable salt thereof, selected from the group consisting of

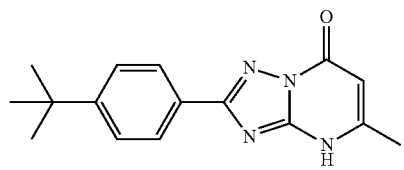

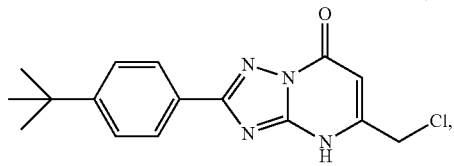

-continued

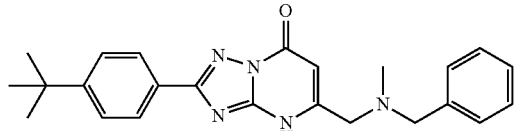

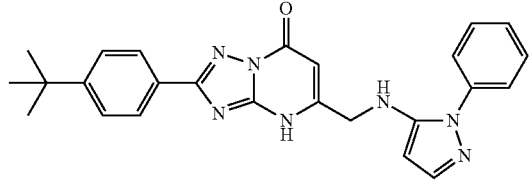

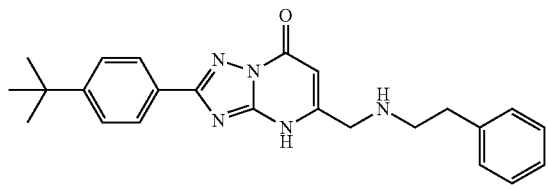

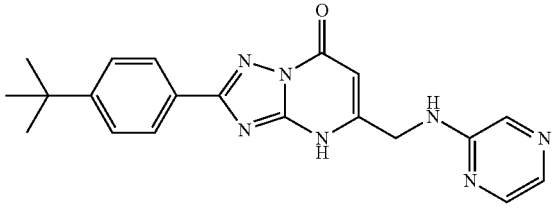

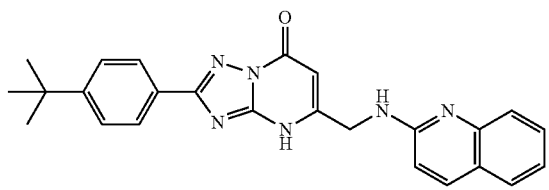

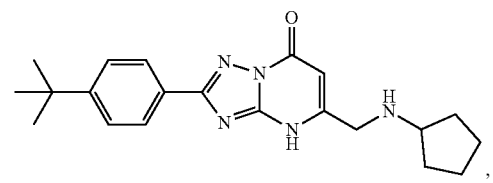

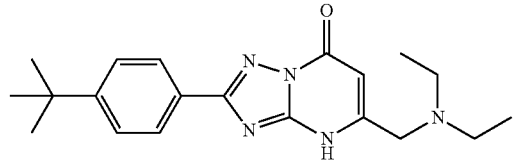

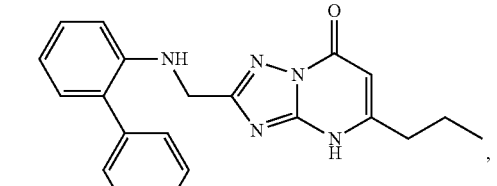

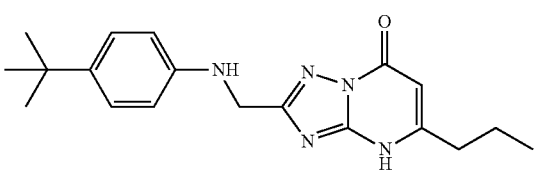

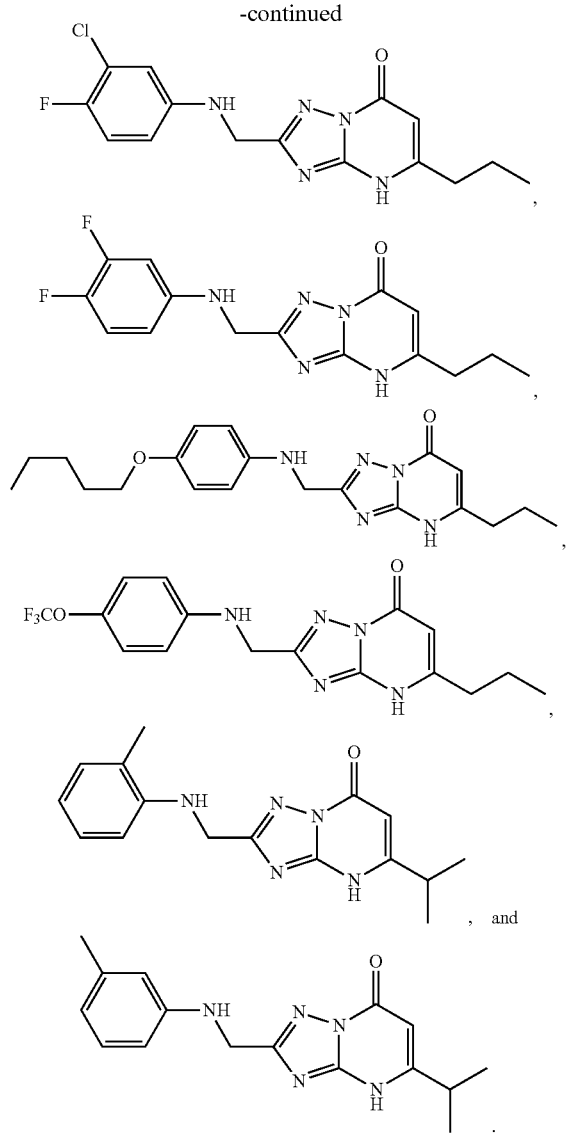
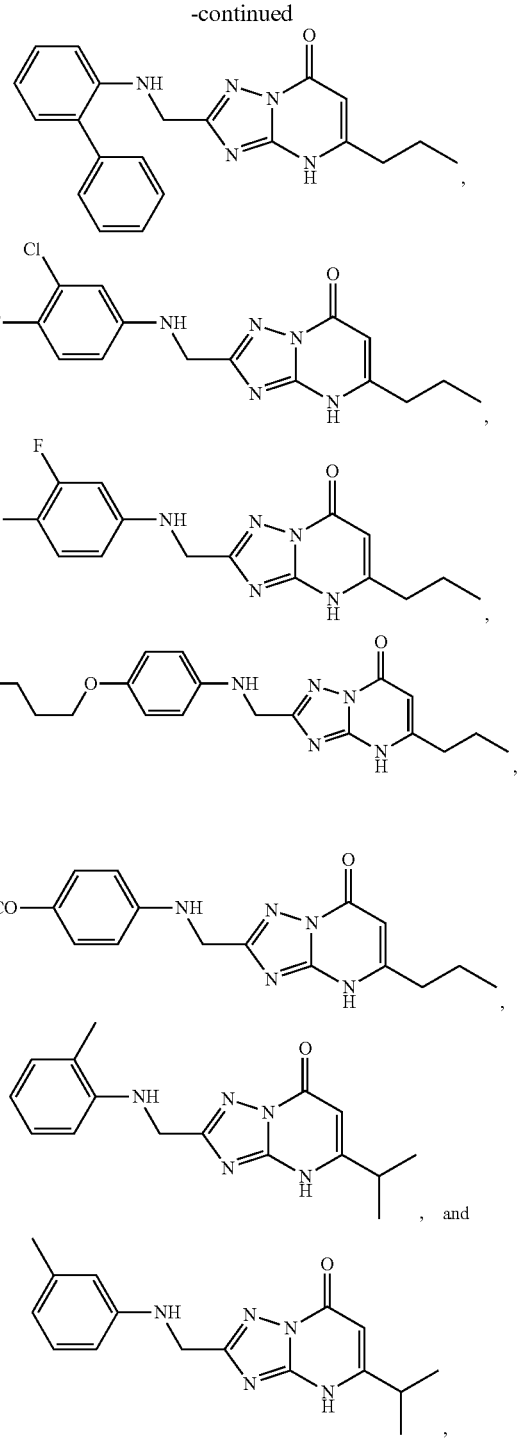
7. The compound of claim 3, wherein R⁶ is H and R⁷ is C₆-C₁₀ bicyclic heteroaryl.
8. The compound of claim 1, selected from the group consisting of
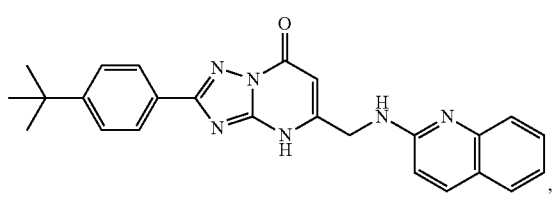
or a pharmaceutically acceptable salt thereof.
* * * * *